US009637547B2

(12) United States Patent
Ab et al.

(10) Patent No.: US 9,637,547 B2
(45) Date of Patent: May 2, 2017

(54) MONOCLONAL ANTIBODIES FOR DETECTION OF FOLATE RECEPTOR 1

(71) Applicant: ImmunoGen, Inc., Waltham, MA (US)

(72) Inventors: Olga Ab, Millis, MA (US); Daniel Tavares, Natick, MA (US); Julianto Setiady, Waltham, MA (US); Sharron Ladd, Burlington, MA (US); Christina N. Carrigan, Belmont, MA (US); Lingyun Rui, Weston, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/473,828

(22) Filed: Aug. 29, 2014

(65) Prior Publication Data

US 2015/0093388 A1 Apr. 2, 2015

Related U.S. Application Data

(60) Provisional application No. 61/940,184, filed on Feb. 14, 2014, provisional application No. 61/875,475, filed on Sep. 9, 2013, provisional application No. 61/872,407, filed on Aug. 30, 2013.

(51) Int. Cl.
| | |
|---|---|
| *C07K 16/30* | (2006.01) |
| *A61K 47/48* | (2006.01) |
| *G01N 33/574* | (2006.01) |
| *C07K 16/28* | (2006.01) |
| *A61K 39/00* | (2006.01) |

(52) U.S. Cl.
CPC ........ *C07K 16/30* (2013.01); *A61K 47/48384* (2013.01); *A61K 47/48561* (2013.01); *C07K 16/28* (2013.01); *G01N 33/57411* (2013.01); *G01N 33/57415* (2013.01); *G01N 33/57449* (2013.01); *G01N 33/57492* (2013.01); *A61K 2039/505* (2013.01); *C07K 2317/24* (2013.01); *C07K 2317/33* (2013.01); *C07K 2317/565* (2013.01); *C07K 2317/92* (2013.01); *G01N 2800/52* (2013.01)

(58) Field of Classification Search
CPC .... C07K 16/30; C07K 16/28; C07K 2317/33; C07K 2317/24; C07K 2317/92; C07K 2317/565; G01N 33/57415; G01N 33/57411; G01N 33/57449; G01N 33/57492; G01N 2800/52; A61K 47/48384; A61K 47/48561; A61K 2039/505
See application file for complete search history.

(56) References Cited

U.S. PATENT DOCUMENTS

| | | | |
|---|---|---|---|
| 5,416,016 A | 5/1995 | Low et al. | |
| 5,720,954 A | 2/1998 | Hudziak et al. | |
| 5,855,866 A | 1/1999 | Thorpe et al. | |
| 6,051,230 A | 4/2000 | Thorpe et al. | |
| 7,033,594 B2 | 4/2006 | Low et al. | |
| 7,112,317 B2 | 9/2006 | Thorpe et al. | |
| 7,125,541 B2 | 10/2006 | Thorpe et al. | |
| 7,465,449 B2 | 12/2008 | Violette et al. | |
| 7,740,854 B2 | 6/2010 | Low et al. | |
| 7,915,388 B2 | 3/2011 | Wu et al. | |
| 8,124,083 B2* | 2/2012 | Grasso ............. | A61K 47/48469 424/133.1 |
| 8,153,126 B2 | 4/2012 | Violette et al. | |
| 8,236,319 B2 | 8/2012 | Chari et al. | |
| 8,557,966 B2 | 10/2013 | Ab et al. | |
| 8,557,996 B2 | 10/2013 | Chaffee et al. | |
| 8,709,432 B2 | 4/2014 | Carrigan et al. | |
| 8,795,673 B2 | 8/2014 | Li et al. | |
| 9,133,275 B2 | 9/2015 | Ab et al. | |
| 9,200,073 B2 | 12/2015 | Carrigan et al. | |
| 2003/0028009 A1 | 2/2003 | Huse | |
| 2003/0148406 A1 | 8/2003 | King et al. | |
| 2003/0157090 A1 | 8/2003 | Benvenuto et al. | |
| 2003/0229208 A1 | 12/2003 | Queen et al. | |
| 2003/0233675 A1 | 12/2003 | Cao et al. | |
| 2004/0031072 A1 | 2/2004 | La Rosa et al. | |
| 2004/0087478 A1 | 5/2004 | Gillen et al. | |
| 2004/0157214 A1 | 8/2004 | McCafferty et al. | |
| 2004/0170630 A1 | 9/2004 | Huang et al. | |
| 2004/0180386 A1 | 9/2004 | Carr et al. | |
| 2004/0235840 A1 | 11/2004 | Chari et al. | |
| 2005/0025763 A1 | 2/2005 | Williams et al. | |
| 2005/0244901 A1 | 11/2005 | Peschen et al. | |
| 2006/0030524 A1 | 2/2006 | Cohen et al. | |
| 2006/0110771 A1 | 5/2006 | Katagiri et al. | |
| 2006/0228349 A1 | 10/2006 | Acton et al. | |

(Continued)

FOREIGN PATENT DOCUMENTS

| | | |
|---|---|---|
| CN | 101139613 A | 3/2008 |
| CN | 101440130 A | 5/2009 |

(Continued)

OTHER PUBLICATIONS

O'Shannessy DJ, et al. Oncotarget. 2(12): 1227-1243. Dec. 2011. Available online at www.impactjournals.com/oncotarget. PMID:22204844.*
Ab, O., et al., "Anitbody-Maytansinoid Conjugates Targeting Folate Receptor 1 for Cancer Therapy," 2010 EORTC-NCI-AACR Symposium—Berlin, Germany (Nov. 16-19, 2010), Abstract 236, 1 Page, American Association for Cancer Research, Germany (distributed in print Nov. 16, 2010; available online Oct. 29, 2010).
Ab, O., et al., "IMGN853, An Anti-Folate Receptor 1 Antibody-maytansinoid Conjugate for Targeted Cancer Therapy," 102nd Annual AACR Meeting—Orlando, FL (Apr. 2-6, 2011), Abstract 4576, 1 Page, American Association for Cancer Research, United States (distributed in print Mar. 8, 2011; available online Feb. 25, 2011).

(Continued)

*Primary Examiner* — Robert Landsman
(74) *Attorney, Agent, or Firm* — Sterne, Kessler, Goldstein & Fox P.L.L.C.

(57) ABSTRACT

The invention generally relates to antibodies that bind to human folate receptor and diagnostic assays for folate receptor 1-based therapies. Methods of using the antibodies to monitor therapy are further provided.

36 Claims, 18 Drawing Sheets

(56) References Cited

U.S. PATENT DOCUMENTS

| | | |
|---|---|---|
| 2006/0239910 A1 | 10/2006 | Nicolaides et al. |
| 2007/0041985 A1 | 2/2007 | Unger et al. |
| 2007/0048315 A1 | 3/2007 | Presta |
| 2007/0071675 A1 | 3/2007 | Wu et al. |
| 2007/0098719 A1 | 5/2007 | Smith et al. |
| 2007/0099251 A1 | 5/2007 | Zhang et al. |
| 2007/0231266 A1 | 10/2007 | Low et al. |
| 2007/0253950 A1 | 11/2007 | Jacobsen |
| 2007/0286858 A1 | 12/2007 | Clancy et al. |
| 2007/0294782 A1 | 12/2007 | Abad et al. |
| 2008/0081047 A1 | 4/2008 | Berry et al. |
| 2008/0104734 A1 | 5/2008 | Kav et al. |
| 2008/0131366 A1 | 6/2008 | Ratnam |
| 2008/0138396 A1 | 6/2008 | Low et al. |
| 2008/0171014 A1 | 7/2008 | Wu et al. |
| 2008/0181888 A1 | 7/2008 | Ambrose et al. |
| 2008/0227704 A1 | 9/2008 | Kamens |
| 2008/0260748 A1 | 10/2008 | Iwamoto et al. |
| 2009/0081710 A1 | 3/2009 | Low et al. |
| 2009/0087478 A1 | 4/2009 | Hansen et al. |
| 2009/0104215 A1 | 4/2009 | Ekiel et al. |
| 2009/0136516 A1 | 5/2009 | Tedder et al. |
| 2009/0156788 A1 | 6/2009 | Presta et al. |
| 2009/0169547 A1 | 7/2009 | Sahin et al. |
| 2009/0186027 A1 | 7/2009 | Solomon et al. |
| 2009/0214636 A1 | 8/2009 | Low et al. |
| 2009/0215165 A1 | 8/2009 | Rance et al. |
| 2009/0232822 A1 | 9/2009 | Joseloff et al. |
| 2009/0274697 A1 | 11/2009 | Grasso et al. |
| 2009/0274713 A1 | 11/2009 | Chari et al. |
| 2009/0280124 A1 | 11/2009 | Labat et al. |
| 2009/0280128 A1 | 11/2009 | Kamogawa et al. |
| 2009/0285795 A1 | 11/2009 | Patell |
| 2009/0285813 A1 | 11/2009 | Frey et al. |
| 2009/0317921 A1 | 12/2009 | Groome et al. |
| 2009/0324491 A1 | 12/2009 | Aburatani et al. |
| 2009/0324594 A1 | 12/2009 | Nicolaides et al. |
| 2010/0055034 A1 | 3/2010 | Martin et al. |
| 2010/0086537 A1 | 4/2010 | Sooknanan et al. |
| 2010/0087509 A1 | 4/2010 | Van Rompaey et al. |
| 2010/0092470 A1 | 4/2010 | Bhatt et al. |
| 2010/0104626 A1 | 4/2010 | Leamon et al. |
| 2010/0111852 A1 | 5/2010 | Yoshida |
| 2010/0111866 A1 | 5/2010 | Kratz |
| 2010/0129314 A1 | 5/2010 | Singh et al. |
| 2010/0239581 A1 | 9/2010 | Joseloff et al. |
| 2010/0255479 A1 | 10/2010 | Mikolajczyk et al. |
| 2010/0272741 A1 | 10/2010 | Knutson et al. |
| 2010/0323973 A1 | 12/2010 | Leamon et al. |
| 2010/0330572 A1 | 12/2010 | Assaraf et al. |
| 2011/0002942 A1 | 1/2011 | Presta et al. |
| 2011/0021555 A1 | 1/2011 | Nordsiek et al. |
| 2011/0038867 A1 | 2/2011 | Pincelli et al. |
| 2011/0059469 A1 | 3/2011 | Aburatani et al. |
| 2011/0195022 A1 | 8/2011 | Deckert et al. |
| 2011/0256127 A1 | 10/2011 | Bourhis et al. |
| 2012/0009181 A1 | 1/2012 | Ab et al. |
| 2012/0177664 A1 | 7/2012 | Yokoseki et al. |
| 2012/0183552 A1 | 7/2012 | Joseloff et al. |
| 2012/0207771 A1 | 8/2012 | O'Shannessy et al. |
| 2012/0251532 A1 | 10/2012 | Violette et al. |
| 2012/0253021 A1 | 10/2012 | Li et al. |
| 2012/0259100 A1 | 10/2012 | Jin |
| 2012/0282282 A1 | 11/2012 | Lutz et al. |
| 2012/0282637 A1 | 11/2012 | Huber et al. |
| 2013/0039916 A1 | 2/2013 | Presta et al. |
| 2013/0295119 A1 | 11/2013 | Ab et al. |
| 2014/0072587 A1 | 3/2014 | Morariu |
| 2014/0099332 A1 | 4/2014 | Testa et al. |
| 2014/0363451 A1 | 12/2014 | Running et al. |
| 2014/0363453 A1 | 12/2014 | Carrigan et al. |
| 2015/0132323 A1 | 5/2015 | Lutz et al. |
| 2015/0297744 A1 | 10/2015 | Lutz et al. |
| 2015/0306242 A1 | 10/2015 | Li et al. |
| 2016/0060339 A1 | 3/2016 | Ab et al. |
| 2016/0075781 A1 | 3/2016 | Ab et al. |

FOREIGN PATENT DOCUMENTS

| | | |
|---|---|---|
| EP | 1900752 A1 | 3/2008 |
| EP | 1864133 B1 | 3/2010 |
| WO | WO-9429351 A2 | 12/1994 |
| WO | WO-9711971 A1 | 4/1997 |
| WO | WO-02071928 A2 | 9/2002 |
| WO | WO-2004110498 A2 | 12/2004 |
| WO | WO-2005003154 A2 | 1/2005 |
| WO | WO-2005080431 A2 | 9/2005 |
| WO | WO-2006105141 A1 | 10/2006 |
| WO | WO-2006116592 A2 | 11/2006 |
| WO | WO-2007006041 A2 | 1/2007 |
| WO | WO-2007020965 A1 | 2/2007 |
| WO | WO-2007094754 A2 | 8/2007 |
| WO | WO-2007147265 A1 | 12/2007 |
| WO | WO-2008021290 A2 | 2/2008 |
| WO | WO-2008031577 A1 | 3/2008 |
| WO | WO-2008072723 A1 | 6/2008 |
| WO | WO-2008101231 A2 | 8/2008 |
| WO | WO-2008103473 A1 | 8/2008 |
| WO | WO-2008145136 A1 | 12/2008 |
| WO | WO-2009080759 A1 | 7/2009 |
| WO | WO-2009087978 A1 | 7/2009 |
| WO | WO-2009132081 A2 | 10/2009 |
| WO | WO-2010033733 A1 | 3/2010 |
| WO | WO-2010111388 A2 | 9/2010 |
| WO | WO-2011042548 A1 | 4/2011 |
| WO | WO-2011106528 A1 | 9/2011 |
| WO | WO-2012061759 A2 | 5/2012 |
| WO | WO-2012135675 A2 | 10/2012 |
| WO | WO-2012138749 A1 | 10/2012 |
| WO | WO-2013012722 A1 | 1/2013 |
| WO | WO-2014036495 A2 | 3/2014 |
| WO | WO-2014186403 A2 | 11/2014 |

OTHER PUBLICATIONS

Ab, O., et al., "IMGN853, An Anti-Folate Receptor 1 Antibody-maytansinoid Conjugate for Targeted Cancer Therapy," 102nd Annual AACR Meeting—Orlando, FL (Apr. 2-6, 2011), Abstract 4576 Poster, American Association for Cancer Research, United States (Apr. 2, 2011).

Allard, J.E., et al., "Overexpression of Folate Binding Protein is Associated with Shortened Progression-free Survival in Uterine Adenocarcinomas," Gynecologic Oncology 107(1):52-57, Academic Press, United States (2007).

Antony, A.C., "Folate Receptors," Annual Review of Nutrition 16:501-521, Annual Reviews, United States (1996).

Armstrong, D.K., et al., "Efficacy and Safety of Farletuzumab, a Humanized Monoclonal Antibody to Folate Receptor Alpha, in Platinum-sensitive Relapsed Ovarian Cancer Subjects: Preliminary Data from a Phase-2 Study," European Journal of Cancer Suppl. 7:450, Elsevier Science Ltd., England (2009).

Armstrong, D.K., et al., "Exploratory Phase II Efficacy Study of MORAb-003, a Monoclonal Antibody Against Folate Receptor Alpha, in Platinum-sensitive Ovarian Cancer in First Relapse," Journal of Clinical Oncology Suppl.26:293S, American Society of Clinical Oncology, United States (2008).

Basal, E., et al., "Functional Folate Receptor Alpha is Elevated in the Blood of Ovarian Cancer Patients," PloS One 4(7):e6292, Public Library of Science, United States (2009).

Baselga, J., et al., "Phase II Study of Weekly Intravenous Recombinant Humanized Anti-p185HER2 Monoclonal Antibody in Patients with HER2/neu Overexpressing Metastatic Breast Cancer," Journal of Clinical Oncology 14(3):737-744, American Society of Clinical Oncology, United States (1996).

Bendig, M.M., "Humanization of Rodent Monoclonal Antibodies by CDR Grafting," Methods: A Companion to Methods in Enzymology 8(2):83-93, Academic Press, United States (1995).

(56) References Cited

OTHER PUBLICATIONS

Brown, M., et al., "Tolerance of Single, but Not Multiple, Amino Acid Replacements in AntibodyVH CDR2: A Means of Minimizing B Cell Wastage from Somatic Hypermutation?," Journal of Immunology 156(9):3285-3291, American Association of Immunologists, United States (1996).

Bueno, R., et al., "The Alpha Folate Receptor is Highly Activated in Malignant Pleural Mesothelioma," The Journal of Thoracic and Cardiovascular Surgery 121(2):225-233, Mosby, United States (2001).

Cagle, P.T., et al., "Folate Receptor in Adenocarcinoma and Squamous Cell Carcinoma of the Lung: Potential Target for Folate-linked Therapeutic Agents," Archives of Pathology and Laboratory Medicine 137(2):241-244, College of American Pathologists, United States (Feb. 2013).

Carrigan, C.N., et al., "Evaluation of Folate Receptor 1 (FOLR1) Expression by Calibrated Immunohistochemistry Identifies Candidate Tumor subtypes for Targeting by IMGN853, an Anti-FOLR1-maytansinoid Conjugate," 102nd Annual AACR Meeting—Orlando, FL (Apr. 2-6, 2011), Abstract 3617, 1 Page, American Association for Cancer Research, United States (distributed in print Mar. 8, 2011; available online Feb. 25, 2011).

Carrigan, C.N., et al., "Evaluation of Folate Receptor 1 (FOLR1) Expression by Calibrated Immunohistochemistry Identifies Candidate Tumor Subtypes for Targeting by IMGN853, an Anti-FOLR1-Maytansinoid Conjugate," 102nd Annual AACR Meeting—Orlando, FL (Apr. 2-6, 2011), Abstract 3617 Poster, American Association for Cancer Research, United States (Apr. 2, 2011).

Chen, J., et al., "Antibody-cytotoxic Agent Conjugates for Cancer Therapy," Expert Opinion on Drug Delivery 2(5):873-890, Informa Healthcare, England (2005).

Chen, Y., et al., "Drug Delivery Across the Blood-brain Barrier," Current Drug Delivery 1(4):361-376, Bentham Science Publishers, United Arab Emirates (2004).

Colman, P.M., "Effects of Amino Acid Sequence Changes on Antibody-antigen Interactions," Research in Immunology 145(1):33-36, Elsevier, France (1994).

Colnaghi, M.I., "Generation of Monoclonal Antibodies for in Vivo Approaches," International Journal of Radiation Applications and Instrumentation. Part B, Nuclear Medicine and Biology 18(1):15-18, Pergamon Press, England (1991).

Conde, F.P., et al., "The Aspergillus Toxin Restriction is a Suitable Cytotoxic Agent for Generation of Immunoconjugates with Monoclonal Antibodies Directed Against Human Carcinoma Cells," European Journal of Biochemistry / FEBS 178(3):795-802, Federation of European Biochemical Societies, England (1989).

Coney, L.R., et al., "Chimeric Murine-human Antibodies Directed Against Folate Binding Receptor are Efficient Mediators of Ovarian Carcinoma Cell Killing," Cancer Research 54(9):2448-2455, American Association for Cancer Research, United States (1994).

Coney, L.R., et al., "Cloning of a Tumor-associated Antigen: MOv18 and MOv19 Antibodies Recognize a Folate-binding Protein," Cancer Research 51(22):6125-6132, American Association for Cancer Research, United States (1991).

Copeland, A., et al., "B1G510 (B1G510_9BURK) Unreviewed, UniProtKB/TrEMBL," UniProt, 3 pages, last modified Dec. 14, 2011, accessed at &,It;http://www.uniprot.org/uniprot/B1G510>.

Dirks, N.L., et al., "Population Pharmacokinetics of Cetuximab in Patients With Squamous Cell Carcinoma of the Head and Neck," Journal of Clinical Pharmacology 48(3):267-278, The American College of Clinical Pharmacology, United States (2008).

Ebel, W., et al., "Preclinical Evaluation of MORAb-003, a Humanized Monoclonal Antibody Antagonizing Folate Receptor-Alpha," Cancer Immunity 7:6, Cancer Research Institute, United States (2007).

English language Abstract of Chinese Patent Publication No. 101139613A, European Patent Office, espacenet database—Worldwide, (2012).

English language Abstract of Chinese Patent Publication No. 101440130A, European Patent Office, espacenet database—Worldwide, (2012).

F9RS38, UniProtKB/TrEMBL Accession No. F9RS38_9VIBR, Nov. 28, 2012 [online]. [Retrieved on Feb. 3, 2015]. Retrieved from the internet URL: http://www.uniprot.org/uniprot/F9RS38.txt?version=5>.

Farrell, C., et al., "Population Pharmacokinetics of Farletuzumab, a Humanized Monoclonal Antibody Against Folate Receptor Alpha, in Epithelial Ovarian Cancer," Cancer Chemotherapy and Pharmacology 70(5):727-734, Springer Verlag, Germany (2012).

Ferrini, S., et al., "Bispecific Monoclonal Antibodies Directed to CD16 and to a Tumor-associated Antigen Induce Target-cell Lysis by Resting NK Cells and by a Subset of NK Clones," International Journal of Cancer 48(2):227-233, Wiley-Liss, United States (1991).

Ferrini, S., et al., "Retargeting of T-cell-receptor Gamma/delta+ Lymphocytes Against Tumor Cells by Bispecific Monoclonal Antibodies. Induction of Cytolytic Activity and Lymphokine Production," International Journal of Cancer 4:53-55, Wiley-Liss, United States (1989).

Figini, M., et al., "Conversion of Murine Antibodies to Human Antibodies and their Optimization for Ovarian Cancer Therapy Targeted to the Folate Receptor," Cancer Immunology, Immunotherapy 58(4):531-546, Springer Verlag, Germany (2009).

Figini, M., et al., "Panning Phage Antibody Libraries on Cells: Isolation of Human Fab Fragments Against Ovarian Carcinoma Using Guided Selection," Cancer Research 58(5):991-996, American Association for Cancer Research, United States (1998).

Franklin, W.A., et al., "New Anti-lung-cancer Antibody Cluster 12 Reacts with Human Folate Receptors Present on Adenocarcinoma," International Journal of Cancer. Supplement 8:89-95, Wiley-Liss, United States (1994).

Gould, H.J., et al., "Comparison of IgE and IgG Antibody-dependent Cytotoxicity in Vitro and in a SCID Mouse Xenograft Model of Ovarian Carcinoma," European Journal of Immunology 29(11):3527-3537, Wiley-VCH, Germany (1999).

Green, B. and Duffull, S.B., "What is the Best Size Descriptor to Use for Pharmacokinetic Studies in the Obese," British Journal of Clinical Pharmacology 58(2):119-133, Blackwell Publishing Ltd., England (2004).

H0DED6, UniProtKB/TrEMBL Accession No. H0DED6_9STAP, Nov. 28, 2012 [online]. [Retrieved on Feb. 3, 2015]. Retrieved from the internet URL: http://www.uniprot.org/uniprot/H0DED6.txt?version=5>.

Hartmann, L.C., et al., "Folate Receptor Overexpression is Associated with Poor Outcome in Breast Cancer," International Journal of Cancer 121(5):938-942, Wiley-Liss, United States (2007).

International Preliminary Report on Patentability for International Application No. PCT/US2012/031544, International Bureau of WIPO, Switzerland, mailed on Oct. 1, 2013, 6 pages.

International Preliminary Report on Patentability for International Application No. PCT/US2012/032155, International Bureau of WIPO, Switzerland, mailed on Oct. 17, 2013, 7 pages.

International Search Report for International Application No. PCT/US14/53512, ISA/US, Alexandria, Virginia, United States, mailed on Feb. 24, 2015, 6 pages.

International Search Report for International Application No. PCT/US2011/026079, ISA/US, Alexandria, Virginia, United States, mailed on Aug. 2, 2011, 7 pages.

International Search Report for International Application No. PCT/US2012/031544, ISA/US, Alexandria, Virginia, United States, mailed on Sep. 21, 2012, 3 pages.

International Search Report for International Application No. PCT/US2012/032155, ISA/US, Alexandria, Virginia, United States, mailed on Jul. 6, 2012, 3 pages.

International Search Report for International Application No. PCT/US2013/057682, ISA/US, Alexandria, Virginia, United States, mailed on Jan. 10, 2014, 5 pages.

International Search Report for International Application No. PCT/US2014/037911, ISA/US, Alexandria, Virginia, United States, mailed on Oct. 31, 2014, 4 pages.

(56) References Cited

OTHER PUBLICATIONS

International Search Report for International Application No. PCT/US2014/059716, ISA/US, Alexandria, Virginia, United States, mailed on Jan. 21, 2015, 4 pages.
Jones, M.B., et al., "Rationale for Folate Receptor Alpha Targeted Therapy in "High Risk" Endometrial Carcinomas," International Journal of Cancer 123(7):1699-1703, Wiley-Liss, United States (2008).
Kalli, K.R., et al., "Folate Receptor Alpha as a Tumor Target in Epithelial Ovarian Cancer," Gynecologic Oncology 108(3):619-626, Academic Press, United States (2008).
Karagiannis, S.N., et al., "IgE-antibody-dependent Immunotherapy of Solid Tumors: Cytotoxic and Phagocytic Mechanisms of Eradication of Ovarian Cancer Cells," Journal of immunology 179(5):2832-2843, American Association of Immunologists, United States (2007).
Konner, J.A., et al., "Farletuzumab, a Humanized Monoclonal Antibody against Folate Receptor Alpha, in Epithelial Ovarian Cancer: A Phase I Study," Clinical Cancer Research 16(21):5288-5295, The Association, United States (2010).
Ladd, S., et al., "Folate Receptor 1 Immunohistochemistry Repeatability and Stored Slide Antigen Stability," 38th Annual NSH Symposium—Vancouver, BC Canada (Sep. 28-Oct. 3, 2012), Abstract, 1 page, National Society for Histotechnology, Canada (2012).
Ladd, S., et al., "Folate Receptor 1 Immunohistochemistry Repeatability and Stored Slide Antigen Stability," 38th Annual NSH Symposium—Vancouver, BC Canada (Sep. 28-Oct. 3, 2012), Poster P-38, National Society for Histotechnology, Canada (Sep. 28, 2012).
Lawson, N. and Scorer, P., "Evaluation of Antibody to Folate Receptor-alpha (FR-alpha)," published online on May 31, 2010, accessed at http://www.leicabiosystems.com/pathologyleaders/evaluation-of-antibody-to-folate-receptor-alpha-fr-°/CE°B1/, accessed on Oct. 27, 2014 (1 page).
Lim, J., et al., "C5A929 (C5A929_BURGB) Unreviewed, UniProtKB/TrEMBL", UniProt, 4 pages, last modified Apr. 18, 2012, accessed at <http://www.uniprot.org/uniprot/C5A929>.
Lu, Y. and Low, P.S., "Immunotherapy of Folate Receptor-expressing Tumors: Review of Recent Advances and Future Prospects," Journal of Controlled Release 91(1-2):17-29, Elsevier Science Publishers, Netherlands (2003).
Mantovani, L.T., et al., "Folate Binding Protein Distribution in Normal Tissues and Biological Fluids from Ovarian Carcinoma Patients as Detected by the Monoclonal Antibodies MOv18 and MOv19," European Journal of Cancer 30A(3):363-369, Pergamon Press, England (1994).
Melani, C., et al., "Targeting of Interleukin 2 to Human Ovarian Carcinoma by Fusion with a Single-chain Fv of Antifolate Receptor Antibody," Cancer Research 58(18):4146-4154, American Association for Cancer Research, United States (1998).
Mezzanzanica, D., et al., "Human Ovarian Carcinoma Lysis by Cytotoxic T Ccells Targeted by Bispecific Monoclonal Antibodies: Analysis of the Antibody Components," International Journal of Cancer 41(4):609-615, Wiley-Liss, United States (1988).
Miotti, S., et al., "Characterization of Human Ovarian Carcinoma-associated Antigens Defined by Novel Monoclonal Antibodies with Tumor-restricted Specificity," International Journal of Cancer 39(3):297-303, Wiley-Liss, United States (1987).
NCL-L-FRalpha, "Novocastra Liquid Mouse Monoclonal Antibody Folate Receptor Alpha: Product Code: NCL-L-FRalpha," 40 pages, Leica Biosystems Newcastle Ltd, England (2009).
Nishiyama, T., et al., "A9SZW6 (A9SZW6_PHYPA) Unreviewed, UniProtKB/TrEMBL," UniProt, 3 pages, last modified Sep. 21, 2011, accessed at <http://www.uniprot.org/uniprot/A9SZW6>.
Nutt, J.E., et al., "The Role of Folate Receptor Alpha (FRalpha) in the Response of Malignant Pleural Mesothelioma to Pemetrexed-containing Chemotherapy," British Journal of Cancer 102(3):553-560, Nature Publishing Group, England (2010).

O'Shannessy, D.J., et al., "Characterization of the Human Folate Receptor Alpha via Novel Antibody-based Probes," Oncotarget 2(12):1227-1243, Impact Journals, United States (2011).
Paganelli, G., et al., "Two-step Tumour Targetting in Ovarian Cancer Patients Using Biotinylated Monoclonal Antibodies and Radioactive Streptavidin," European Journal of Nuclear Medicine 19(5):322-329, Springer Verlag, Germany (1992).
Paul, W.E., "Structure and Function of Immunoglobulins," in *Fundamental Immunology*, Third Edition, pp. 292-295, Raven Press, New York, United States (1993).
Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).
R5I4W9, UniProtKB/TrEMBL Accession No. R5I4W9_9FIRM, Jul. 24, 2013 [online]. [Retrieved on Feb. 3, 2015]. Retrieved from the internet <URL:http://www.uniprot.org/uniprot/R5I4W9.txt?version=1>.
Roberts. S.J., et al., "Role of Individual N-linked Glycosylation Sites in the Function and Intracellular Transport of the Human Alpha Folate Receptor," Archives of Biochemistry and Biophysics 351(2):227-235, Academic Press, United States (1998).
Rudikoff, S., et al., "Single Amino Acid Substitution Altering Antigen-Binding Specificity," Proceedings of the National Academy of Sciences 79(6):1979-1983, The National Academy of Sciences, United States (1982).
Scorer, P., et al., "A Full Immunohistochemical Evaluation of a Novel Monoclonal Antibody to Folate Receptor—alpha (FR-alpha)," reAGENTS 3:8-12, Leica Biosystems Newcastle Ltd., England (2010).
Search Report and Written Opinion for Singaporean Patent Application No. 2013070040, Intellectual Property Office of Singapore, Singapore, mailed on Dec. 30, 2014, 17 pages.
Singh, R. and Erickson, H.K., "Antibody-cytotoxic Agent Conjugates: Preparation and Characterization," Methods in Molecular Biology 525:445-467, Humana Press, United States (2009).
Smith, A.E., et al., "A Novel Monoclonal Antibody for Detection of Folate Receptor Alpha in Paraffin-embedded Tissues," Hybridoma 26(5):281-288, Mary Ann Liebert, Inc., United States (2007).
Smith-Jones, P.M., et al., "Preclinical Radioimmunotargeting of Folate Receptor Alpha Using the Monoclonal Antibody Conjugate DOTO-MORAb-003," Nuclear Medicine and Biology 35(3):343-351, Elsevier, United States (2008).
Supplementary European Search Report and European Search Opinion for EP Application No. EP11748067, The Hague, Netherlands, mailed on Jun. 26, 2013.
Supplementary Partial European Search Report for EP Application No. EP12764885, The Hague, Netherlands, mailed on Nov. 21, 2014.
Testa, N., et al., "A Method for Quantifying Soluble Folate Receptor 1 in IMGN853 0401 Clinical Trial Patients," 2013 AACR Annual Meeting—Washington, DC (Apr. 6-10, 2013), Abstract #3503 Poster, American Association of Cancer Research, United States (Apr. 6, 2013).
Testa, N., et al., "A Method for Quantifying Soluble Folate Receptor 1 in IMGN8530401 Clinical Trial Patients," 2013 AACR Annual Meeting —Washington, DC (Apr. 6-10, 2013), Abstract #3503, 1 Page, American Association of Cancer Research, United States (submitted Nov. 15, 2012).
Tolcher, A., et al., "A Novel Dosing Strategy on Plasma Levels of CanAg in a Phase II Study of IMGN242 (huC242-DM4) in Gastric Cancer," 20th EORTC-NCI-AACR Symposium: Abstract #514, Oct. 21-24, 2008, Geneva, Switzerland (2008).
Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).
Van Dam, G.M., et al., "Intraoperative Tumor-specific Fluorescence Imaging in Ovarian Cancer by Folate Receptor-alpha Targeting: First in-human Results," Nature Medicine 17(10):1315-1319, Nature Publishing Company, United States (2011).

(56) References Cited

OTHER PUBLICATIONS

White, A.J., et al., "Efficacy and safety of farletuzumab, a humanized monoclonal antibody to folate receptor alpha, in platinum-sensitive relapsed ovarian cancer subjects: Final data from a multicenter phase II study," Journal of Clinical Oncology 28(15), Supp. Suppl. 1. Abstract Number: 5001(1 pages), American Society of Clinical Oncology, United States (2010).

Whiteman, K.R., et al., "Anti-tumor Activity and Pharmacokinetics of the Anti-FOLR-1-maytansinoid Conjugate IMGN853 is Maintained Over a Wide Range of Maytansinoid-to-antibody Ratios," 103rd Annual AACR Meeting—Chicago, IL (Mar. 31-Apr. 4, 2012), Abstract #4628, 1 page, American Association for Cancer Research, United States (2012).

Whiteman, K.R., et al., "Anti-tumor Activity and Pharmacokinetics of the Anti-FOLR-1-maytansinoid Conjugate IMGN853 is Maintained Over a Wide Range of Maytansinoid-to-antibody Ratios," 103rd Annual AACR Meeting—Chicago, IL (Mar. 31-Apr. 4, 2012), Abstract #4628 Poster, American Association for Cancer Research, United States (Mar. 31, 2012).

Whiteman, K.R., et al., "Preclinical Evaluation of IMGN853, an Anti-FOLR1 Antibody-maytansinoid Conjugate, as a Potential Therapeutic for Ovarian Cancer," 102nd Annual AACR Meeting—Orlando, FL (Apr. 2-6, 2011), Abstract 1760, 1 Page, American Association for Cancer Research, United States (distributed in print Mar. 8, 2011; available online Feb. 25, 2011).

Whiteman, K.R., et al., "Preclinical Evaluation of IMGN853, An Anti-FOLR1 Antibody-maytansinoid Conjugate, as a Potential Therapeutic for Ovarian Cancer," 102nd Annual AACR Meeting—Orlando, FL (Apr. 2-6, 2011), Abstract 1760 Poster, American Association for Cancer Research, United States (Apr. 2, 2011).

Widdison, W.C., et al., "Semisynthetic Maytansine Analogues for the Targeted Treatment of Cancer," Journal of Medicinal Chemistry 49 (14):4392-4408, American Chemical Society, United States (2006).

Yan, Kunimasa, et al., "N-Linked Glycosylation Is Critical for the Plasma Membrane Localization of Nephrin," Journal of the American Society of Nephrology 13: 1385-1389, American Society of Nephrology, United States (2002).

Yuan, Y., et al., "Expression of the Folate Receptor Genes FOLR1 and FOLR3 Differentiates Ovarian Carcinoma from Breast Carcinoma and Malignant Mesothelioma in Serous Effusions," Human Pathology 40(10):1453-1460, W B Saunders, United States (2009).

Zacchetti, A., et al., "(177)Lu- Labeled MOv18 as Compared to (131)I- or (90)Y-labeled MOv18 has the Better Therapeutic Effect in Eradication of Alpha Folate Receptor-expressing Tumor Xenografts," Nuclear Medicine and Biology 36(7):759-770, Elsevier, United States (2009).

NCT01609556, "A Phase 1, First-in-Human Study to Evaluate the Safety, Tolerability, Pharmacokinetics and Pharmacodynamics of IMGN853 in Adults with Ovarian Cancer and Other FOLR1-Positive Solid Tumors" (2012), ClinicalTrials.gov archive, accessed at https://clinicaltrials.gov/archive/NCT01609556/2012_05_31, on Feb. 12, 2016, 6 pages.

NCT01609556, "First-in-Human Study to Evaluate the Safety, Tolerability, Pharmacokinetics and Pharmacodynamics of IMGN853 in Adults with Ovarian Cancer and Other FOLR1-Positive Solid Tumors (IMGN-0401)" (2012), accessed at https://clinicaltrials.gov/ct2/show/NCT01609556?term=IMGN853&rank=3, on Feb. 12, 2016, 4 pages.

NCT02631876, "PH2 Study of IMGC853 vs Investigator's Choice of Chemo in Adults with Fra+ Adv. EOC, Primary Peritoneal or Primary Fallopian Tube Cancer" (2015), accessed at https://clinicaltrials.gov/ct2/show/study/NCT02631876?term=mirvetuximab+soravtansine, on Feb. 12, 2016, 3 pages.

Non-Final Office Action mailed Aug. 6, 2015, in U.S. Appl. No. 14/276,917, Running, K., et al., filed May 13, 2014.

Co-pending, U.S. Appl. No. 14/921,596 inventors Carrigan, C.N., et al., filed Oct. 23, 2015 (Not Yet Published).

Co-pending, U.S. Appl. No. 14/946,423 inventors AB, O., et al., filed Nov. 19, 2015 (Not Yet Published).

Co-pending, U.S. Appl. No. 14/970,433 inventors AB, O., et al., filed Dec. 15, 2015 (Not Yet Published).

Co-pending, U.S. Appl. No. 14/970,436 inventors AB, O., et al., filed Dec. 15, 2015 (Not Yet Published).

Final Office Action mailed Mar. 24, 2016, in U.S. Appl. No. 14/276,917, Running, K., et al., filed May 13, 2014.

Non-Final Office Action mailed Apr. 19, 2016, in U.S. Appl. No. 14/921,596, Carrigan, C., et al., filed Oct. 23, 2015.

Final Office Action mailed Jun. 3, 2015, in U.S. Appl. No. 14/015,653, Carrigan, C., et al., filed Aug. 30, 2013.

Non-Final Office Action mailed Dec. 24, 2014, in U.S. Appl. No. 14/015,653, Carrigan, C., et al., filed Aug. 30, 2013.

Non-Final Office Action mailed Apr. 28, 2016, in U.S. Appl. No. 14/819,209, AB, O., et al., filed Aug. 5, 2015.

Kurkjian, C., et al., "A phase I, first-in-human study to evaluate the safety, pharmacokinetics (PK), and pharmacodynamics (PD) of IMGN853 in patients (Pts) with epithelial ovarian cancer (EOC) and other FOLR1-positive solid tumors," 2013 ASCO Annual Meeting, Poster, 4 pages (Jun. 2013).

Kurkjian, C., et al., "A phase I, first-in-human study to evaluate the safety, pharmacokinetics (PK), and pharmacodynamics (PD) of IMGN853 in patients (Pts) with epithelial ovarian cancer (EOC) and other FOLR1-positive solid tumors," Journal of Clinical Oncology 31:Suppl. Abstract 2573, 2 pages, American Society of Clinical Oncology, United States (2013).

Moore, K.N., et al., "Relationship of pharmacokinetics (PK), toxicity, and initial evidence of clinical activity with IMGN853, a folate receptor alpha (Fra) targeting antibody drug conjugate in patients (Pts) with epithelial ovarian cancer (EOC) and other Fra-positive solid tumors," 2014 ASCO Annual Meeting, Abstract 5571, 3 pages (2014).

Moore, K.N., et al., "Relationship of pharmacokinetics (PK), toxicity, and initial evidence of clinical activity with IMGN853, a folate receptor alpha (Fra) targeting antibody drug conjugate in patients (Pts) with epithelial ovarian cancer (EOC) and other Fra-positive solid tumors," 2014 ASCO Annual Meeting, Poster, 5 pages (2014).

Ponte, J.F., et al., "Development of Modified Dosing Approaches to Achieve Specific Pharmacokinetic (PK) Objectives in the First-in-Human Phase I Clinical Trial of IMGN853, a Folate Receptor alpha-Targeting Antibody Drug Conjugate," 2014 AACD Annual Meeting, Poster, 5 pages (2014).

Ponte, J.F., et al., "Incorporation of Modified Dosing Approaches Based on Pharmacokinetic Analysis in a First in Human Phase I Clinical Trial of IMGN853, a Folate Receptor α-Targeting Antibody Drug Conjugate," 2014 AACR Annual Meeting, 2 pages (2014).

Gershoni, J.M., et al., "Epitop Mapping the First Step in Developing Epitope-Based Vaccines," Biodrugs 21(3):145-156, Adis Data Information by, Israel (2007).

Winkler, K., et al., "Changing the Antigen Binding Specificity by Single Point Mutations of an Anti-p24 (HIV-1) Antibody," Journal Immunology 165:4505-4514, American Association of Immunologists, United States (2000).

Co-pending, U.S. Appl. No. 15/095,963, Lutz, R. J., et al., filed Apr. 11, 2016 (Not Published).

Non-Final Office Action mailed Nov. 8, 2012, in U.S. Appl. No. 13/033,723, Olga, A.B., et al., filed Feb. 24, 2011.

Final Office Action mailed May 1, 2013, in U.S. Appl. No. 13/033,723, Olga, A.B., et al., filed Feb. 24, 2011.

Non-Final Office Action mailed Dec. 31, 2014, in U.S. Appl. No. 13/800,835, Olga, A.B., et al., filed Mar. 13, 2013.

Non-Final Office Action mailed Jan. 21, 2016, in U.S. Appl. No. 14/970,433, Ab, Olga., et al., filed Dec. 15, 2015.

Final Office Action mailed Oct. 26, 2016, in U.S. Appl. No. 14/921,596, Carrigan, C., et al., filed Oct. 23, 2015.

Non-Final Office Action mailed Aug. 25, 2016, in U.S. Appl. No. 14/276,917, Running, K., et al., filed May 13, 2014.

Final Office Action mailed Sep. 23, 2016, in U.S. Appl. No. 14/819,209, Ab, O., et al., filed Aug. 5, 2015.

Co-pending, U.S. Appl. No. 15/388,873, Running, et al., filed Dec. 22, 2016 (Not Published).

\* cited by examiner

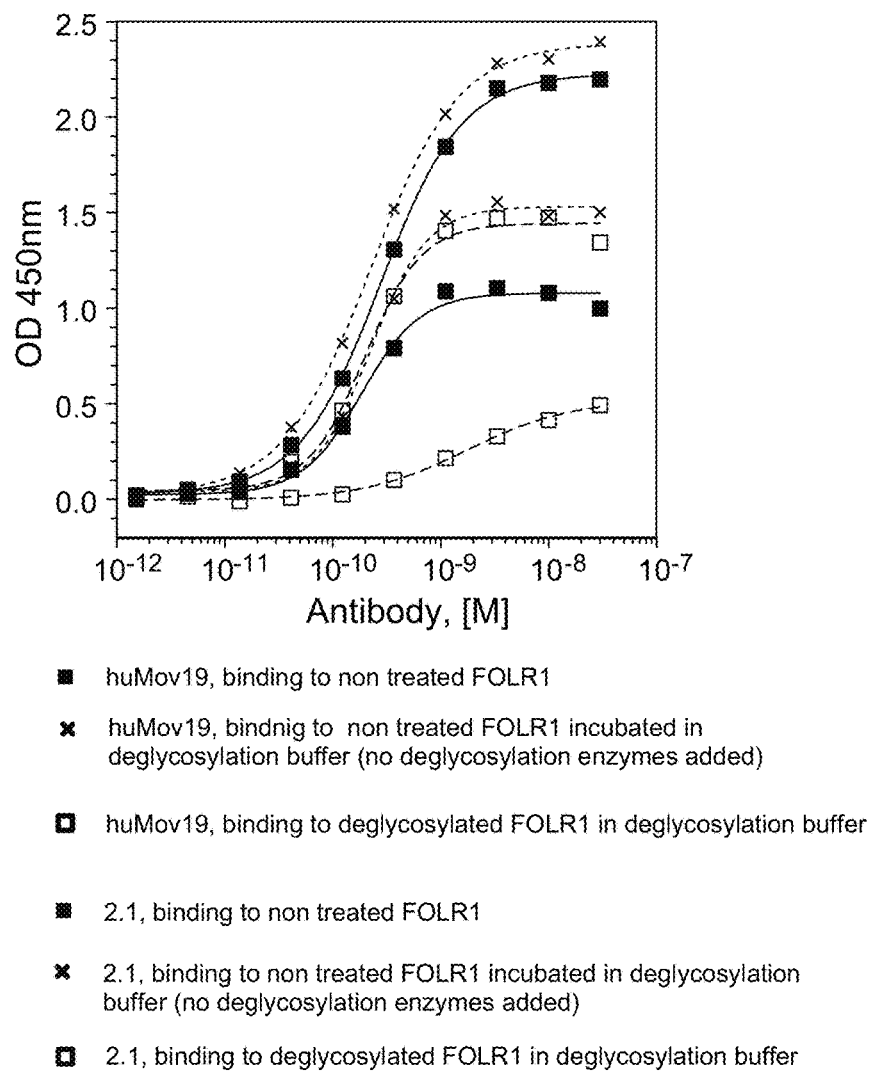

- ■ huMov19, binding to non treated FOLR1
- ✖ huMov19, bindnig to non treated FOLR1 incubated in deglycosylation buffer (no deglycosylation enzymes added)
- ▫ huMov19, binding to deglycosylated FOLR1 in deglycosylation buffer

- ■ 2.1, binding to non treated FOLR1
- ✖ 2.1, binding to non treated FOLR1 incubated in deglycosylation buffer (no deglycosylation enzymes added)
- ▫ 2.1, binding to deglycosylated FOLR1 in deglycosylation buffer

FIG. 7

Resurfacing of FRIHC2-1

A

| FRIHC2-1- V$_L$ | | | |
|---|---|---|---|
| Kabat position | Murine residue | Human v1.0 residue | Human v1.01 residue |
| 1 | D | D | D |
| 3 | V | V | V |
| 7 | T | *S* | *S* |
| 9 | L | L | L |
| 15 | I | *L* | *L* |
| 17 | D | *Q* | *Q* |
| 18 | Q | *P* | *P* |
| 40 | P | P | P |
| 41 | G | G | G |
| 42 | K | K | K |
| 45 | Q | *R* | *R* |
| 57 | G | G | G |
| 60 | D | D | D |
| 67 | S | S | S |
| 77 | R | R | R |
| 81 | E | E | E |
| 100 | G | *Q* | *Q* |
| 103 | K | K | K |
| 107 | K | K | K |
| 108 | R | R | R |
| 24 | K | *R* | K |
| 27 | K | *R* | K |

B

| FRIHC2-1- V$_H$ | | |
|---|---|---|
| Kabat position | Murine residue | Human residue |
| 1 | Q | Q |
| 3 | Q | Q |
| 5 | Q | *V* |
| 9 | P | *A* |
| 11 | L | *V* |
| 13 | K | K |
| 14 | P | P |
| 19 | R | *K* |
| 23 | K | K |
| 28 | T | T |
| 41 | P | P |
| 42 | G | G |
| 43 | Q | Q |
| 61 | E | *Q* |
| 62 | K | K |
| 64 | K | *Q* |
| 65 | A | *G* |
| 73 | K | K |
| 74 | S | S |
| 82b | S | S |
| 84 | S | S |
| 85 | E | E |
| 105 | Q | Q |
| 112 | S | S |

FIG. 9

Resurfacing alignments

A
muFRIHC2-1 VL          1  DVVLTQTPLSLPVNIGQQASISCKSKSSLLNSDGFTYLDWYLQKPGQSPQLLIYLVSNWFS
huFRIHC2-1 VLv1.0         ----------S-------L-QP----------------------------R--R------
huFRIHC2-1 VLv1.01        ----------S-------L-QP----------------------------R--R------ muFRIHC2-1 VL          62 GVPDRFSGSGSGTDFTLKISRVEAEDLGVYYCFQSNYLPLTFGGGTKLEIKR
huFRIHC2-1 VLv1.0         -------------------------------------------Q--------
huFRIHC2-1 VLv1.01        -------------------------------------------Q--------

B
muFRIHC2-1 VH          1  QVQLQQSGPELVKPGASVRISCKASGYTFTNSYIHWVKKRPGQGLEWIGWIYPESLNTQYN
huFRIHC2-1 VH             -------------------------A--V-------------K----------------- muFRIHC2-1 VH          62 EKFKAKATLTADKSSSTSYMQLSSLTSEDSAVYFCARRGIYYYSPYYALDHWGQGASVTVSS
huFRIHC2-1 VH             -Q---QG-----------------------------------------------------

FIG. 10

CDR-grafting of FRIHC2-1

A

| FRIHC2-1- V_L | | | |
|---|---|---|---|
| Kabat position | Murine residue | Human (CDR-graft) v1.0 residue | Human (CDR-graft) v1.01 residue |
| 2 | V | I | I |
| 4 | L | M | M |
| 12 | P | S | S |
| 14 | N | T | T |
| 15 | I | P | P |
| 17 | D | Q | Q |
| 18 | Q | P | P |
| 83 | L | V | V |
| 100 | G | Q | Q |
| 24 | K | R | K |
| 27 | K | R | K |

B

| FRIHC2-1- V_H | | |
|---|---|---|
| Kabat position | Murine residue | Human (CDR-graft) residue |
| 5 | Q | V |
| 9 | P | A |
| 11 | L | V |
| 12 | V | K |
| 19 | R | K |
| 20 | I | V |
| 38 | K | R |
| 39 | K | Q |
| 40 | R | A |
| 48 | I | M |
| 66 | K | R |
| 67 | A | V |
| 69 | L | M |
| 71 | A | R |
| 73 | K | T |
| 75 | S | I |
| 78 | S | A |
| 81 | Q | E |
| 82b | S | R |
| 83 | T | R |
| 85 | E | D |
| 87 | S | T |
| 91 | F | Y |
| 107 | A | T |
| 108 | S | L |

FIG. 11

CDR grafting alignments

A

```
              1                                                              61
muFRIHC2-1 VL     DVVLTQTPLSLPVNIGDQASISCKSSKSLLNSDGFTYLDWYLQKPGQSPQLLIYLVSNHFS
huFRIHC2-1 VLGv1.0    --I-M-----------------S-TP-QP------------R----R-------------
huFRIHC2-1 VLGv1.01   --I-M-----------------S-TP-QP------------R----R-------------

62                                                             113
muFRIHC2-1 VL     GVPDRFSGSGSGTDFTLKISRVEAEDLGVYYCFQSNYLPLTFGGGTKLEIKR
huFRIHC2-1 VLGv1.0    ----------------------------V---------Q------------
huFRIHC2-1 VLGv1.01   ----------------------------V---------Q------------
```

B

```
              1                                                              61
muFRIHC2-1 VH     QVQLQQSGPELVKPGASVRISCKASGYTFTNSYIHWVKKRPGQGLEWIGMIYPESLNTQYN
huFRIHC2-1 VHG        -----V------A-VK------KV-------------RQA----M---------------

62                                                             122
muFRIHC2-1 VH     EKFKAKATLTADKSSSTSYMQLSSLTSEDSAVYFCARRGIYYYSPYALDHWGQGASVTVSS
huFRIHC2-1 VHG        -RV-M--R-T-I---A--E---R--R--D-T---Y-----------------TL------
```

FIG. 12

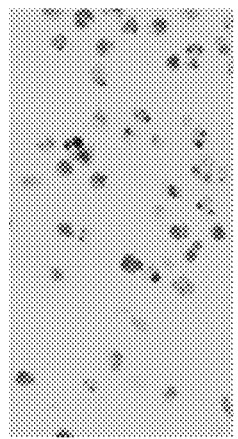
FIG. 14A
Fallopian Tube Positive
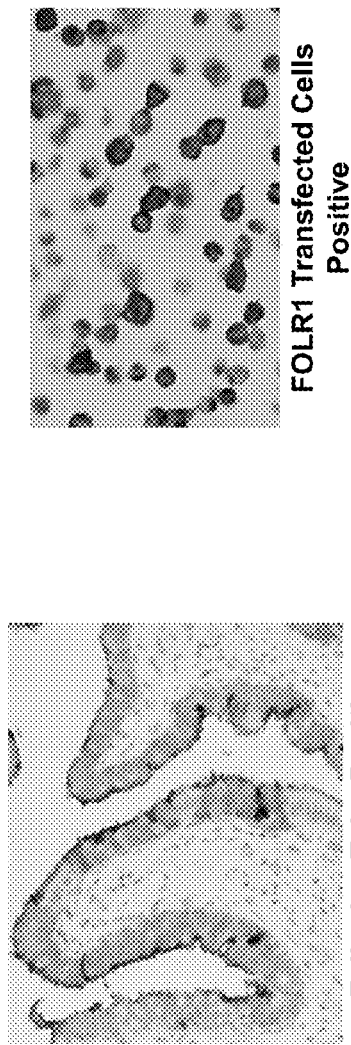
FIG. 14B
FOLR1 Transfected Cells Positive
FIG. 14C
Non-Transfected Cells Unstained
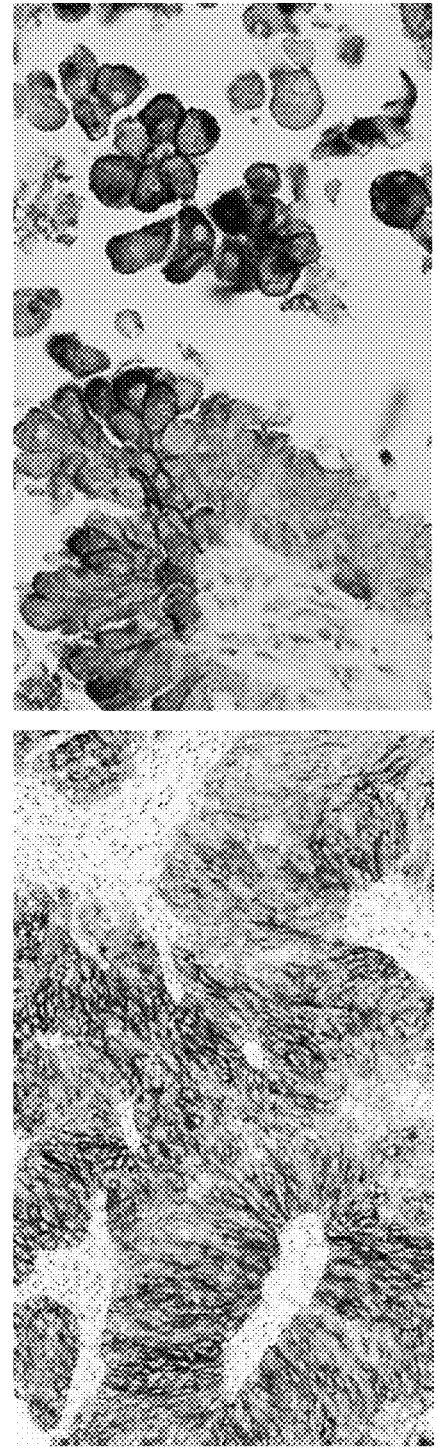
FIG. 15A
Ovarian Cancer
FIG. 15B
Adenocarcinoma of the Lung

SEQUENCE LISTING

```
<160> NUMBER OF SEQ ID NOS: 75

<210> SEQ ID NO 1
<211> LENGTH: 257
<212> TYPE: PRT
<213> ORGANISM: Homo sapiens

<400> SEQUENCE: 1

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 2
<211> LENGTH: 771
```

```
<212> TYPE: DNA
<213> ORGANISM: Homo sapiens

<400> SEQUENCE: 2
atggctcagc ggatgacaac acagctgctg ctccttctag tgtgggtggc tgtagtaggg      60
gaggctcaga caaggattgc atgggccagg actgagcttc tcaatgtctg catgaacgcc     120
aagcaccaca aggaaaagcc aggccccgag acaagttgc atgagcagtg tcgaccctgg      180
aggaagaatg cctgctgttc taccaacacc agccaggaag cccataagga tgtttcctac     240
ctatatagat tcaactggaa ccactgtgga gagatggcac ctgcctgcaa acggcatttc     300
atccaggaca cctgcctcta cgagtgctcc cccaacttgg ggccctggat ccagcaggtg     360
gatcagagct ggcgcaaaga gcgggtactg aacgtgcccc tgtgcaaaga ggactgtgag     420
caatggtggg aagattgtcg cacctcctac acctgcaaga gcaactggca aagggctgg     480
aactggactt cagggtttaa caagtgcgca gtgggagctg cctgccaacc tttccatttc     540
tacttcccca cacccactgt tctgtgcaat gaaatctgga ctcactccta caaggtcagc     600
aactacagcc gagggagtgg ccgctgcatc cagatgtggt cgacccagc ccagggcaac      660
cccaatgagg aggtggcgag gttctatgct gcagccatga gtggggctgg gccctgggca     720
gcctggcctt tcctgcttag cctggcccta atgctgctgt ggctgctcag c              771
```

```
<210> SEQ ID NO 3
<211> LENGTH: 5
<212> TYPE: PRT
<213> ORGANISM: Artificial Sequence
<220> FEATURE:
<223> OTHER INFORMATION: muFRIHC2-1 VH-CDR1

<400> SEQUENCE: 3

Asn Ser Tyr Ile His
1               5

<210> SEQ ID NO 4
<211> LENGTH: 17
<212> TYPE: PRT
<213> ORGANISM: Artificial Sequence
<220> FEATURE:
<223> OTHER INFORMATION: muFRIHC2-1 VH-CDR2

<400> SEQUENCE: 4

Trp Ile Tyr Pro Glu Ser Leu Asn Thr Gln Tyr Asn Glu Lys Phe Lys
1               5                   10                  15

Ala

<210> SEQ ID NO 5
<211> LENGTH: 13
<212> TYPE: PRT
<213> ORGANISM: Artificial Sequence
<220> FEATURE:
<223> OTHER INFORMATION: muFRIHC2-1 VH-CDR3

<400> SEQUENCE: 5

Arg Gly Ile Tyr Tyr Tyr Ser Pro Tyr Ala Leu Asp His
1               5                   10

<210> SEQ ID NO 6
<211> LENGTH: 16
<212> TYPE: PRT
<213> ORGANISM: Artificial Sequence
<220> FEATURE:
<223> OTHER INFORMATION: muFRIHC2-1 VL-CDR1
```

```
<400> SEQUENCE: 6

Lys Ser Ser Lys Ser Leu Leu Asn Ser Asp Gly Phe Thr Tyr Leu Asp
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: muFRIHC2-1 VL-CDR2

<400> SEQUENCE: 7

Leu Val Ser Asn His Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: muFRIHC2-1 VL-CDR3

<400> SEQUENCE: 8

Phe Gln Ser Asn Tyr Leu Pro Leu Thr
1               5

<210> SEQ ID NO 9
<211> LENGTH: 5
<212> TYPE: PRT
<213> ORGANISM: Artificial Sequence
<220> FEATURE:
<223> OTHER INFORMATION: muFRIHC5-7 VH-CDR1

<400> SEQUENCE: 9

Asn Tyr Tyr Ile His
1               5

<210> SEQ ID NO 10
<211> LENGTH: 17
<212> TYPE: PRT
<213> ORGANISM: Artificial Sequence
<220> FEATURE:
<223> OTHER INFORMATION: muFRIHC5-7 VH-CDR2

<400> SEQUENCE: 10

Trp Ile Tyr Pro Gly Ser Phe Asn Val Glu Tyr Asn Glu Lys Phe Lys
1               5                   10                  15

Ala

<210> SEQ ID NO 11
<211> LENGTH: 13
<212> TYPE: PRT
<213> ORGANISM: Artificial Sequence
<220> FEATURE:
<223> OTHER INFORMATION: muFRIHC5-7 VH-CDR3

<400> SEQUENCE: 11

Arg Gly Ile Tyr Phe Tyr Ser Pro Tyr Ala Leu Asp Tyr
1               5                   10

<210> SEQ ID NO 12
<211> LENGTH: 16
<212> TYPE: PRT
<213> ORGANISM: Artificial Sequence
<220> FEATURE:
```

<223> OTHER INFORMATION: muFRIHC5-7 VL-CDR1

<400> SEQUENCE: 12

Lys Ser Thr Glu Ser Leu Leu Asn Ser Asp Gly Phe Thr Tyr Leu Asp
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: muFRIHC5-7 VL-CDR2

<400> SEQUENCE: 13

Leu Val Ser Asn His Phe Ser
1               5

<210> SEQ ID NO 14
<211> LENGTH: 9
<212> TYPE: PRT
<213> ORGANISM: Artificial Sequence
<220> FEATURE:
<223> OTHER INFORMATION: muFRIHC5-7 VL-CDR3

<400> SEQUENCE: 14

Phe Gln Ser Asn Tyr Leu Pro Leu Thr
1               5

<210> SEQ ID NO 15
<211> LENGTH: 5
<212> TYPE: PRT
<213> ORGANISM: Artificial Sequence
<220> FEATURE:
<223> OTHER INFORMATION: muFRIHC9-20 VH-CDR1

<400> SEQUENCE: 15

Asn Tyr Tyr Ile His
1               5

<210> SEQ ID NO 16
<211> LENGTH: 17
<212> TYPE: PRT
<213> ORGANISM: Artificial Sequence
<220> FEATURE:
<223> OTHER INFORMATION: muFRIHC9-20 VH-CDR2

<400> SEQUENCE: 16

Trp Ile Tyr Pro Glu Asn Val Asn Val Arg Tyr Asn Asp Lys Phe Lys
1               5                   10                  15

Ala

<210> SEQ ID NO 17
<211> LENGTH: 13
<212> TYPE: PRT
<213> ORGANISM: Artificial Sequence
<220> FEATURE:
<223> OTHER INFORMATION: muFRIHC9-20 VH-CDR3

<400> SEQUENCE: 17

Arg Gly Ile Tyr Tyr Tyr Ser Pro Tyr Ala Met Asp Tyr
1               5                   10

<210> SEQ ID NO 18
<211> LENGTH: 16
<212> TYPE: PRT
<213> ORGANISM: Artificial Sequence

```
<220> FEATURE:
<223> OTHER INFORMATION: muFRIHC9-20 VL-CDR1

<400> SEQUENCE: 18

Lys Ser Thr Lys Ser Leu Leu Asn Ser Asp Gly Phe Thr Tyr Leu Asp
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: muFRIHC9-20 VL-CDR2

<400> SEQUENCE: 19

Leu Val Ser Asn His Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: muFRIHC9-20 VL-CDR3

<400> SEQUENCE: 20

Phe Gln Ser Asn Tyr Leu Pro Leu Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Composite VH-CDR1
<220> FEATURE:
<221> NAME/KEY: misc_feature
<222> LOCATION: (2)..(2)
<223> OTHER INFORMATION: Xaa can be tyrosine or serine

<400> SEQUENCE: 21

Asn Xaa Tyr Ile His
1               5

<210> SEQ ID NO 22
<211> LENGTH: 17
<212> TYPE: PRT
<213> ORGANISM: Artificial Sequence
<220> FEATURE:
<223> OTHER INFORMATION: Composite VH-CDR2
<220> FEATURE:
<221> NAME/KEY: misc_feature
<222> LOCATION: (5)..(5)
<223> OTHER INFORMATION: Xaa can be glysine or glutamate
<220> FEATURE:
<221> NAME/KEY: misc_feature
<222> LOCATION: (6)..(6)
<223> OTHER INFORMATION: Xaa can be serine or arginine
<220> FEATURE:
<221> NAME/KEY: misc_feature
<222> LOCATION: (7)..(7)
<223> OTHER INFORMATION: Xaa can be phenylalanine or valine or leucine
<220> FEATURE:
<221> NAME/KEY: misc_feature
<222> LOCATION: (9)..(9)
<223> OTHER INFORMATION: Xaa can be valine or threonine
<220> FEATURE:
<221> NAME/KEY: misc_feature
<222> LOCATION: (10)..(10)
<223> OTHER INFORMATION: Xaa can be glutamate or arginine or glutamine
<220> FEATURE:
```

```
<221> NAME/KEY: misc_feature
<222> LOCATION: (13)..(13)
<223> OTHER INFORMATION: Xaa can be glutamate or aspartate

<400> SEQUENCE: 22

Trp Ile Tyr Pro Xaa Xaa Xaa Asn Xaa Xaa Tyr Asn Xaa Lys Phe Lys
1               5                   10                  15

Ala

<210> SEQ ID NO 23
<211> LENGTH: 13
<212> TYPE: PRT
<213> ORGANISM: Artificial Sequence
<220> FEATURE:
<223> OTHER INFORMATION: Composite VH-CDR3
<220> FEATURE:
<221> NAME/KEY: misc_feature
<222> LOCATION: (5)..(5)
<223> OTHER INFORMATION: Xaa can be phenylalanine or tyrosine
<220> FEATURE:
<221> NAME/KEY: misc_feature
<222> LOCATION: (11)..(11)
<223> OTHER INFORMATION: Xaa can be leucine or methionine
<220> FEATURE:
<221> NAME/KEY: misc_feature
<222> LOCATION: (13)..(13)
<223> OTHER INFORMATION: Xaa can be tyrosine or histidine

<400> SEQUENCE: 23

Arg Gly Ile Tyr Xaa Tyr Ser Pro Tyr Ala Xaa Asp Xaa
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Composite VL-CDR1
<220> FEATURE:
<221> NAME/KEY: misc_feature
<222> LOCATION: (3)..(3)
<223> OTHER INFORMATION: Xaa can be threonine or serine
<220> FEATURE:
<221> NAME/KEY: misc_feature
<222> LOCATION: (4)..(4)
<223> OTHER INFORMATION: Xaa can be lycine or glutamate

<400> SEQUENCE: 24

Lys Ser Xaa Xaa Ser Leu Leu Asn Ser Asp Gly Phe Thr Tyr Leu Asp
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Composite VL-CDR2

<400> SEQUENCE: 25

Leu Val Ser Asn His Phe Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Composite VL-CDR3

<400> SEQUENCE: 26
```

Phe Gln Ser Asn Tyr Leu Pro Leu Thr
1               5

<210> SEQ ID NO 27
<211> LENGTH: 122
<212> TYPE: PRT
<213> ORGANISM: Artificial Sequence
<220> FEATURE:
<223> OTHER INFORMATION: muFRIHC2-1 VH Chain

<400> SEQUENCE: 27

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asn Ser
                20                  25                  30

Tyr Ile His Trp Val Lys Lys Arg Pro Gly Gln Gly Leu Glu Trp Ile
            35                  40                  45

Gly Trp Ile Tyr Pro Glu Ser Leu Asn Thr Gln Tyr Asn Glu Lys Phe
        50                  55                  60

Lys Ala Lys Ala Thr Leu Thr Ala Asp Lys Ser Ser Thr Ser Tyr
65                  70                  75                  80

Met Gln Leu Ser Ser Leu Thr Ser Glu Asp Ser Ala Val Tyr Phe Cys
                85                  90                  95

Ala Arg Arg Gly Ile Tyr Tyr Tyr Ser Pro Tyr Ala Leu Asp His Trp
                100                 105                 110

Gly Gln Gly Ala Ser Val Thr Val Ser Ser
            115                 120

<210> SEQ ID NO 28
<211> LENGTH: 114
<212> TYPE: PRT
<213> ORGANISM: Artificial Sequence
<220> FEATURE:
<223> OTHER INFORMATION: muFRIHC2-1 VL Chain

<400> SEQUENCE: 28

Ser Asp Val Val Leu Thr Gln Thr Pro Leu Ser Leu Pro Val Asn Ile
1               5                   10                  15

Gly Asp Gln Ala Ser Ile Ser Cys Lys Ser Ser Lys Ser Leu Leu Asn
                20                  25                  30

Ser Asp Gly Phe Thr Tyr Leu Asp Trp Tyr Leu Gln Lys Pro Gly Gln
            35                  40                  45

Ser Pro Gln Leu Leu Ile Tyr Leu Val Ser Asn His Phe Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
                85                  90                  95

Ser Asn Tyr Leu Pro Leu Thr Phe Gly Gly Gly Thr Lys Leu Glu Ile
                100                 105                 110

Lys Arg

<210> SEQ ID NO 29
<211> LENGTH: 122
<212> TYPE: PRT
<213> ORGANISM: Artificial Sequence
<220> FEATURE:
<223> OTHER INFORMATION: muFRIHC5-7 VH Chain

<400> SEQUENCE: 29

Gln Val Gln Leu Gln Gln Ser Gly Pro Glu Val Val Lys Pro Gly Ala
1               5                   10                  15

Ser Val Arg Ile Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Phe Asn Val Tyr Asn Glu Lys Phe
    50                  55                  60

Lys Ala Lys Ala Thr Leu Thr Ala Asp Lys Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Arg Gly Ile Tyr Phe Tyr Ser Pro Tyr Ala Leu Asp Tyr Trp
            100                 105                 110

Gly Gln Gly Ala Ser Val Thr Val Ser Ser
            115                 120

<210> SEQ ID NO 30
<211> LENGTH: 114
<212> TYPE: PRT
<213> ORGANISM: Artificial Sequence
<220> FEATURE:
<223> OTHER INFORMATION: muFRIHC5-7 VL Chain

<400> SEQUENCE: 30

Ser Asp Val Val Leu Thr Gln Thr Pro Leu Ser Leu Pro Val Asn Ile
1               5                   10                  15

Gly Asp Gln Ala Ser Ile Ser Cys Lys Ser Thr Glu Ser Leu Leu Asn
            20                  25                  30

Ser Asp Gly Phe Thr Tyr Leu Asp Trp Tyr Leu Gln Lys Pro Gly Gln
        35                  40                  45

Ser Pro Gln Leu Leu Ile Tyr Leu Val Ser Asn His Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
                85                  90                  95

Ser Asn Tyr Leu Pro Leu Thr Phe Gly Gly Gly Thr Lys Leu Glu Val
            100                 105                 110

Lys Arg

<210> SEQ ID NO 31
<211> LENGTH: 122
<212> TYPE: PRT
<213> ORGANISM: Artificial Sequence
<220> FEATURE:
<223> OTHER INFORMATION: muFRIHC9-20 VH Chain

<400> SEQUENCE: 31

Gln Val Gln Leu Gln Gln Ser Gly Pro Asp Leu Val Lys Pro Gly Ala
1               5                   10                  15

Ser Val Arg Ile Ser Cys Lys Ala Ser Gly Phe Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Glu Asn Val Asn Val Arg Tyr Asn Asp Lys Phe

```
                    50                  55                  60
Lys Ala Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                     85                  90                  95

Ala Arg Arg Gly Ile Tyr Tyr Tyr Ser Pro Tyr Ala Met Asp Tyr Trp
                100                 105                 110

Gly Gln Gly Ala Ser Val Thr Val Ser Ser
            115                 120

<210> SEQ ID NO 32
<211> LENGTH: 114
<212> TYPE: PRT
<213> ORGANISM: Artificial Sequence
<220> FEATURE:
<223> OTHER INFORMATION: muFRIHC9-20 VL Chain

<400> SEQUENCE: 32

Ser Asp Val Val Leu Thr Gln Thr Pro Leu Ser Leu Pro Val Asn Leu
 1               5                  10                  15

Gly Asp Gln Ala Ser Ile Ser Cys Lys Ser Thr Lys Ser Leu Leu Asn
                20                  25                  30

Ser Asp Gly Phe Thr Tyr Leu Asp Trp Tyr Leu Gln Lys Pro Gly Gln
            35                  40                  45

Ser Pro Gln Leu Leu Ile Tyr Leu Val Ser Asn His Phe Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Tyr Cys Phe Gln
                 85                  90                  95

Ser Asn Tyr Leu Pro Leu Thr Phe Gly Gly Gly Thr Lys Leu Glu Ile
                100                 105                 110

Lys Arg

<210> SEQ ID NO 33
<211> LENGTH: 446
<212> TYPE: PRT
<213> ORGANISM: Artificial Sequence
<220> FEATURE:
<223> OTHER INFORMATION: muFRIHC2-1 Full-Length Heavy Chain

<400> SEQUENCE: 33

Gln Val Gln Leu Gln Gln Ser Gly Pro Glu Leu Val Lys Pro Gly Ala
 1               5                  10                  15

Ser Val Arg Ile Ser Cys Lys Ala Ser Gly Tyr Thr Phe Thr Asn Ser
                20                  25                  30

Tyr Ile His Trp Val Lys Arg Pro Gly Gln Gly Leu Glu Trp Ile
            35                  40                  45

Gly Trp Ile Tyr Pro Glu Ser Leu Asn Thr Gln Tyr Asn Glu Lys Phe
     50                  55                  60

Lys Ala Lys Ala Thr Leu Thr Ala Asp Lys Ser Ser Ser Thr Ser Tyr
 65                  70                  75                  80

Met Gln Leu Ser Ser Leu Thr Ser Glu Asp Ser Ala Val Tyr Phe Cys
                 85                  90                  95

Ala Arg Arg Gly Ile Tyr Tyr Tyr Ser Pro Tyr Ala Leu Asp His Trp
                100                 105                 110

Gly Gln Gly Ala Ser Val Thr Val Ser Ser Ala Lys Thr Thr Pro Pro
```

```
            115                 120                 125
Ser Val Tyr Pro Leu Ala Pro Gly Ser Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Glu Ser Asp Leu Tyr Thr Leu Ser Ser Ser Val Thr Val
            180                 185                 190

Pro Ser Ser Met Arg Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asn Thr Asn
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 34
<211> LENGTH: 220
<212> TYPE: PRT
<213> ORGANISM: Artificial Sequence
<220> FEATURE:
<223> OTHER INFORMATION: muFRIHC2-1 Full-length Light Chain

<400> SEQUENCE: 34

Ser Asp Val Val Leu Thr Gln Thr Pro Leu Ser Leu Pro Val Asn Ile
1               5                   10                  15

Gly Asp Gln Ala Ser Ile Ser Cys Lys Ser Ser Lys Ser Leu Leu Asn
            20                  25                  30

Ser Asp Gly Phe Thr Tyr Leu Asp Trp Tyr Leu Gln Lys Pro Gly Gln
```

```
                35                  40                  45
Ser Pro Gln Leu Leu Ile Tyr Leu Val Ser Asn His Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Tyr Cys Phe Gln
                 85                  90                  95

Ser Asn Tyr Leu Pro Leu Thr Phe Gly Gly Gly Thr Lys Leu Glu Ile
                100                 105                 110

Lys Arg Ala Asp Ala Ala Pro Thr Val Ser Ile Phe Pro Pro Ser Ser
                115                 120                 125

Glu Gln Leu Thr Ser Gly Gly Ala Ser Val Val Cys Phe Leu Asn Asn
                130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
                180                 185                 190

Glu Arg His Asn Ser Tyr Thr Cys Glu Ala Thr His Lys Thr Ser Thr
                195                 200                 205

Ser Pro Ile Val Lys Ser Phe Asn Arg Asn Glu Cys
                210                 215                 220

<210> SEQ ID NO 35
<211> LENGTH: 446
<212> TYPE: PRT
<213> ORGANISM: Artificial Sequence
<220> FEATURE:
<223> OTHER INFORMATION: muFRIHC5-7 Full-Length Heavy Chain

<400> SEQUENCE: 35

Gln Val Gln Leu Gln Gln Ser Gly Pro Glu Val Val Lys Pro Gly Ala
1               5                   10                  15

Ser Val Arg Ile Ser Cys Lys Ala Ser Gly Tyr Thr Phe Thr Asn Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Phe Asn Val Glu Tyr Asn Glu Lys Phe
 50                  55                  60

Lys Ala Lys Ala Thr Leu Thr Ala Asp Lys Ser Ser Ser Thr Val Tyr
 65                  70                  75                  80

Met Gln Leu Ser Ser Leu Thr Ser Glu Asp Ser Ala Val Tyr Phe Cys
                 85                  90                  95

Ala Arg Arg Gly Ile Tyr Phe Tyr Ser Pro Tyr Ala Leu Asp Tyr Trp
                100                 105                 110

Gly Gln Gly Ala Ser Val Thr Val Ser Ala Lys Thr Thr Pro Pro
                115                 120                 125

Ser Val Tyr Pro Leu Ala Pro Gly Ser Ala Ala Gln Thr Asn Ser Met
                130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Glu Ser Asp Leu Tyr Thr Leu Ser Ser Ser Val Thr Val
```

```
                    180                 185                 190
Pro Ser Ser Met Arg Pro Ser Glu Thr Val Thr Cys Asn Val Ala His
                195                 200                 205
Pro Ala Ser Ser Thr Lys Val Asp Lys Lys Ile Val Pro Arg Asp Cys
            210                 215                 220
Gly Cys Lys Pro Cys Ile Cys Thr Val Pro Glu Val Ser Ser Val Phe
225                 230                 235                 240
Ile Phe Pro Pro Lys Pro Lys Asp Val Leu Thr Ile Thr Leu Thr Pro
                245                 250                 255
Lys Val Thr Cys Val Val Val Asp Ile Ser Lys Asp Asp Pro Glu Val
            260                 265                 270
Gln Phe Ser Trp Phe Val Asp Asp Val Glu Val His Thr Ala Gln Thr
                275                 280                 285
Gln Pro Arg Glu Glu Gln Phe Asn Ser Thr Phe Arg Ser Val Ser Glu
            290                 295                 300
Leu Pro Ile Met His Gln Asp Trp Leu Asn Gly Lys Glu Phe Lys Cys
305                 310                 315                 320
Arg Val Asn Ser Ala Ala Phe Pro Ala Pro Ile Glu Lys Thr Ile Ser
                325                 330                 335
Lys Thr Lys Gly Arg Pro Lys Ala Pro Gln Val Tyr Thr Ile Pro Pro
            340                 345                 350
Pro Lys Glu Gln Met Ala Lys Asp Lys Val Ser Leu Thr Cys Met Ile
            355                 360                 365
Thr Asp Phe Phe Pro Glu Asp Ile Thr Val Glu Trp Gln Trp Asn Gly
        370                 375                 380
Gln Pro Ala Glu Asn Tyr Lys Asn Thr Gln Pro Ile Met Asn Thr Asn
385                 390                 395                 400
Gly Ser Tyr Phe Val Tyr Ser Lys Leu Asn Val Gln Lys Ser Asn Trp
                405                 410                 415
Glu Ala Gly Asn Thr Phe Thr Cys Ser Val Leu His Glu Gly Leu His
            420                 425                 430
Asn His His Thr Glu Lys Ser Leu Ser His Ser Pro Gly Lys
        435                 440                 445

<210> SEQ ID NO 36
<211> LENGTH: 220
<212> TYPE: PRT
<213> ORGANISM: Artificial Sequence
<220> FEATURE:
<223> OTHER INFORMATION: muFRIHC5-7 Full-Length Light Chain

<400> SEQUENCE: 36

Ser Asp Val Val Leu Thr Gln Thr Pro Leu Ser Leu Pro Val Asn Ile
1               5                   10                  15
Gly Asp Gln Ala Ser Ile Ser Cys Lys Ser Thr Glu Ser Leu Leu Asn
            20                  25                  30
Ser Asp Gly Phe Thr Tyr Leu Asp Trp Tyr Leu Gln Lys Pro Gly Gln
        35                  40                  45
Ser Pro Gln Leu Leu Ile Tyr Leu Val Ser Asn His Phe Ser Gly Val
    50                  55                  60
Pro Asp Arg Phe Ser Gly Ser Gly Ser Gly Thr Asp Phe Thr Leu Lys
65                  70                  75                  80
Ile Ser Arg Val Glu Ala Glu Asp Leu Gly Val Tyr Tyr Cys Phe Gln
                85                  90                  95
Ser Asn Tyr Leu Pro Leu Thr Phe Gly Gly Gly Thr Lys Leu Glu Val
```

-continued

```
                100                 105                 110
Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
        130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 37
<211> LENGTH: 446
<212> TYPE: PRT
<213> ORGANISM: Artificial Sequence
<220> FEATURE:
<223> OTHER INFORMATION: muFRIHC9-20 Full-Length Heavy Chain

<400> SEQUENCE: 37

Gln Val Gln Leu Gln Gln Ser Gly Pro Asp Leu Val Lys Pro Gly Ala
1               5                   10                  15

Ser Val Arg Ile Ser Cys Lys Ala Ser Gly Phe Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Glu Asn Val Asn Val Arg Tyr Asn Asp Lys Phe
    50                  55                  60

Lys Ala Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Ile Tyr Tyr Tyr Ser Pro Tyr Ala Met Asp Tyr Trp
            100                 105                 110

Gly Gln Gly Ala Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Glu Ser Asp Leu Tyr Thr Leu Ser Ser Ser Val Thr Val
            180                 185                 190

Pro Ser Ser Met Arg Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
```

```
                        245                 250                 255
Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asn Thr Asn
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 38
<211> LENGTH: 220
<212> TYPE: PRT
<213> ORGANISM: Artificial Sequence
<220> FEATURE:
<223> OTHER INFORMATION: muFRIHC9-20 Full-Length Light Chain

<400> SEQUENCE: 38

Ser Asp Val Val Leu Thr Gln Thr Pro Leu Ser Leu Pro Val Asn Leu
1               5                   10                  15

Gly Asp Gln Ala Ser Ile Ser Cys Lys Ser Thr Lys Ser Leu Leu Asn
            20                  25                  30

Ser Asp Gly Phe Thr Tyr Leu Asp Trp Tyr Leu Gln Lys Pro Gly Gln
        35                  40                  45

Ser Pro Gln Leu Leu Ile Tyr Leu Val Ser Asn His Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
                85                  90                  95

Ser Asn Tyr Leu Pro Leu Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
```

165                 170                 175
Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 39
<211> LENGTH: 366
<212> TYPE: DNA
<213> ORGANISM: Artificial Sequence
<220> FEATURE:
<223> OTHER INFORMATION: muFRIHC2-1 VH Chain

<400> SEQUENCE: 39
caggtccaac tgcagcagtc tggacctgag ctggtgaagc ctggggcttc agtgaggata    60
tcctgcaagg cttctggcta caccttcaca aactcctata ttcactgggt gaaaagagg    120 cctggacagg gacttgagtg gattggatgg atttatcctg aaagtcttaa tactcaatac   180
aatgagaagt tcaaggccaa ggccacactg actgctgaca gtcctccag cacatcctac    240 atgcagctca gcagtctgac ctctgaggac tctgcggtct atttctgtgc aagaaggggt   300
atttattact actctcccta tgctctggac cactggggtc aaggagcctc agtcaccgtc   360
tcctca                                                              366

<210> SEQ ID NO 40
<211> LENGTH: 342
<212> TYPE: DNA
<213> ORGANISM: Artificial Sequence
<220> FEATURE:
<223> OTHER INFORMATION: muFRIHC2-1 VL Chain

<400> SEQUENCE: 40
agtgatgttg ttctgaccca aactccactc tctctgcctg tcaatattgg agatcaagcc    60
tctatctctt gcaagtcttc taagagtctt ctgaatagtg atggattcac ttatttggac   120
tggtacctgc agaagccagg ccagtctcca cagctcctaa tatatttggt ttctaatcat   180
ttttctggag ttccagacag gttcagtggc agtgggtcag gaacagattt cacactcaag   240
atcagcagag tggaggctga ggatttggga gtttattatt gcttccagag taactatctt   300
cctctcacgt tcggaggggg gaccaagctg gaaataaaac gg                     342

<210> SEQ ID NO 41
<211> LENGTH: 366
<212> TYPE: DNA
<213> ORGANISM: Artificial Sequence
<220> FEATURE:
<223> OTHER INFORMATION: muFRIHC5-7 VH Chain

<400> SEQUENCE: 41
caggtccaac tgcagcagtc tggacctgag gtggtgaagc ctggggcttc agtgaggata    60
tcctgcaagg cttctggcta caccttcaca aactactata tacactgggt gaagcagagg   120
cctggacagg gacttgagtg gattggatgg atttatcctg aaagttttaa tgttgagtac   180
aatgagaagt tcaaggccaa ggccacactg actgcagaca atcctccag cacagtctac    240 atgcaactca gcagcctgac ctctgaggac tctgcggtct atttctgtgc aagaaggggt   300
atttatttct actctcccta tgctttggac tactggggtc aaggagcctc agtcaccgtc   360

```
tcctca                                                              366
```

<210> SEQ ID NO 42
<211> LENGTH: 342
<212> TYPE: DNA
<213> ORGANISM: Artificial Sequence
<220> FEATURE:
<223> OTHER INFORMATION: muFRIHC5-7 VL Chain

<400> SEQUENCE: 42

```
agtgatgttg ttctgaccca aactccactc tctctgcctg tcaatattgg agatcaagcc    60
tctatctctt gcaagtctac tgagagtctt ctgaatagtg atggattcac ttatttggac   120
tggtacctgc agaagccagg ccagtctcca cagctcctaa tatatttggt ttctaatcat   180
ttttctggag ttccagacag gttcagtggc agtgggtcag gaacagattt cacactcaag   240
atcagcagag tggaggctga ggatttggga gtttattatt gcttccagag taactatctt   300
cctctcacgt tcggaggggg gaccaagctg gaagtaaaac gg                      342
```

<210> SEQ ID NO 43
<211> LENGTH: 366
<212> TYPE: DNA
<213> ORGANISM: Artificial Sequence
<220> FEATURE:
<223> OTHER INFORMATION: muFRIHC9-20 VH Chain

<400> SEQUENCE: 43

```
caggtccaac tgcagcagtc tggacctgac ctggtgaagc ctggggcttc agtgaggata    60
tcctgcaagg cttctggctt caccttcaca aactactata tacactgggt gaagcagagg   120
cctggacagg gacttgagtg gattggatgg atttatcctg aaaatgttaa tgttaggtac   180
aatgacaagt tcaaggccaa ggccacactg actgcagaca atcctccag cacagcctac    240
atgcagctca gcagcctgac ctctgaggac tctgcggtct atttctgtgc aagaaggggt   300
atttattact actctcccta tgctatggac tactggggtc aaggagcctc agtcaccgtc   360
tcctca                                                              366
```

<210> SEQ ID NO 44
<211> LENGTH: 342
<212> TYPE: DNA
<213> ORGANISM: Artificial Sequence
<220> FEATURE:
<223> OTHER INFORMATION: muFRIHC9-20 VL Chain

<400> SEQUENCE: 44

```
agtgatgttg ttctgaccca aactccactc tctctgcctg tcaatcttgg agatcaagcc    60
tctatctctt gcaagtctac taagagtctt ctgaatagtg atggattcac ttatttggac   120
tggtacctgc agaagccagg ccagtctcca cagctcctaa tatatttggt ttctaatcat   180
ttttctggag ttccagacag gttcagtggc agtgggtcag gaacagattt caccctcaag   240
atcagcagag tggaggctga ggatttggga gtttattatt gcttccagag taactatctt   300
cctctcacgt tcggaggggg gaccaagctg gaaataaaac gg                      342
```

<210> SEQ ID NO 45
<211> LENGTH: 118
<212> TYPE: PRT
<213> ORGANISM: Artificial Sequence
<220> FEATURE:
<223> OTHER INFORMATION: huMov19 vHC

<400> SEQUENCE: 45

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
            115
```

<210> SEQ ID NO 46
<211> LENGTH: 112
<212> TYPE: PRT
<213> ORGANISM: Artificial Sequence
<220> FEATURE:
<223> OTHER INFORMATION: huMov19 vLCv1.00

<400> SEQUENCE: 46

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

<210> SEQ ID NO 47
<211> LENGTH: 112
<212> TYPE: PRT
<213> ORGANISM: Artificial Sequence
<220> FEATURE:
<223> OTHER INFORMATION: huMov19 vLCv1.60

<400> SEQUENCE: 47

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
```

```
                65                  70                  75                  80
Pro Val Glu Ala Glu Asp Ala Ala Thr Tyr Tyr Cys Gln Gln Ser Arg
                    85                  90                  95
Glu Tyr Pro Tyr Thr Phe Gly Gly Gly Thr Lys Leu Glu Ile Lys Arg
                    100                 105                 110

<210> SEQ ID NO 48
<211> LENGTH: 15
<212> TYPE: PRT
<213> ORGANISM: Artificial Sequence
<220> FEATURE:
<223> OTHER INFORMATION: huMov19 vLC CDR1

<400> SEQUENCE: 48

Lys Ala Ser Gln Ser Val Ser Phe Ala Gly Thr Ser Leu Met His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: huMov19 vLC CDR2

<400> SEQUENCE: 49

Arg Ala Ser Asn Leu Glu Ala
1               5

<210> SEQ ID NO 50
<211> LENGTH: 9
<212> TYPE: PRT
<213> ORGANISM: Artificial Sequence
<220> FEATURE:
<223> OTHER INFORMATION: huMov19 vLC CDR3

<400> SEQUENCE: 50

Gln Gln Ser Arg Glu Tyr Pro Tyr Thr
1               5

<210> SEQ ID NO 51
<211> LENGTH: 5
<212> TYPE: PRT
<213> ORGANISM: Artificial Sequence
<220> FEATURE:
<223> OTHER INFORMATION: huMov19 vHC CDR1

<400> SEQUENCE: 51

Gly Tyr Phe Met Asn
1               5

<210> SEQ ID NO 52
<211> LENGTH: 17
<212> TYPE: PRT
<213> ORGANISM: Artificial Sequence
<220> FEATURE:
<223> OTHER INFORMATION: huMov19 vHC CDR2 - Kabat Defined

<400> SEQUENCE: 52

Arg Ile His Pro Tyr Asp Gly Asp Thr Phe Tyr Asn Gln Lys Phe Gln
1               5                   10                  15
Gly

<210> SEQ ID NO 53
<211> LENGTH: 10
<212> TYPE: PRT
```

-continued

```
<213> ORGANISM: Artificial Sequence
<220> FEATURE:
<223> OTHER INFORMATION: huMov19 vHC CDR2 - Abm Defined

<400> SEQUENCE: 53

Arg Ile His Pro Tyr Asp Gly Asp Thr Phe
1               5                   10

<210> SEQ ID NO 54
<211> LENGTH: 9
<212> TYPE: PRT
<213> ORGANISM: Artificial Sequence
<220> FEATURE:
<223> OTHER INFORMATION: huMov19 vHC CDR3

<400> SEQUENCE: 54

Tyr Asp Gly Ser Arg Ala Met Asp Tyr
1               5

<210> SEQ ID NO 55
<211> LENGTH: 448
<212> TYPE: PRT
<213> ORGANISM: Artificial Sequence
<220> FEATURE:
<223> OTHER INFORMATION: huMov19 HC amino acid sequence

<400> SEQUENCE: 55

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 56
<211> LENGTH: 218
<212> TYPE: PRT
<213> ORGANISM: Artificial Sequence
<220> FEATURE:
<223> OTHER INFORMATION: huMov19 LCv1.00

<400> SEQUENCE: 56

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 57
<211> LENGTH: 218
<212> TYPE: PRT
<213> ORGANISM: Artificial Sequence
<220> FEATURE:
<223> OTHER INFORMATION: huMov19 LCv1.60

<400> SEQUENCE: 57

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 58
<211> LENGTH: 17
<212> TYPE: PRT
<213> ORGANISM: Artificial Sequence
<220> FEATURE:
<223> OTHER INFORMATION: muMov19 vHC CDR2 - Kabat Defined

<400> SEQUENCE: 58

```
Arg Ile His Pro Tyr Asp Gly Asp Thr Phe Tyr Asn Gln Asn Phe Lys
1               5                   10                  15

Asp
```

<210> SEQ ID NO 59

```
<211> LENGTH: 16
<212> TYPE: PRT
<213> ORGANISM: Artificial Sequence
<220> FEATURE:
<223> OTHER INFORMATION: FRIHC2-1 Resurfaced or Grafted Light Chain
      v1.0 CDR1

<400> SEQUENCE: 59

Arg Ser Ser Arg Ser Leu Leu Asn Ser Asp Gly Phe Thr Tyr Leu Asp
1               5                   10                  15

<210> SEQ ID NO 60
<211> LENGTH: 10
<212> TYPE: PRT
<213> ORGANISM: Artificial Sequence
<220> FEATURE:
<223> OTHER INFORMATION: FRIHC2-1 Resurfaced Heavy Chain CDR2

<400> SEQUENCE: 60

Trp Ile Tyr Pro Glu Ser Leu Asn Thr Gln
1               5                   10

<210> SEQ ID NO 61
<211> LENGTH: 17
<212> TYPE: PRT
<213> ORGANISM: Artificial Sequence
<220> FEATURE:
<223> OTHER INFORMATION: FRIHC2-1 Resurfaced HC CDR2

<400> SEQUENCE: 61

Trp Ile Tyr Pro Glu Ser Leu Asn Thr Gln Tyr Asn Gln Lys Phe Gln
1               5                   10                  15

Gly

<210> SEQ ID NO 62
<211> LENGTH: 122
<212> TYPE: PRT
<213> ORGANISM: Artificial Sequence
<220> FEATURE:
<223> OTHER INFORMATION: huFRIHC2-1 (resurfaced) VH Chain

<400> SEQUENCE: 62

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asn Ser
            20                  25                  30

Tyr Ile His Trp Val Lys Lys Arg Pro Gly Gln Gly Leu Glu Trp Ile
        35                  40                  45

Gly Trp Ile Tyr Pro Glu Ser Leu Asn Thr Gln Tyr Asn Gln Lys Phe
    50                  55                  60

Gln Gly Lys Ala Thr Leu Thr Ala Asp Lys Ser Ser Thr Ser Thr Tyr
65                  70                  75                  80

Met Gln Leu Ser Ser Leu Thr Ser Glu Asp Ser Ala Val Tyr Phe Cys
                85                  90                  95

Ala Arg Arg Gly Ile Tyr Tyr Tyr Ser Pro Tyr Ala Leu Asp His Trp
            100                 105                 110

Gly Gln Gly Ala Ser Val Thr Val Ser Ser
        115                 120

<210> SEQ ID NO 63
<211> LENGTH: 113
<212> TYPE: PRT
<213> ORGANISM: Artificial Sequence
```

<220> FEATURE:
<223> OTHER INFORMATION: huFRIHC2-1 v. 1.0 (resurfaced) VL Chain

<400> SEQUENCE: 63

Asp Val Val Leu Thr Gln Ser Pro Leu Ser Leu Pro Val Asn Leu Gly
1               5                   10                  15

Gln Pro Ala Ser Ile Ser Cys Arg Ser Arg Ser Leu Leu Asn Ser
            20                  25                  30

Asp Gly Phe Thr Tyr Leu Asp Trp Tyr Leu Gln Lys Pro Gly Gln Ser
            35                  40                  45

Pro Arg Leu Leu Ile Tyr Leu Val Ser Asn His Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg

<210> SEQ ID NO 64
<211> LENGTH: 113
<212> TYPE: PRT
<213> ORGANISM: Artificial Sequence
<220> FEATURE:
<223> OTHER INFORMATION: huFRIHC2-1 v. 1.01 (resurfaced) VL Chain

<400> SEQUENCE: 64

Asp Val Val Leu Thr Gln Ser Pro Leu Ser Leu Pro Val Asn Leu Gly
1               5                   10                  15

Gln Pro Ala Ser Ile Ser Cys Lys Ser Ser Lys Ser Leu Leu Asn Ser
            20                  25                  30

Asp Gly Phe Thr Tyr Leu Asp Trp Tyr Leu Gln Lys Pro Gly Gln Ser
            35                  40                  45

Pro Arg Leu Leu Ile Tyr Leu Val Ser Asn His Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Gln Gly Thr Lys Leu Glu Ile Lys
            100                 105                 110

Arg

<210> SEQ ID NO 65
<211> LENGTH: 125
<212> TYPE: PRT
<213> ORGANISM: Artificial Sequence
<220> FEATURE:
<223> OTHER INFORMATION: huFRIHC2-1 (grafted) VH Chain

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Ser
            20                  25                  30

Tyr Ile His Trp Val Arg Gln Ala Pro Gly Gln Gly Leu Glu Trp Met
            35                  40                  45

```
Gly Trp Ile Tyr Pro Glu Ser Leu Asn Thr Gln Tyr Asn Glu Lys Phe
            50                  55                  60

Lys Ala Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                85                  90                  95

Ala Arg Arg Gly Ile Tyr Tyr Tyr Ser Pro Tyr Ala Leu Asp His Trp
                    100                 105                 110

Gly Gln Gly Thr Leu Val Thr Val Ser Ser Ala Ser Thr
                115                 120                 125

<210> SEQ ID NO 66
<211> LENGTH: 112
<212> TYPE: PRT
<213> ORGANISM: Artificial Sequence
<220> FEATURE:
<223> OTHER INFORMATION: huFRIHC2-1 v. 1.0 (grafted) VL Chain

<400> SEQUENCE: 66

Asp Ile Val Met Thr Gln Thr Pro Leu Ser Leu Ser Val Thr Pro Gly
 1               5                  10                  15

Gln Pro Ala Ser Ile Ser Cys Arg Ser Arg Ser Leu Leu Asn Ser
                20                  25                  30

Asp Gly Phe Thr Tyr Leu Asp Trp Tyr Leu Gln Lys Pro Gly Gln Ser
            35                  40                  45

Pro Gln Leu Leu Ile Tyr Leu Val Ser Asn His Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
                100                 105                 110

<210> SEQ ID NO 67
<211> LENGTH: 112
<212> TYPE: PRT
<213> ORGANISM: Artificial Sequence
<220> FEATURE:
<223> OTHER INFORMATION: huFRIHC2-1 v. 1.01 (grafted) VL Chain

<400> SEQUENCE: 67

Asp Ile Val Met Thr Gln Thr Pro Leu Ser Leu Ser Val Thr Pro Gly
 1               5                  10                  15

Gln Pro Ala Ser Ile Ser Cys Lys Ser Ser Lys Ser Leu Leu Asn Ser
                20                  25                  30

Asp Gly Phe Thr Tyr Leu Asp Trp Tyr Leu Gln Lys Pro Gly Gln Ser
            35                  40                  45

Pro Gln Leu Leu Ile Tyr Leu Val Ser Asn His Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                85                  90                  95

Asn Tyr Leu Pro Leu Thr Phe Gly Gln Gly Thr Lys Leu Glu Ile Lys
                100                 105                 110
```

```
<210> SEQ ID NO 68
<211> LENGTH: 442
<212> TYPE: PRT
<213> ORGANISM: Artificial Sequence
<220> FEATURE:
<223> OTHER INFORMATION: muhuMov19 Full-Length Heavy Chain

<400> SEQUENCE: 68

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Glu
                165                 170                 175

Ser Asp Leu Tyr Thr Leu Ser Ser Ser Val Thr Val Pro Ser Ser Met
            180                 185                 190

Arg Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
```

```
                370                 375                 380
Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
                420                 425                 430

Glu Lys Ser Leu Ser His Ser Pro Gly Lys
        435                 440
```

<210> SEQ ID NO 69
<211> LENGTH: 218
<212> TYPE: PRT
<213> ORGANISM: Artificial Sequence
<220> FEATURE:
<223> OTHER INFORMATION: muhuMov19 Full-Length Light Chain

<400> SEQUENCE: 69

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 70
<211> LENGTH: 452
<212> TYPE: DNA
<213> ORGANISM: Artificial Sequence
<220> FEATURE:
<223> OTHER INFORMATION: huFRIHC2-1 (resurfaced) VH Chain

<400> SEQUENCE: 70

```
aagcttgcca ccatgggttg agctgcatt atccttttcc ttgtggctac agctactggc    60
gttcactctc aggtacaatt ggttcagtca ggagccgagg tcgtaaagcc cggtgccagt   120
```

```
gtgaagatct catgcaaggc aagcggttat acttttacaa actcttacat tcattgggtg    180
aaaaagcggc ccggccaggg tctcgaatgg atcggctgga tctacccaga aagtctgaac    240
actcaataca accagaagtt tcagggtaag gcaactctca ctgccgacaa gagctctagc    300
acaagctata tgcagttgtc tagtttgaca agcgaggata gcgcagttta cttttgtgct    360
cggcgtggta tttattacta ctcacccttat gctctggatc actggggaca gggtgcctct    420
gttaccgttt ccagtgcatc accaagggc cc    452

<210> SEQ ID NO 71
<211> LENGTH: 452
<212> TYPE: DNA
<213> ORGANISM: Artificial Sequence
<220> FEATURE:
<223> OTHER INFORMATION: huFRIHC2-1 (grafted) VH Chain

<400> SEQUENCE: 71
aagcttgcca ccatgggctg gagctgcata atcctcttcc tcgtagctac cgccactggg    60
gtgcattctc aagtacagtt ggtgcagtcc ggagctgaag tcaagaagcc aggggcttct    120
gttaaggtga gctgtaaggc ttccggatat accttcacaa acagttatat ccattgggtg    180
aggcaagctc caggccaggg tctcgaatgg atgggatgga tctaccccga gagtctgaac    240
acccagtaca cgagaagtt caaggcacgt gtgaccatga caagagacac ctccatcagt    300
acagcctata tggaattgag ccgtctcaga agtgatgata cagcagtgta ctactgcgcc    360 aggcgggggca tctactacta cagcccatac gctctcgacc actggggaca aggaacactg    420
gtaaccgtaa gctcagcttc tacaaagggc cc    452

<210> SEQ ID NO 72
<211> LENGTH: 411
<212> TYPE: DNA
<213> ORGANISM: Artificial Sequence
<220> FEATURE:
<223> OTHER INFORMATION: huFRIHC2-1 v. 1.0 (resurfaced) VL Chain

<400> SEQUENCE: 72
gaattcgcca ccatggggttg gtcatgtata atacttttcc tggtagctac tgctactggt    60
gtgcattcag atgtggtgct gactcagtca cccttgtctc tcccagtcaa tcttgggcag    120
ccagcatcta tcagctgccg aagcagcagg tctctcctga actccgatgg ctttacttat    180
cttgactggt atctccagaa gccaggacag tcccccggc tgctcatcta cctggtttct    240
aatcatttta gtggcgtccc tgaccgcttc tctgggagtg aagtgggac cgattttaca    300 ctgaagatct ccagggtcga agctgaggac cttggggttt actactgttt ccagagcaac    360
taccttccct tgacattcgg ccaggggaacc aagctggaaa tcaagcgtac g    411

<210> SEQ ID NO 73
<211> LENGTH: 411
<212> TYPE: DNA
<213> ORGANISM: Artificial Sequence
<220> FEATURE:
<223> OTHER INFORMATION: huFRIHC2-1 v. 1.01 (resurfaced) VL Chain

<400> SEQUENCE: 73
gaattcgcca ccatgggttg gtcttgtatc attctgttcc tggtcgccac tgccacagga    60
gttcactcag acgtggtact cacacaatct cccctttccc tgcctgtgaa cctgggacag    120
ccagcctcaa tcagttgcaa gagctctaaa tctctgctca atagcgatgg ctttacctac    180
```

```
ttggattggt acctccagaa gcccggccag tctcctcggc tcctgattta ccttgtttca    240
aatcactttt caggcgtgcc tgaccggttc tccggatctg gctcagggac agacttcacc    300
ctgaagatct cccgcgtcga ggcagaggat ctcggcgtgt attactgttt ccaaagtaac    360
tacctgccat tgactttggg acaaggaact aaactggaaa tcaaacgtac g             411

<210> SEQ ID NO 74
<211> LENGTH: 411
<212> TYPE: DNA
<213> ORGANISM: Artificial Sequence
<220> FEATURE:
<223> OTHER INFORMATION: huFRIHC2-1 v. 1.0 (grafted) VL Chain

<400> SEQUENCE: 74
gaattcgcca ccatgggatg gagttgtatt attctgttct ggtcgctac tgcaacaggc     60 gttcattctg acatcgtaat gacccagaca cctctgagtc tgagtgtcac tcccggccag    120
cccgcctcta tttcatgtcg tagctctcgc tccctgctca attccgacgg ttttacctac    180
ttggactggt atcttcagaa acctgggcag agccctcagc ttctgatcta tctggtgtcc    240
aatcacttca gtggcgtccc agaccgattt tccggaagcg gaagcggaac cgactttacc    300
ctgaagatat cccgcgtcga agcagaggac gtgggcgtgt attattgctt tcaaagcaat    360
tacttgccat tgactttcgg acaaggcaca aaactggaga ttaagcgtac g             411

<210> SEQ ID NO 75
<211> LENGTH: 411
<212> TYPE: DNA
<213> ORGANISM: Artificial Sequence
<220> FEATURE:
<223> OTHER INFORMATION: huFRIHC2-1 v. 1.01 (grafted) VL Chain

<400> SEQUENCE: 75
gaattcgcca ccatgggctg gtcatgcatc atactgttcc tggtggctac agcaaccggg    60
gtgcacagcg atattgttat gacacagaca ccactgagtt tgtcagtgac ccccggccag    120
ccagcctcta tatcctgcaa gtcctcaaaa agtctcctga atagcgatgg ctttacctac    180
ctcgactggt atcttcagaa gcccggtcaa agccctcagc tgctgatata tctggtgtct    240
aaccatttta gcggagtccc cgaccgcttt tcaggctccg gcagtggcac cgacttcacc    300
cttaagattt ctcgcgtgga ggctgaagat gtagggtct actactgttt ccagtcaaac    360
tacctgccac tgacctttgg tcaaggcact aagctcgaaa ttaagcgtac g             411
```

MONOCLONAL ANTIBODIES FOR DETECTION OF FOLATE RECEPTOR 1

CROSS REFERENCE TO RELATED APPLICATIONS

Related applications U.S. 61/872,407, filed Aug. 30, 2013, U.S. 61/875,475, filed Sep. 9, 2013, and U.S. 61/940,184, filed Feb. 14, 2014 are all incorporated herein by reference in their entireties.

REFERENCE TO A SEQUENCE LISTING SUBMITTED ELECTRONICALLY VIA EFS-WEB

The content of the electronically submitted sequence listing (Name: 29210440003_SequenceListing_ST25, Size: 68,699 bytes; and Date of Creation: Aug. 29, 2014), filed with the application is incorporated by reference in its entirety.

FIELD OF THE INVENTION

The field of this invention generally relates to diagnostic assays and kits for folate receptor 1-based therapies and antibodies that bind to human folate receptor 1.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, *Cancer J. Clin.* 53:5-26).

Folate Receptor 1 (FOLR1), also known as Folate Receptor-alpha or Folate Binding Protein, is an N-glycosylated protein expressed on plasma membrane of cells. FOLR1 has a high affinity for folic acid and for several reduced folic acid derivatives. FOLR1 mediates delivery of the physiological folate, 5-methyltetrahydrofolate, to the interior of cells.

FOLR1 is overexpressed in the vast majority of ovarian cancers, as well as in many uterine, endometrial, pancreatic, renal, lung, and breast cancers, while the expression of FOLR1 on normal tissues is restricted to the apical membrane of epithelial cells in the kidney proximal tubules, alveolar pneumocytes of the lung, bladder, testes, choroid plexus, and thyroid (Weitman S D, et al., *Cancer Res* 52: 3396-3401 (1992); Antony A C, *Annu Rev Nutr* 16: 501-521 (1996); Kalli K R, et al. *Gynecol Oncol* 108: 619-626 (2008)). This expression pattern of FOLR1 makes it a desirable target for FOLR1-directed cancer therapy.

Because ovarian cancer is typically asymptomatic until advanced stage, it is often diagnosed at a late stage and has poor prognosis when treated with currently available procedures, typically chemotherapeutic drugs after surgical de-bulking (von Gruenigen V et al., *Cancer* 112: 2221-2227 (2008); Ayhan A et al., *Am J Obstet Gynecol* 196: 81 e81-86 (2007); Harry V N et al., *Obstet Gynecol Surv* 64: 548-560 (2009)). Thus there is a clear unmet medical need for more effective diagnostics for ovarian cancers.

Some previous assays used to detect shed FOLR1 are not sufficiently specific to FOLR1. For example, some assays do not distinguish between FOLR1 and other folate receptor family members (FOLR2, 3, & 4) or report values for total FBP (Folate Binding Protein). Additionally, some assays require that human samples (e.g., plasma) be pre-treated with a light acid wash step to dissociate folic acid from the receptor. Some assay results may also have inaccuracies due to competitive effects between the antibody therapy and diagnostic antibody. Additionally, many commercially available kits are traditionally unreliable both in their reagents, and in their lot-to-lot stability. Evaluations of these kits have given very mixed results, and are intended for research use only. Many require that the human sample be pre-diluted before analysis to reduce the chance of false positives due to the "matrix effect." Thus, there is a clear need for highly sensitive and accurate diagnostic assays that can detect a clinically relevant dynamic range of FOLR1 as a companion for FOLR1-based therapies.

SUMMARY OF THE INVENTION

Anti-FOLR1 antibodies and antigen-binding fragments thereof as well as methods for detecting FOLR1, diagnosing FOLR1-mediated diseases and disorders (such as cancer), monitoring the efficacy of anti-FOLR1 therapies, optimizing anti-FOLR1 therapies, and stratifying patients are all provided herein.

The anti-FOLR1 antibodies provided herein can have a diagnostic role. For example, the anti-FOLR1 antibodies provided herein to distinguish between tumor and non-tumor cells or tissues or to identify tumor types, subtypes, or grades. In one embodiment, an anti-FOLR1 antibody provided herein and/or a FOLR1-detection assay provided herein can be used to distinguish between subtypes of non-small cell lung cancer (NSCLC) including adenocarcinoma and squamous cell carcinoma as described herein. In another embodiment, an anti-FOLR1 antibody provided herein and/or a FOLR1-detection assay provided herein can be used to rule out a type of cancer (e.g., to determine that a cell or tissue is not a type of cancer), for example, sarcoma.

In some embodiments, an antibody or antigen-binding fragment thereof provided herein can specifically bind to an epitope of FOLR1, wherein the epitope comprises at least one, at least two, or three N-glycoslated amino acids. Glycosylation can be critical for membrane localization. See e.g., Yan et al., *J. Am. Soc. Nephol.* 13: 1385-1389 (2002). Advantageously, the antibodies and antigen-binding fragments herein can detect FOLR1 expression on cell membranes and detect a clinically relevant dynamic range of FOLR1. The more discreet staining obtained with the antibodies and antigen-binding fragments provided herein allows for discrimination among samples all grouped together as high expression levels (with a score of 3) using antibodies that bind to different FOLR1 epitopes, lack sufficient specificity, and/or lack sufficient sensitivity.

In some embodiments, an antibody or antigen-binding fragment thereof provided herein can specifically bind to the same FOLR1 epitope as an antibody selected from the group consisting of: (a) an antibody comprising the polypeptide of SEQ ID NO:27 and the polypeptide of SEQ ID NO:28; (b) an antibody comprising the polypeptide of SEQ ID NO:29 and the polypeptide of SEQ ID NO:30; (c) an antibody comprising the polypeptide of SEQ ID NO:31 and the polypeptide of SEQ ID NO:32; (d) an antibody comprising the polypeptide of SEQ ID NO:62 and the polypeptide of SEQ ID NO:63 or SEQ ID NO:64; and (e) an antibody comprising the polypeptide of SEQ ID NO:65 and the polypeptide of SEQ ID NO:66 or SEQ ID NO:67. In some embodiments, the epitope comprises an N-glycosylated amino acid.

In some embodiments, an antibody or antigen-binding fragment thereof provided herein can specifically bind to FOLR1, wherein said antibody or fragment thereof competitively inhibits binding to FOLR1 of an antibody selected from the group consisting of: (a) an antibody comprising the polypeptide of SEQ ID NO:27 and the polypeptide of SEQ ID NO:28; (b) an antibody comprising the polypeptide of SEQ ID NO:29 and the polypeptide of SEQ ID NO:30; (c) an antibody comprising the polypeptide of SEQ ID NO:31 and the polypeptide of SEQ ID NO:32; (d) an antibody comprising the polypeptide of SEQ ID NO:62 and the polypeptide of SEQ ID NO:63 or SEQ ID NO:64; and (e) an antibody comprising the polypeptide of SEQ ID NO:65 and the polypeptide of SEQ ID NO:66 or SEQ ID NO:67.

In some embodiments, the antibody or antigen-binding fragment thereof comprises the VH CDR1-3 and VL CDR1-3 polypeptide sequences selected from the group consisting of: (a) SEQ ID NOs:3-8, respectively; (b) SEQ ID NOs:9-14, respectively; (c) SEQ ID NOs:15-20, respectively; (d) SEQ ID NOs:21-26, respectively; (e) SEQ ID NOs: 3-5 and SEQ ID NOs: 59, 7, and 8, respectively; (f) SEQ ID NOs: 3, 60, and 5 and SEQ ID NOs: 6-8, respectively; (g) SEQ ID NOs: 3, 61, and 5 and SEQ ID NOs: 6-8, respectively; (h) SEQ ID NOs: 3, 60, and 5 and SEQ ID NOs: 59, 7, and 8, respectively; and (i) SEQ ID NOs: 3, 61, and 5 and SEQ ID NOs: 59, 7, and 8, respectively.

In some embodiments, an antibody or antigen-binding fragment thereof provided herein can specifically bind to FOLR1, wherein the antibody or fragment thereof comprises the VH CDR1-3 and VL CDR1-3 polypeptide sequences selected from the group consisting of: (a) SEQ ID NOs:3-8, respectively; (b) SEQ ID NOs:9-14, respectively; (c) SEQ ID NOs:15-20, respectively; (d) SEQ ID NOs:21-26, respectively; (e) SEQ ID NOs: 3-5 and SEQ ID NOs: 59, 7, and 8, respectively; (f) SEQ ID NOs: 3, 60, and 5 and SEQ ID NOs: 6-8, respectively; (g) SEQ ID NOs: 3, 61, and 5 and SEQ ID NOs: 6-8, respectively; (h) SEQ ID NOs: 3, 60, and 5 and SEQ ID NOs: 59, 7, and 8, respectively; (i) SEQ ID NOs: 3, 61, and 5 and SEQ ID NOs: 59, 7, and 8, respectively; and (j) variants of (a) to (i) comprising 1, 2, 3, or 4 conservative amino acid substitutions.

In some embodiments, the antibody or antigen-binding fragment thereof comprises polypeptide sequences that are at least 90%, at least 95%, or at least 99% identical to polypeptide sequences selected from the group consisting of: (a) SEQ ID NO:27 and SEQ ID NO:28; (b) SEQ ID NO:29 and SEQ ID NO:30; (c) SEQ ID NO:31 and SEQ ID NO:32; (d) SEQ ID NO:62 and SEQ ID NO:63 or SEQ ID NO:64; (e) SEQ ID NO:65 and SEQ ID NO:66 or SEQ ID NO:67; (f) SEQ ID NO:68 and SEQ ID NO:69. In some embodiments, the polypeptide sequences comprise, consist essentially of, or consist of the amino acids of sequences selected from the group consisting of: (a) SEQ ID NO:27 and SEQ ID NO:28; (b) SEQ ID NO:29 and SEQ ID NO:30; (c) SEQ ID NO:31 and SEQ ID NO:32; (d) SEQ ID NO:62 and SEQ ID NO:63 or SEQ ID NO:64; (e) SEQ ID NO:65 and SEQ ID NO:66 or SEQ ID NO:67; (f) SEQ ID NO:68 and SEQ ID NO:69.

In some embodiments, an antibody or antigen-binding fragment thereof provided herein can specifically bind to FOLR1, wherein the antibody or fragment thereof comprises a humanized heavy chain variable region comprising CDR1, CDR2, and CDR3 regions comprising the amino acids of SEQ ID NO:51, SEQ ID NO:52 or 53, and SEQ ID NO:54, respectively, a humanized light chain variable region comprising CDR1, CDR2, and CDR3 regions comprising the amino acids of SEQ ID NO:48, SEQ ID NO:49, and SEQ ID NO:50, respectively, and a murine constant region. In some embodiments, the humanized heavy chain variable region comprises the amino acids of SEQ ID NO:45 and the humanized light chain variable region comprises the amino acids of SEQ ID NO:47.

In some embodiments, the antibody or antigen-binding fragment thereof is recombinantly produced. In some embodiments, the antibody or antigen-binding fragment thereof is murine, non-human, humanized, chimeric, resurfaced, or human. In some embodiments, the antibody or antigen-binding fragment thereof binds to human FOLR1 but not FOLR2 or FOLR3. In some embodiments, the antibody or antigen-binding fragment thereof is a full length antibody. In some embodiments, the antibody or antigen-binding fragment thereof is an antigen-binding fragment. In some embodiments, the antibody or antigen-binding fragment thereof comprises, consists essential of, or consist of a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In some embodiments, a polypeptide provided herein can specifically bind FOLR1, wherein the polypeptide comprises sequences selected from the group consisting of: (a) SEQ ID NOs:3-8, respectively; (b) SEQ ID NOs:9-14, respectively; (c) SEQ ID NOs:15-20, respectively; (d) SEQ ID NOs:21-26, respectively; (e) SEQ ID NOs: 3-5 and SEQ ID NOs: 59, 7, and 8, respectively; (f) SEQ ID NOs: 3, 60, and 5 and SEQ ID NOs: 6-8, respectively; (g) SEQ ID NOs: 3, 61, and 5 and SEQ ID NOs: 6-8, respectively (h) SEQ ID NOs: 3, 60, and 5 and SEQ ID NOs: 59, 7, and 8, respectively; (i) SEQ ID NOs: 3, 61, and 5 and SEQ ID NOs: 59, 7, and 8, respectively; and (j) variants of (a) to (i) comprising 1, 2, 3, or 4 conservative amino acid substitutions. In some embodiments, the polypeptide comprises sequences that are at least 90%, at least 95%, or at least 99% identical to sequences selected from the group consisting of: (a) SEQ ID NO:27 and SEQ ID NO:28; (b) SEQ ID NO:29 and SEQ ID NO:30; (c) SEQ ID NO:31 and SEQ ID NO:32; (d) SEQ ID NO:62 and SEQ ID NO:63 or SEQ ID NO:64; (e) SEQ ID NO:65 and SEQ ID NO:66 or SEQ ID NO:67; and (f) SEQ ID NO:68 and SEQ ID NO:69. In some embodiments, the polypeptide comprises the amino acids of (a) SEQ ID NO:27 and SEQ ID NO:28; (b) SEQ ID NO:29 and SEQ ID NO:30; (c) SEQ ID NO:31 and SEQ ID NO:32; (d) SEQ ID NO:62 and SEQ ID NO:63 or SEQ ID NO:64; (e) SEQ ID NO:65 and SEQ ID NO:66 or SEQ ID NO:67; or (f) SEQ ID NO:68 and SEQ ID NO:69.

In some embodiments, the antibody, antigen-binding fragment thereof, or polypeptide binds to FOLR1 with a Kd of about 0.5 to about 10 nM. In some embodiments, the antibody, antigen-binding fragment thereof, or polypeptide binds to a human FOLR1 with a Kd of about 1.0 nM or better. In some embodiments, the binding affinity is measured by flow cytometry, Biacore, ELISA, or radioimmunoassay.

In some embodiments, the antibody, antigen-binding fragment thereof, or polypeptide binds to an epitope of FOLR1 comprising an amino acid that is N-glycosylated.

In some embodiments, the antibody, antigen-binding fragment thereof, or polypeptide is detectably labeled.

In some embodiments, a cell provided herein produces the antibody, antigen-binding fragment thereof, or polypeptide. In some embodiments, the cell is isolated.

Methods of making the antibody, antigen-binding fragment thereof, or polypeptide are also provided. The methods can comprise (a) culturing a cell provided herein; and (b) isolating the antibody, antigen-binding fragment thereof, or polypeptide from the cultured cell.

Compositions comprising the antibody, antigen-binding fragment thereof, or polypeptide are also provided. In some embodiments, the composition comprises the the antibody, antigen-binding fragment thereof, or polypeptide and buffer selected from the group consisting of: a FACS buffer, an IHC buffer, and an ELISA buffer.

Methods of using the antibody, antigen-binding fragment thereof, or polypeptide are also provided.

In some embodiments, a method of detecting FOLR1 expression in a sample comprises contacting the sample with an antibody, antigen-binding fragment thereof, polypeptide, or composition provided herein. In some embodiments, the antibody or antigen-binding fragment thereof is detectably labeled. In some embodiments, the label is selected from the group consisting of immunofluorescent label, chemiluminescent label, phosphorescent label, enzyme label, radiolabel, avidin/biotin, colloidal gold particles, colored particles and magnetic particles. In some embodiments, the FOLR1 expression is determined by radioimmunoassay, Western blot assay, cytometry, immunofluorescent assay, enzyme immunoassay, immunoprecipitation assay, chemiluminescent assay, or immunohistochemical assay. In some embodiments, the cytometry is flow cytometry. In some embodiments, the FOLR1 expression is determined by IHC.

In some embodiments, a method for increasing the efficacy of cancer therapy with an active agent comprising an anti-FOLR1 antibody or antigen-binding fragment thereof, comprises administering the active agent to a subject having cancer, wherein increased expression of FOLR1 has been detected in a cancerous sample from the subject using an antibody, antigen-binding fragment thereof, polypeptide or composition provided herein.

In some embodiments, a method for identifying a cancer likely to respond to an active agent comprising an anti-FOLR1 antibody or antigen-binding fragment thereof comprises: (a) contacting a biological sample comprising cells from the cancer with the antibody, antigen-binding fragment thereof, polypeptide or composition provided herein; (b) detecting binding of the antibody, antibody-fragment, or polypeptide to FOLR1 in the biological sample of (a); (c) assigning a score to the binding of step (b), wherein the score is assigned based on comparison to one or more reference samples; and (d) comparing the score in step (c) to the score of a reference tissue or cell, wherein a score for the cancer FOLR1 level that is greater than the score for a normal or low FOLR1 expressing reference sample or a score for the cancer FOLR1 level that is equal to or greater than the score for a high FOLR1 expressing reference sample identifies the cancer as likely to respond to an anti-FOLR1 antibody.

In some embodiments, a method of treating a patient having cancer comprises: (a) determining a FOLR1 expression score from a detection of FOLR1 expression in a cancerous sample obtained from the patient, wherein the detection is performed using an antibody, antigen-binding fragment thereof, polypeptide or composition provided herein; and (b) administering an active agent comprising an anti-FOLR1 antibody or antigen-binding fragment thereof to the patient if the score indicates the patient will benefit from administration of the active agent.

In some embodiments, a method of treating a patient having cancer comprises (a) determining a FOLR1 expression score from a detection of FOLR1 expression in a cancerous sample obtained from the patient, wherein the detection is performed using an antibody, antigen-binding fragment thereof, polypeptide or composition provided herein; and (b) instructing a healthcare provider to administer an active agent comprising an anti-FOLR1 antibody or antigen-binding fragment thereof to the patient if the score indicates the patient will benefit from administration of the active agent.

In some embodiments, a method of treating a patient having cancer comprises: (a) submitting a cancerous sample taken from a patient having cancer for determining a FOLR1 expression score from a detection of FOLR1 expression using an antibody, antigen-binding fragment thereof, polypeptide, or composition provided herein; and (b) administering an active agent comprising an anti-FOLR1 antibody or antigen-binding fragment thereof to the patient if the score indicates the patient will benefit from administration of the active agent.

In some embodiments, a method of treating a patient having cancer comprises: (a) detecting FOLR1 expression in a cancerous sample obtained from the patient, wherein the detection is performed using an antibody, antigen-binding fragment thereof, polypeptide, or composition provided herein; (b) determining a FOLR1 expression score for the cancerous sample; and (c) administering an active agent comprising an anti-FOLR1 antibody or antigen-binding fragment thereof to the patient if the score indicates the patient will benefit from administration of the active agent.

In some embodiments, a method of treating a patient having cancer comprises: (a) administering to the patient a fixed dose of an active agent comprising an anti-FOLR1 antibody or antigen-binding fragment thereof; (b) detecting the patient's FOLR1 relative to the FOLR1 level in a reference sample, wherein the detection is performed using an antibody, antigen-binding fragment thereof, polypeptide, or composition provided herein; and (c) increasing the amount or frequency of subsequent fixed doses if the patient's FOLR1 level is elevated.

In some embodiments, a method of optimizing a therapeutic regimen with an active agent comprising an anti-FOLR1 antibody or antigen-binding fragment thereof for a subject having cancer comprises: (a) administering an increased dose of an active agent comprising an anti-FOLR1 antibody or antigen-binding fragment thereof to a subject having cancer wherein an increased expression of FOLR1 in the subject has been detected using an antibody, antigen-binding fragment thereof, polypeptide, or composition provided herein; or (b) administering a decreased dose of the active agent to a subject having cancer wherein a decreased expression of FOLR1 in the subject has been detected.

In some embodiments, a method of optimizing a therapeutic regimen with an active agent comprising an anti-FOLR1 antibody or antigen-binding fragment thereof for a subject having cancer comprises: (a) detecting the level of FOLR1 expression in a cancerous sample from the subject using an antibody, antigen-binding fragment thereof, polypeptide, or composition provided herein; (b) determining a FOLR1 expression score for the cancerous sample; and (c) administering an increased dose of an active agent comprising an anti-FOLR1 antibody or antigen-binding fragment thereof to the subject if the score is low or administering a decreased dose of the active agent to the subject if the score is high.

In some embodiments, a method of decreasing FOLR1-expressing cancer cells in a cancer patient comprises: (a) detecting the FOLR1 level in a cancerous sample taken from a patient, compared to the FOLR1 level in a reference sample using an antibody, antigen-binding fragment thereof, polypeptide, or composition provided herein; and (b) administering to the patient a fixed dose of an active agent comprising an anti-FOLR1 antibody or antigen-binding fragment thereof if the patient's FOLR1 level is elevated compared to the reference sample; wherein the administration of the active agent decreases the number of FOLR1-expressing cancer cells in the patient. In some embodiments, a method of treating cancer in a patient comprises: (a) detecting the FOLR1 level in a cancerous sample taken from a patient, compared to the FOLR1 level in a reference sample using an antibody, antigen-binding fragment thereof, polypeptide, or composition provided herein; and (b) administering to the patient a fixed dose of an active agent comprising an anti-FOLR1 antibody or antigen-binding fragment thereof if the patient's FOLR1 level is elevated compared to the reference sample; wherein the administration of the active agent decreases the size of a FOLR1-expressing tumor or decreases CA125 levels.

In some embodiments, a method of decreasing FOLR1-expressing cancer cells in a cancer patient comprises: (a) administering to a patient having a cancer a fixed dose of an active agent comprising an anti-FOLR1 antibody or antigen-binding fragment thereof; (b) detecting the patient's FOLR1 level relative to the FOLR1 level in a reference sample using an antibody, antigen-binding fragment thereof, polypeptide, or composition provided herein; and (c) increasing the amount or frequency of subsequent fixed doses if the patient's FOLR1 level is elevated compared to the reference sample; wherein the administration of the active agent decreases the number of FOLR1-expressing cancer cells in the patient. In some embodiments, a method of treating cancer in a patient comprises: (a) administering to a patient having a cancer a fixed dose of an active agent comprising an anti-FOLR1 antibody or antigen-binding fragment thereof; (b) detecting the patient's FOLR1 level relative to the FOLR1 level in a reference sample using an antibody, antigen-binding fragment thereof, polypeptide, or composition provided herein; and (c) increasing the amount or frequency of subsequent fixed doses if the patient's FOLR1 level is elevated compared to the reference sample; wherein the administration of the active agent decreases the size of a FOLR1-expressing tumor or decreases CA125 levels.

In some embodiments, a method of monitoring therapeutic efficacy of a fixed dose of an active agent comprising an anti-FOLR1 antibody or antigen-binding fragment thereof in a patient comprises: (a) detecting a first FOLR1 level in a biological sample from a patient having cancer using an antibody, antigen-binding fragment thereof, polypeptide, or composition provided herein; (b) administering to the patient a fixed dose of an active agent comprising an anti-FOLR1 antibody or antigen-binding fragment; (c) detecting a second FOLR1 level in a biological sample from the patient following active agent administration, wherein the detecting is performed using an antibody, antigen-binding fragment thereof, polypeptide, or composition provided herein; and (d) comparing the second FOLR1 level to the first FOLR1 level; wherein a decrease between the first and second FOLR1 level indicates therapeutic efficacy.

In some embodiments, a method of identifying a subject having a cancer as likely to respond to a low dose anti-FOLR1 treatment regimen, comprises: (a) contacting a biological sample comprising cells from the cancer with an antibody, antigen-binding fragment thereof, polypeptide, or composition provided herein; (b) detecting binding of the antibody, antigen-binding fragment, or polypeptide to the biological sample of (a); (c) assigning a score to the binding of step (b), wherein the score is assigned based on comparison to one or more reference samples; and (d) comparing the score in step (c) to the score of a reference tissue or cell, wherein a score for the cancer FOLR1 level that is greater than the score for a normal or low FOLR1 expressing reference sample or a score for the cancer FOLR1 level that is equal to or greater than the score for a high FOLR1 expressing reference sample identifies the cancer as likely to respond to a low dose anti-FOLR1 treatment.

In some embodiments, a method of identifying a cancer as sensitive to treatment with an anti-FOLR1 active agent, comprises: (a) detecting the level of FOLR1 expression in a cancerous sample from the cancer using an antibody, antigen-binding fragment thereof, polypeptide, or composition provided herein, wherein the detecting comprises the use of a method that distinguishes between staining intensity or staining uniformity in a FOLR1 expressing cancerous sample as compared to staining intensity or staining uniformity in one or more reference samples; (b) determining a FOLR1 staining intensity or staining uniformity score for the cancerous sample; and (c) comparing the FOLR1 staining intensity or staining uniformity score determined in step (b) to a relative value determined by measuring FOLR1 protein expression in at least one reference sample, wherein the at least one reference sample is a tissue, cell, or cell pellet sample which is not sensitive to treatment with an active agent comprising an anti-FOLR1 antibody or antigen-binding fragment thereof and wherein a FOLR1 staining intensity score for the cancerous sample determined in step (b) that is higher than the relative value identifies the cancer as being sensitive to treatment with the active agent.

In some embodiments, a method of identifying a cancer as sensitive to treatment with an anti-FOLR1 active agent, comprises: (a) detecting the level of FOLR1 expression in a cancerous sample from the cancer using an antibody, antigen-binding fragment thereof, polypeptide, or composition provided herein, wherein the detecting comprises the use of a method that specifically stains membrane FOLR1 in a FOLR1 expressing cancerous sample as compared to membrane FOLR1 in one or more reference samples; (b) determining a FOLR1 score for the cancerous sample; and (c) comparing the FOLR1 score determined in step (b) to a relative value determined by measuring FOLR1 in at least one reference sample, wherein the at least one reference sample is a tissue, cell, or cell pellet sample which is not sensitive to treatment with an active agent comprising an anti-FOLR1 antibody or antigen-binding fragment thereof and wherein a FOLR1 score for the cancerous sample determined in step (b) that is higher than the relative value identifies the cancer as being sensitive to treatment with the active agent.

In some embodiments, a method of identifying a cancer as sensitive to treatment with an anti-FOLR1 active agent, comprises: (a) detecting the level of FOLR1 expression in a cancerous sample from the cancer using an antibody, antigen-binding fragment thereof, polypeptide, or composition provided herein, wherein the detecting comprises the use of a method that distinguishes between staining intensity or staining uniformity in a FOLR1 expressing cancerous sample as compared to staining intensity or staining uniformity in one or more reference samples; (b) determining a FOLR1 staining intensity or staining uniformity score for the cancerous sample; and (c) comparing the FOLR1 staining intensity or staining uniformity score determined in step (b) to a relative value determined by measuring FOLR1 protein expression in at least one reference sample, wherein the at least one reference sample is a tissue, cell, or cell pellet sample which is sensitive to treatment with an active agent comprising an anti-FOLR1 antibody or antigen-binding fragment thereof and wherein a FOLR1 staining intensity score for the cancerous sample determined in step (b) that is greater than or equal to the relative value identifies the cancer as being sensitive to treatment with the active agent.

In some embodiments, a method of identifying a cancer as sensitive to treatment with an anti-FOLR1 active agent, comprises: (a) detecting the level of FOLR1 expression in a cancerous sample from the cancer using an antibody, antigen-binding fragment thereof, polypeptide, or composition provided herein, wherein the detecting comprises the use of a method that specifically stains membrane FOLR1 in a FOLR1 expressing cancerous sample as compared to membrane FOLR1 in one or more reference samples; (b) determining a FOLR1 score for the cancerous sample; and (c) comparing the FOLR1 score determined in step (b) to a relative value determined by measuring FOLR1 in at least one reference sample, wherein the at least one reference sample is a tissue, cell, or cell pellet sample which is sensitive to treatment with an active agent comprising an anti-FOLR1 antibody or antigen-binding fragment thereof and wherein a FOLR1 score for the cancerous sample determined in step (b) that is greater than or equal to the relative value identifies the cancer as being sensitive to treatment with the active agent.

In some embodiments, the method further comprises administering an active agent comprising an anti-FOLR1 antibody or antigen-binding fragment thereof to the subject from whom the cancerous sample or biological sample was obtained.

In some embodiments, the patient's FOLR1 level is detected in a cancerous sample or biological sample obtained from the patient. In some embodiments, the cancerous sample or biological sample is a bodily fluid, cell, or tissue sample. In some embodiments, the cell is a circulating tumor cell. In some embodiments, the bodily fluid is blood, ascites, urine, plasma, serum, or peripheral blood.

In some embodiments, the FOLR1 is membrane localized FOLR1.

In some embodiments, the FOLR1 is shed FOLR1.

In some embodiments, the detecting is by enzyme linked immunosorbent assay (ELISA).

In some embodiments, the detecting is by immunohistochemistry (IHC). In some embodiments, the IHC is calibrated IHC that can distinguish different levels of FOLR1 expression. In some embodiments, the IHC produces a range of staining intensity for samples having low cell surface FOLR1 expression, intermediate FOLR1 cell surface expression, or high FOLR1 cell surface expression. In some embodiments, the IHC distinguishes between staining intensity and staining uniformity in a FOLR1 expressing cancerous sample or biological sample as compared to a reference sample. In some embodiments, the IHC detects membrane FOLR1. In some embodiments, the IHC is performed manually. In some embodiments, the IHC is performed using an automated system.

In some embodiments, a FOLR1 score is determined from the IHC.

In some embodiments, a score of at least 1 indicates an increased expression of FOLR1 and identifies the cancer as likely to respond to an active agent comprising an anti-FOLR1 antibody or antigen-binding fragment thereof.

In some embodiments, a score of at least 2, at least 2 homo (>75% uniformity), or at least 2 hetero (25-75% uniformity) identifies the cancer as likely to respond to an active agent comprising an anti-FOLR1 antibody or antigen-binding fragment thereof. In some embodiments, the cancer is lung cancer or endometrial cancer. In some embodiments, a score of at least 3, at least 3 homo (>75% uniformity), or at least 3 hetero (25-75% uniformity) identifies the cancer as likely to respond to an active agent comprising an anti-FOLR1 antibody or antigen-binding fragment thereof. In some embodiments, the cancer is lung cancer, endometrial cancer, or ovarian cancer.

In some embodiments, an H-score of at least 50 identifies a cancer as likely to respond to an active agent comprising an anti-FOLR1 antibody or antigen-binding fragment thereof. In some embodiments, an H-score of at least 75 identifies an ovarian cancer as likely to respond to an active agent comprising an anti-FOLR1 antibody or antigen-binding fragment thereof. In some embodiments, an H-score of at least 50 identifies an NSCLC as likely to respond to an active agent comprising an anti-FOLR1 antibody or antigen-binding fragment thereof. In some embodiments, an H-score of at least 50 identifies an endometrial cancer as likely to respond to an active agent comprising na anti-FOLR1 antibody or antigen-binding fragment thereof. In one embodiment, an H-score is determined using the FOLR1-2.1 antibody.

In some embodiments, at least 25% of FOLR1 membrane expression in an ovarian tumor sample with an intensity of at least 3 identifies the ovarian cancer as likely to respond to an active agent comprising an anti-FOLR1 antibody or antigen-binding fragment thereof. In some embodiments, at least 25% of FOLR1 membrane expression in an NSCLC sample with an intensity of at least 2 identifies the NSCLC as likely to respond to an active agent comprising an anti-FOLR1 antibody or antigen-binding fragment thereof. In some embodiments, at least 25% of FOLR1 membrane expression in an endometrial tumor sample with an intensity of at least 2 identifies the endometrial cancer as likely to respond to an active agent comprising an anti-FOLR1 antibody or antigen-binding fragment thereof. In one embodiment, the expression score is determined using the FOLR1-2.1 antibody.

In some embodiments, a score of at least 1 indicates an increased expression of FOLR1 and that the patient will benefit from administration of an active agent comprising an anti-FOLR1 antibody or antigen-binding fragment thereof. In some embodiments, a score of at least 2, at least 2 homo (>75% uniformity), or at least 2 hetero (25-75% uniformity) indicates that the patient will benefit from administration of an active agent comprising an anti-FOLR1 antibody or antigen-binding fragment thereof. In some embodiments, the cancer is lung cancer or endometrial cancer. In some embodiments, a score of at least 3, at least 3 homo (>75% uniformity), or at least 3 hetero (25-75% uniformity) indicates that the patient will benefit from administration of an active agent comprising an anti-FOLR1 antibody or antigen-binding fragment thereof. In some embodiments, the cancer is lung cancer, endometrial cancer, or ovarian cancer.

In some embodiments, an H-score of at least 50 indicates that the patient will benefit from administration of an active agent comprising an anti-FOLR1 antibody or antigen-binding fragment thereof. In some embodiments, an H-score of at least 75 indicates that a patient with ovarian cancer will benefit from administration of an active agent comprising an anti-FOLR1 antibody or antigen-binding fragment thereof. In some embodiments, an H-score of at least 50 indicates that a patient with NSCLC will benefit from administration of an active agent comprising an anti-FOLR1 antibody or antigen-binding fragment thereof. In some embodiments, an H-score of at least 50 indicates that a patient with endometrial cancer will benefit from administration of an active agent comprising an anti-FOLR1 antibody or antigen-binding fragment thereof. In one embodiment, an H-score is determined using the FOLR1-2.1 antibody.

In some embodiments, at least 25% of FOLR1 membrane expression in a ovarian tumor sample with an intensity of at least 3 indicates that the patient will benefit from administration of an active agent comprising an anti-FOLR1 antibody or antigen-binding fragment thereof. In some embodiments, at least 25% of FOLR1 membrane expression in an NSCLC sample with an intensity of at least 2 indicates that the patient will benefit from administration of an active agent comprising an anti-FOLR1 antibody or antigen-binding fragment thereof. In some embodiments, at least 25% of FOLR1 membrane expression in an endometrial tumor sample with an intensity of at least 2 indicates that the patient will benefit from administration of an active agent comprising an anti-FOLR1 antibody or antigen-binding fragment thereof. In one embodiment, the expression score is determined using the FOLR1-2.1 antibody.

In some embodiments, a score of at least 1 indicates an increased expression of FOLR1. In some embodiments, a score of at least 2, at least 2 homo (>75% uniformity), or at least 2 hetero (25-75% uniformity) indicates a decreased dose of the active agent should be administered. In some embodiments, the cancer is lung cancer or endometrial cancer. In some embodiments, a score of at least 3, at least 3 homo (>75% uniformity), or at least 3 hetero (25-75% uniformity) indicates a decreased dose of the active agent should be administered. In some embodiments, the cancer is lung cancer, endometrial cancer, or ovarian cancer.

In some embodiments, a score of at least 1 indicates an increased expression of FOLR1. In some embodiments, a score of at least 2, at least 2 homo (>75% uniformity), or at least 2 hetero (25-75% uniformity) identifies the cancer as likely to respond to a low dose anti-FOLR1 treatment. In some embodiments, the cancer is lung cancer or endometrial cancer. In some embodiments, a score of at least 3, at least 3 homo (>75% uniformity), or at least 3 hetero (25-75% uniformity) identifies the cancer as likely to respond to a low dose anti-FOLR1 treatment. In some embodiments, the cancer is lung cancer, endometrial cancer, or ovarian cancer.

In some embodiments, a score of at least 2, at least 2 homo (>75% uniformity), or at least 2 hetero (25-75% uniformity) identifies the cancer as being sensitive to treatment with an active agent comprising an anti-FOLR1 antibody or antigen-binding fragment thereof. In some embodiments, the cancer is lung cancer or endometrial cancer. In some embodiments, a score of at least 3, at least 3 homo (>75% uniformity), or at least 3 hetero (25-75% uniformity) identifies the cancer as being sensitive to treatment with an active agent comprising an anti-FOLR1 antibody or antigen-binding fragment thereof. In some embodiments, the cancer is lung cancer, endometrial cancer, or ovarian cancer.

In some embodiments, an H-score of at least 50 identifies a cancer as being sensitive to treatment with an active agent comprising an anti-FOLR1 antibody or antigen-binding fragment thereof. In some embodiments, an H-score of at least 75 identifies an ovarian cancer as being sensitive to treatment with an active agent comprising an anti-FOLR1 antibody or antigen-binding fragment thereof. In some embodiments, an H-score of at least 50 identifies an NSCLC as being sensitive to treatment with an active agent comprising an anti-FOLR1 antibody or antigen-binding fragment thereof. In some embodiments, an H-score of at least 50 identifies an endometrial cancer as being sensitive to treatment with an active agent comprising an anti-FOLR1 antibody or antigen-binding fragment thereof. In one embodiment, an H-score is determined using the FOLR1-2.1 antibody.

In some embodiments, at least 25% of FOLR1 membrane expression in a ovarian tumor sample with an intensity of at least 3 identifies the cancer as being sensitive to treatment with an active agent comprising an anti-FOLR1 antibody or antigen-binding fragment thereof. In some embodiments, at least 25% of FOLR1 membrane expression in an NSCLC sample with an intensity of at least 2 identifies the cancer as being sensitive to treatment with an active agent comprising an anti-FOLR1 antibody or antigen-binding fragment thereof. In some embodiments, at least 25% of FOLR1 membrane expression in an endometrial tumor sample with an intensity of at least 2 identifies the cancer as being sensitive to treatment with an active agent comprising an anti-FOLR1 antibody or antigen-binding fragment thereof. In one embodiment, the expression score is determined using the FOLR1-2.1 antibody.

In some embodiments, the reference sample is a positive reference sample or a negative reference sample. In some embodiments, the reference sample comprises cells, cell pellets, or tissue.

In some embodiments, the antibody, antigen-binding fragment thereof, or polypeptide of comprises a detection reagent selected from the group consisting of: an enzyme, a fluorophore, a radioactive label, and a luminophore. In some embodiments, the detection reagent is selected from the group consisting of: biotin, digoxigenin, fluorescein, tritium, and rhodamine.

In some embodiments, the cancer is a FOLR1 positive cancer. In some embodiments, the cancer is selected from the group consisting of ovarian, brain, breast, uterine, endometrial, pancreatic, renal, and lung cancer. In some embodiments, the lung cancer is non small cell lung cancer or bronchioloalveolar carcinoma. In some embodiments, the ovarian cancer is epithelial ovarian cancer. In some embodiments, the ovarian cancer is platinum resistant, relapsed, or refractory.

In some embodiments, FOLR1 expression is detected using at least one additional anti-FOLR1 antibody or antigen-binding fragment thereof. In some embodiments, FOLR1 expression is measured using two anti-FOLR1 antibodies or antigen-binding fragments thereof. In some embodiments, at least one antibody or antigen-binding fragment thereof is bound to a solid support. In some embodiments, at least one antibody or antigen-binding fragment thereof is bound to a microtiter plate.

In some embodiments, at least one additional antibody or antigen-binding fragment thereof comprises a detection agent. In some embodiments, the detection agent is a chromogenic detection agent, a fluorogenic detection agent, an enzymatic detection agent, or an electrochemiluminescent detection agent. In some embodiments, the detection agent is horseradish peroxidase (HRP).

In some embodiments, the ELISA is a sandwich ELISA.

In some embodiments, the active agent comprises the FOLR1 antibody huMov19. In some embodiments, the active agent is an antibody maytansinoid conjugate comprising the FOLR1 antibody huMov19 (comprising a heavy chain variable region of SEQ ID NO:45 and a light chain variable region of SEQ ID NO:47), the maytansinoid DM4, and the cleavable sulfo-SPDB linker (IMGN853).

In some embodiments, a method for identifying a cancer as likely to respond to treatment with an antibody maytansinoid conjugate comprising the FOLR1 antibody huMov19, the maytansinoid DM4 and a sulfo-SPDB linker (IMGN853), comprises measuring FOLR1 using an antibody comprising a heavy chain comprising the amino acids of SEQ ID NO:27 and a light chain comprising the amino acids of SEQ ID NO:28 in an IHC assay, wherein a score of at least 2 hetero indicates the cancer is likely to responds to the treatment.

In some embodiments, a method for identifying a cancer as likely to respond to treatment with an antibody maytansinoid conjugate comprising the FOLR1 antibody huMov19, the maytansinoid DM4 and a sulfo-SPDB linker (IMGN853), comprises measuring FOLR1 using an antibody comprising a heavy chain comprising the amino acids of SEQ ID NO:27 and a light chain comprising the amino acids of SEQ ID NO:28 in an IHC assay, wherein a score of at least 1 indicates the cancer is likely to responds to the treatment.

In some embodiments, an article of manufacture provided herein comprises a therapeutic active agent comprising an anti-FOLR1 antibody or antigen-binding fragment thereof described herein, a container, and a package insert or label indicating that the active agent can be used to treat a cancer characterized by the increased expression of FOLR1. In some embodiments, an article of manufacture provided herein comprises a therapeutic active agent comprising an anti-FOLR1 antibody or antigen-binding fragment thereof described herein, a container, and a package insert or label indicating that the active agent can be used to treat a cancer characterized by the expression of FOLR1 at a level of 2, or 3 measured using an antibody, antigen-binding fragment thereof, polypeptide, or composition provided herein. In some embodiments, the anti-FOLR1 antibody of the active agent is conjugated to a cytotoxin. In some embodiments, the package insert or label indicates that the active agent can be used to treat a cancer characterized by the expression of FOLR1 at a level of at least 1. In some embodiments, the package insert or label indicates that the active agent can be used to treat a cancer characterized by the expression of FOLR1 at a level of at least 2, at least 2 homo (>75% uniformity), or at least 2 hetero (25-75% uniformity). In some embodiments, the cancer is lung cancer or endometrial cancer. In some embodiments, the package insert or label indicates that the active agent can be used to treat a cancer characterized by the expression of FOLR1 at a level of at least 3, at least 3 homo (>75% uniformity), or at least 3 hetero (25-75% uniformity). In some embodiments, the cancer is lung cancer, endometrial cancer, or ovarian cancer.

In some embodiments, a combination diagnostic and pharmaceutical kit provided herein comprises an antibody, antigen-binding fragment thereof, polypeptide, or composition provided herein for use in diagnosis and an active agent comprising an anti-FOLR1 antibody or antigen-binding fragment thereof for use in therapy. In some embodiments, the detection antibody is able to detect FOLR1 expression by IHC. In some embodiments, the detection antibody is able to detect FOLR1 expression by ELISA. In some embodiments, the anti-FOLR1 antibody in the active agent is conjugated to a cytotoxin.

In some embodiments, a diagnostic kit provided herein comprises an antibody, antigen-binding fragment thereof or polypeptide provided herein, a reagent for immunohistochemistry (IHC), and one or more standardized reference samples, wherein the standardized reference samples comprise cells, cell pellets, or formalin fixed paraffin embedded tissue samples, and wherein the one or more standardized referenced samples are from non-FOLR1 expressing, low-FOLR1 expressing, or high FOLR1 expressing cells, cell pellets, or tissues.

In some embodiments, an immunoassay kit for detecting shed FOLR1 in a sample comprises: (a) an antibody, antigen-binding fragment thereof, polypeptide, or composition provided herein, and (b) a detection reagent. In some embodiments, the kit further comprises a solid support for the capture reagent. In some embodiments, the capture reagent is immobilized on the solid support. In some embodiments, the capture reagent is coated on a microtiter plate. In some embodiments, the detection reagent is a second FOLR1 antibody. In some embodiments, the detection reagent is detected using a species specific antibody. In some embodiments, the kit further comprises a detection means for the detection reagent. In some embodiments, the detection means is colorimetric. In some embodiments, the kit further comprises a FOLR1 polypeptide as an antigen standard. In some embodiments, the FOLR1 polypeptide is FOLR1-Fc.

Active agents are also provided herein. In some embodiments, an active agent comprises an anti-FOLR1 antibody or antigen-binding fragment thereof for use in a method for treating cancer, wherein said active agent is administered to a subject having cancer, wherein increased expression of FOLR1 has been detected in a cancerous sample obtained from said subject using an antibody, antigen-binding fragment thereof, polypeptide or composition provided herein.

In some embodiments, an active agent comprises an anti-FOLR1 antibody or antigen-binding fragment thereof for use in a method for treating cancer, comprising: (a) determining a FOLR1 expression score from a detection of FOLR1 expression in a cancerous sample obtained from the patient, wherein the detection is performed using an antibody, antigen-binding fragment thereof, polypeptide, or composition provided herein; and (b) administering an active agent comprising an anti-FOLR1 antibody or antigen-binding fragment thereof to the patient if the score indicates the patient will benefit from administration of the active agent.

In some embodiments, an active agent comprises an anti-FOLR1 antibody or antigen-binding fragment thereof for use in a method for treating cancer, comprising: (a) determining a FOLR1 expression score from a detection of FOLR1 expression in a cancerous sample obtained from the patient, wherein the detection is performed using an antibody, antigen-binding fragment thereof, polypeptide, or composition provided herein; and (b) instructing a healthcare provider to administer an active agent comprising an anti-FOLR1 antibody or antigen-binding fragment thereof to the patient if the score indicates the patient will benefit from administration of the active agent.

In some embodiments, an active agent comprises an anti-FOLR1 antibody or antigen-binding fragment thereof for use in a method for treating cancer, comprising: (a) submitting a cancerous sample obtained from a patient having cancer for determining a FOLR1 expression score from a detection of FOLR1 expression using the antibody, antigen-binding fragment thereof, polypeptide, or composition provided herein; and (b) administering an active agent comprising an anti-FOLR1 antibody or antigen-binding fragment thereof to the patient if the score indicates the patient will benefit from administration of the active agent.

In some embodiments, an active agent comprises an anti-FOLR1 antibody or antigen-binding fragment thereof for use in a method for treating cancer, comprising: (a) detecting FOLR1 expression in a cancerous sample obtained from said patient, wherein the detection is performed using the antibody, antigen-binding fragment thereof, polypeptide, or composition provided herein; (b) determining a FOLR1 expression score for said cancerous sample; and (c) administering an active agent comprising an anti-FOLR1 antibody or antigen-bidning fragment thereof to the patient if the score indicates the patient will benefit from administration of the active agent.

In some embodiments, an active agent comprises an anti-FOLR1 antibody or antigen-binding fragment thereof for use in a method for treating cancer, comprising: (a) administering to a patient a fixed dose of an active agent comprising an anti-FOLR1 antibody or antigen-binding fragment thereof; (b) detecting the FOLR1 expression level in a cancerous sample obtained from the patient relative to the FOLR1 level in a reference sample, wherein the detection is performed using an antibody, antigen-binding fragment thereof, polypeptide, or composition provided herein; and (c) increasing the amount or frequency of subsequent fixed doses if the patient's FOLR1 level is elevated.

In some embodiments, an active agent comprises an anti-FOLR1 antibody or antigen-binding fragment thereof for use in a method for treating cancer, comprising the step of optimizing the therapeutic regimen of said active agent comprising: (a) administering an increased dose of an active agent comprising an anti-FOLR1 antibody or antigen-binding fragment thereof to a subject having cancer wherein an increased expression of FOLR1 in a cancerous sample from said subject has been detected using the antibody, antigen-binding fragment thereof, polypeptide, or composition provided herein; or (b) administering a decreased dose of the active agent to a subject having cancer wherein a decreased expression of FOLR1 in a cancerous sample from said subject has been detected.

In some embodiments, an active agent comprises an anti-FOLR1 antibody or antigen-binding fragment thereof for use in a method for treating cancer, comprising the step of optimizing the therapeutic regimen of said active agent comprising: (a) detecting the level of FOLR1 expression in a cancerous sample from said subject using an antibody, antigen-binding fragment thereof, polypeptide, or composition provided herein; (b) determining a FOLR1 expression score for said cancerous sample; and (c) administering an increased dose of an active agent comprising an anti-FOLR1 antibody or antigen-binding fragment thereof to the subject if the score is low or administering a decreased dose of the active agent to the subject if the score is high.

In some embodiments, an active agent comprises an anti-FOLR1 antibody or antigen-binding fragment thereof for use in a method for treating cancer, wherein FOLR1-expressing cancer cells in a cancer patient are decreased, wherein: (a) the FOLR1 level in a cancerous sample obtained from a patient is detected by comparing it to the FOLR1 level in a reference sample using an antibody, antigen-binding fragment thereof, polypeptide, or composition provided herein; and (b) a fixed dose of the active agent is administered to the patient if the patient's FOLR1 level is elevated; wherein the administration of the active agent decreases the number of FOLR1-expressing cancer cells in the patient.

In some embodiments, an active agent comprises an anti-FOLR1 antibody or antigen-binding fragment thereof for use in a method for treating cancer, wherein FOLR1-expressing cancer cells in a cancer patient are decreased, wherein: (a) a fixed dose of the active agent is administered to a patient having a cancer; (b) the FOLR1 level in a cancerous sample obtained from the patient is detected relative to the FOLR1 level in a reference sample using an antibody, antigen-binding fragment thereof, polypeptide, or composition provided herein; and (c) the amount or frequency of subsequent fixed doses is increased if the patient's FOLR1 level is elevated compared to the reference sample; wherein the administration of the active agent decreases the number of FOLR1-expressing cancer cells in the patient.

Anti-FOLR1 antibodies and antigen-binding fragments thereof for uses is methods of monitoring and methods of diagnosing are also provided herein. In some embodiments, an anti-FOLR1 antibody or antigen-binding fragment thereof for use in a method for monitoring the therapeutic efficacy of a fixed dose of the active agent in a patient comprises: (a) detecting a first FOLR1 level in a biological sample from a patient having cancer using an antibody, antigen-binding fragment thereof, polypeptide, or composition provided herein; (b) administering to the patient a fixed dose of the active agent; (c) detecting a second FOLR1 level in a biological sample from the patient following active agent administration, wherein the detecting is performed using an antibody, antigen-binding fragment thereof, polypeptide, or composition provided herein; and (d) comparing the second FOLR1 level to the first FOLR1 level; wherein a decrease between the first and second FOLR1 level indicates therapeutic efficacy.

In some embodiments, an anti-FOLR1 antibody or antigen-binding fragment thereof for use in a method for diagnosing whether a subject having cancer is likely to respond to a low dose anti-FOLR1 treatment regimen, comprises: (a) contacting a biological sample comprising cells from said cancer with an antibody, antigen-binding fragment thereof, polypeptide, or composition provided herein; (b) detecting binding of said antibody, antigen-binding fragment, or polypeptide to said biological sample of (a); (c) assigning a score to said binding of step (b), wherein said score is assigned based on comparison to one or more reference samples; and (d) comparing said score in step (c) to the score of a reference tissue or cell, wherein a score for said cancer FOLR1 level that is greater than the score for a normal or low FOLR1 expressing reference sample or a score for said cancer FOLR1 level that is equal to or greater than the score for a high FOLR1 expressing reference sample identifies said cancer as likely to respond to a low dose of an active agent comprising an anti-FOLR1 antibody or antigen-binding fragment thereof.

In some embodiments, an anti-FOLR1 antibody or antigen-binding fragment thereof for use in a method for diagnosing whether a cancer is sensitive to treatment with an anti-FOLR1 treatment, comprises: (a) detecting the level of FOLR1 expression in a cancerous sample from said cancer using an antibody, antigen-binding fragment thereof, polypeptide, or composition provided herein, wherein said detecting comprises the use of a method that distinguishes between staining intensity or staining uniformity in a FOLR1 expressing cancerous sample as compared to staining intensity or staining uniformity in one or more reference samples; (b) determining a FOLR1 staining intensity or staining uniformity score for said cancerous sample; and (c) comparing the FOLR1 staining intensity or staining uniformity score determined in step (b) to a relative value determined by measuring FOLR1 protein expression in at least one reference sample, wherein said at least one reference sample is a tissue, cell, or cell pellet sample which is not sensitive to treatment with an active agent comprising an anti-FOLR1 antibody or antigen-binding fragment thereof and wherein a FOLR1 staining intensity score for said cancerous sample determined in step (b) that is higher than said relative value identifies said cancer as being sensitive to treatment with the active agent.

In some embodiments, an anti-FOLR1 antibody or antigen-binding fragment thereof for use in a method for diagnosing whether a cancer is sensitive to treatment with an anti-FOLR1 treatment, comprising: (a) detecting the level of FOLR1 expression in a cancerous sample from said cancer using an antibody, antigen-binding fragment thereof, polypeptide, or composition provided herein, wherein said detecting comprises the use of a method that distinguishes between staining intensity or staining uniformity in a FOLR1 expressing cancerous sample as compared to staining intensity or staining uniformity in one or more reference samples; (b) determining a FOLR1 staining intensity or staining uniformity score for said cancerous sample; and (c) comparing the FOLR1 staining intensity or staining uniformity score determined in step (b) to a relative value determined by measuring FOLR1 protein expression in at least one reference sample, wherein said at least one reference sample is a tissue, cell, or cell pellet sample which is sensitive to treatment with an active agent comprising an anti-FOLR1 antibody or antigen-binding fragment thereof and wherein a FOLR1 staining intensity score for said cancerous sample determined in step (b) that is higher than said relative value identifies said cancer as being sensitive to treatment with the active agent.

In some embodiments, the use of the active agents or anti-FOLR1 antibodies or antigen-binding fragments thereof further comprises administering an active agent comprising an anti-FOLR1 antibody or antigen-fragment thereof to the subject from whom the cancerous sample or biological sample was obtained.

In some embodiments, the cancerous sample or biological sample is a bodily fluid, cell, or tissue sample. In some embodiments, the cell is a circulating tumor cell. In some embodiments, the bodily fluid is blood, ascites, urine, plasma, serum, or peripheral blood.

In some embodiments of the active agents or anti-FOLR1 antibodies or antigen-binding fragments thereof, the detecting is by enzyme linked immunosorbent assay (ELISA) and/or by immunohistochemistry (IHC). In some embodiments, the IHC is calibrated IHC that can distinguish different levels of FOLR1 expression. In some embodiments, the IHC produces a range of staining intensity for samples having low cell surface FOLR1 expression, intermediate FOLR1 cell surface expression, or high FOLR1 cell surface expression. In some embodiments, the IHC distinguishes between staining intensity and staining uniformity in a FOLR1 expressing cancerous sample or biological sample as compared to a reference sample. In some embodiments, IHC is performed manually. In some embodiments, the IHC is performed using an automated system. In some embodiments, a FOLR1 score is determined from the IHC. In some embodiments, the IHC with an antibody or antigen-binding fragment described herein produces a range of staining for cells that have increased FOLR1 expression, particularly those within the level of staining equal to or greater than 2.

In some embodiments, a score of at least 2 indicates that the patient will benefit from administration of an active agent comprising an anti-FOLR1 antibody or antigen-binding fragment thereof. In some embodiments, a score of at least 2 homo (>75% uniformity) or at least 2 hetero (25-75% uniformity) indicates that the patient will benefit from administration of an active agent comprising an anti-FOLR1 antibody or antigen-binding fragment thereof. In some embodiments, the cancer is lung cancer or endometrial cancer.

In some embodiments, a score of at least 3 indicates that the patient will benefit from administration of an active agent comprising an anti-FOLR1 antibody or antigen-binding fragment thereof. In some embodiments, a score of at least 3 homo (>75% uniformity) or at least 3 hetero (25-75% uniformity) indicates that the patient will benefit from administration of an active agent comprising an anti-FOLR1 antibody or antigen-binding fragment thereof. In some embodiments, the cancer is lung cancer, endometrial cancer, or ovarian cancer.

In some embodiments, a score of at least 2 indicates that the patient will benefit from administration of an active agent comprising an anti-FOLR1 antibody or antigen-binding fragment thereof In some embodiments, a score of at least 2 homo (>75% uniformity) or at least 2 hetero (25-75% uniformity) indicates that the patient will benefit from administration of an active agent comprising an anti-FOLR1 antibody or antigen-binding fragment thereof. In some embodiments, the cancer is lung cancer, endometrial cancer, or ovarian cancer.

In some embodiments, a score of at least 2 indicates an a decreased dose of the active agent should be administered. In some embodiments, a score of at least 2 homo (>75% uniformity) or at least 2 hetero (25-75% uniformity) indicates an a decreased dose of the active agent should be administered. In some embodiments, the cancer is lung cancer, endometrial cancer, or ovarian cancer.

In some embodiments, a score of at least 2 identifies the cancer as likely to respond to a low dose anti-FOLR1 treatment. In some embodiments, a score of at least 2 homo (>75% uniformity) or 2 hetero (25-75% uniformity) identifies the cancer as likely to respond to a low dose anti-FOLR1 treatment. In some embodiments, the cancer is lung cancer or endometrial cancer.

In some embodiments, a score of at least 3 identifies the cancer as likely to respond to a low dose anti-FOLR1 treatment. In some embodiments, a score of at least 3 homo (>75% uniformity) or at least 3 hetero (25-75% uniformity) identifies the cancer as likely to respond to a low dose anti-FOLR1 treatment. In some embodiments, the cancer is lung cancer, endometrial cancer, or ovarian cancer.

In some embodiments, a score of at least 2 identifies the cancer as likely to respond to a low dose anti-FOLR1 treatment. In some embodiments, a score of at least 2 homo (>75% uniformity) or at least 2 hetero (25-75% uniformity) identifies the cancer as likely to respond to a low dose anti-FOLR1 treatment. In some embodiments, the cancer is lung cancer, endometrial cancer, or ovarian cancer.

In some embodiments, a score of at least 2 identifies the cancer as being sensitive to treatment with an active agent comprising an anti-FOLR1 antibody or antigen-binding fragment thereof. In some embodiments, a score of at least 2 homo (>75% uniformity) or at least 2 hetero (25-75% uniformity) identifies the cancer as being sensitive to treatment with an active agent comprising an anti-FOLR1 antibody or antigen-binding fragment thereof. In some embodiments, the cancer is lung cancer or endometrial cancer.

In some embodiments, a score of at least 3 identifies the cancer as being sensitive to treatment with an active agent comprising an anti-FOLR1 antibody or antigen-binding fragment thereof. In some embodiments, a score of at least 3 homo (>75% uniformity) or at least 3 hetero (25-75% uniformity) identifies the cancer as being sensitive to treatment with an active agent comprising an anti-FOLR1 antibody or antigen-binding fragment thereof. In some embodiments, the cancer is lung cancer, endometrial cancer, or ovarian cancer.

In some embodiments, a score of at least 2 identifies the cancer as being sensitive to treatment with an active agent comprising an anti-FOLR1 antibody or antigen-binding fragment thereof. In some embodiments, a score of at least 2 homo (>75% uniformity) or at least 2 hetero (25-75% uniformity) identifies the cancer as being sensitive to treatment with an active agent comprising an anti-FOLR1 antibody or antigen-binding fragment thereof. In some embodiments, the cancer is lung cancer, endometrial cancer, or ovarian cancer.

In some embodiments, a reference sample is a positive reference sample or a negative reference sample. In some embodiments, the reference sample comprises cells, cell pellets, or tissue.

In some embodiments of the active agent or anti-FOLR1 antibody or antigen-binding fragment thereof for a use provided herein, the antibody, antigen-binding fragment, or polypeptide provided herein further comprises a detection reagent selected from the group consisting of: an enzyme, a fluorophore, a radioactive label, and a luminophore. In some embodiments, the detection reagent is selected from the group consisting of: biotin, digoxigenin, fluorescein, tritium, and rhodamine.

In some embodiments of the active agent or anti-FOLR1 antibody or antigen-binding fragment thereof for a use provided herein, the cancer is a FOLR1 positive cancer. In some embodiments, the cancer is selected from the group consisting of ovarian, brain, breast, uterine, endometrial, pancreatic, renal, and lung cancer. In some embodiments, the lung cancer is non small cell lung cancer or bronchioloalveolar carcinoma. In some embodiments, the ovarian cancer is epithelial ovarian cancer. In some embodiments, the ovarian cancer is platinum resistant, relapsed, or refractory.

In some embodiments of the active agent or anti-FOLR1 antibody or antigen-binding fragment thereof for a use provided herein, the FOLR1 expression is detected using at least one additional anti-FOLR1 antibody or antigen-binding fragment thereof. In some embodiments, the FOLR1 expression is measured using two anti-FOLR1 antibodies or antigen-binding fragments thereof. In some embodiments, at least one antibody or antigen-binding fragment thereof is bound to a solid support. In some embodiments, at least one antibody or antigen-binding fragment thereof is bound to a microtiter plate. In some embodiments, at least one antibody or antigen-binding fragment thereof comprises a detection agent. In some embodiments, the detection agent is a chromogenic detection agent, a fluorogenic detection agent, an enzymatic detection agent, or an electrochemiluminescent detection agent. In some embodiments, the detection agent is horseradish peroxidase (HRP). In some embodiments, the ELISA is a sandwich ELISA.

In some embodiments of the active agent or anti-FOLR1 antibody or antigen-binding fragment thereof for a use provided herein, the active agent comprises the FOLR1 antibody huMov19 or is the FOLR1 antibody huMov19. In some embodiments, the active agent is administered as an antibody maytansinoid conjugate further comprising the maytansinoid DM4 and the cleavable sulfo-SPDB linker (IMGN853).

In some embodiments, an antibody, antigen-binding fragment, polypeptide, or composition provided herein is for use as a diagnostic.

In some embodiments, an antibody, antigen-binding fragment, polypeptide, or composition provided herein is for use in a method for diagnosing cancer in a patient suffering therefrom. In some embodiments, the cancer is associated with elevated levels of FOLR1.

In some embodiments, the binding affinity of an antibody, antigen-binding fragment, or polypeptide is a binding affinity obtained in Example 3 and/or shown in FIGS. 4, 5, and/or 6.

BRIEF DESCRIPTIONS OF THE DRAWINGS

FIG. 1 provides images of IHC staining of NSCLC and ovarian endometrioid adenocarcinoma samples using the 353.2-1 and 353.9-20 antibodies.

FIG. 2 provides images of IHC staining of normal salivary gland and pancreas samples using the 353.2-1 and 353.9-20 antibodies.

FIG. 3 provides images of Western blots of cell lysates using the 353.9-21, 353.2-1, 353.3-8, and 353.5-7 antibodies.

Figure 6A:
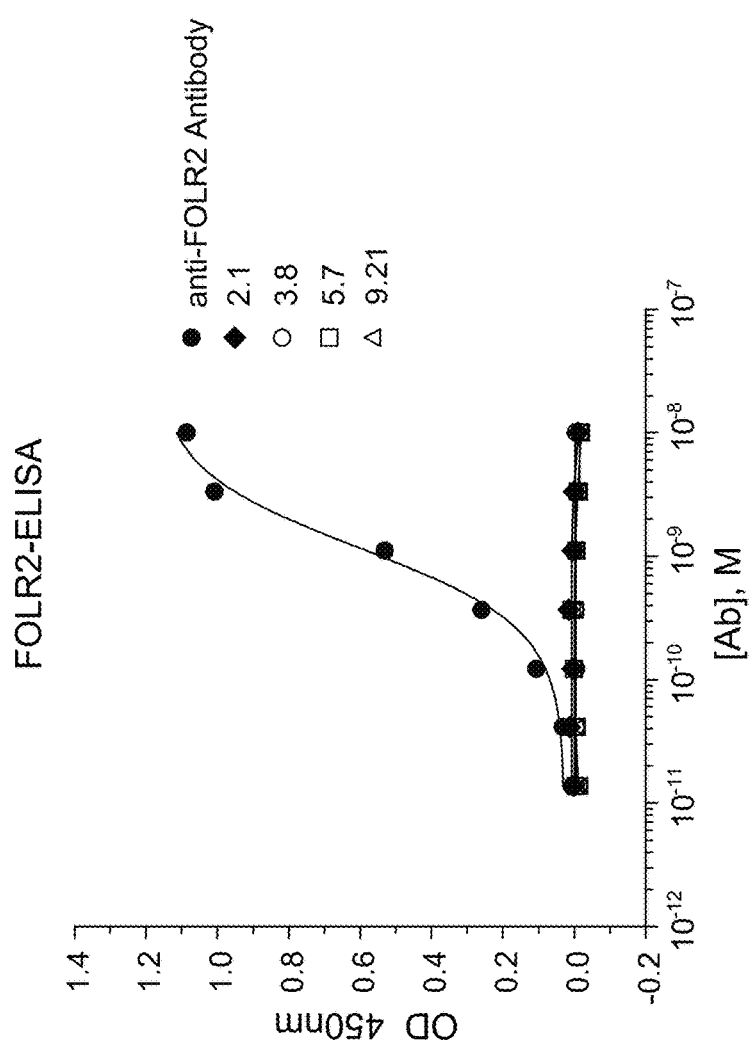
Figure 6B:
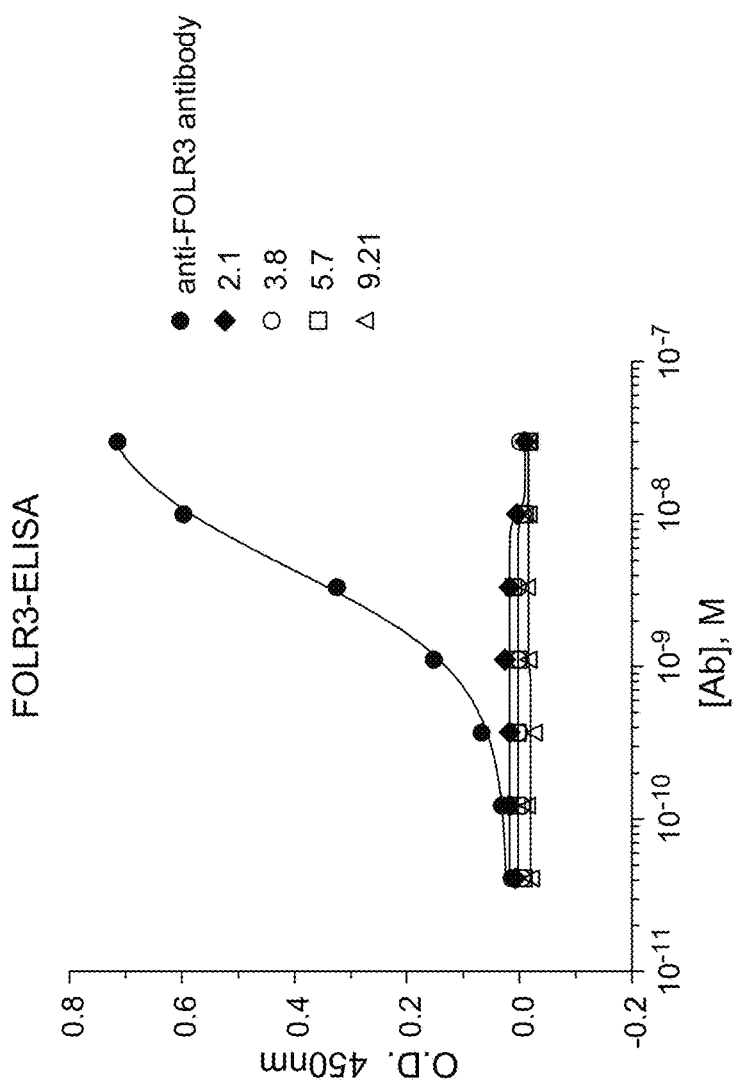

FIGS. 6A and 6B show the binding of an anti-FOLR2 antibody and 353.2-1, 353.3-1, 353.5-7, and 353.9-21 antibodies to FOLR2 (A) and the binding of an anti-FOLR3 antibody and 353.2-1, 353.3-1, 353.5-7, and 353.9-21 antibodies to FOLR3 (B) by ELISA.

FIG. 7 shows the binding of anti-FOLR1 antibodies 2.1 and huMov19 to deglycosylated and non-treated recombinant human FOLR1 by ELISA.

Figure 8:
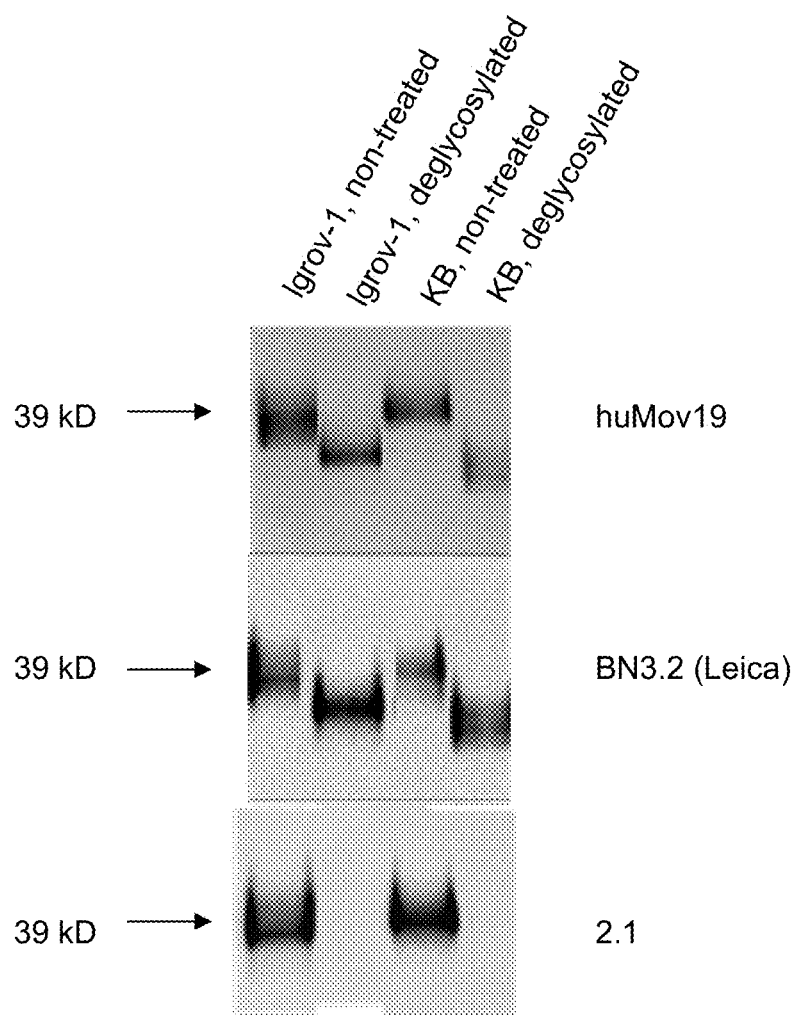

FIG. 8 shows the binding of anti-FOLR1 antibodies 2.1, huMov19, and BN3.2 to deglysolyated and non-treated lysates of KB and Igrov-1 cells by western blot analysis.

FIG. 9 shows the relevant amino acids for resurfacing of the anti-FOLR1 FRIHC2-1 antibody and the kabat position corresponding to each residue.

FIG. 10 shows the alignment of murine and humanized FRIHC2-1 antibody sequences for resurfacing. The murine heavy and light chain sequences correspond to SEQ ID NO:27 and SEQ ID NO:28, respectively. The resurfaced humanized heavy chain sequence corresponds to SEQ ID NO: 62, and the resurfaced human light chain version 1.0 and version 1.1 sequences correspond to SEQ ID NO:63 and SEQ ID NO:64, respectively. The leader "S" in the light chain sequence (framework position −1) is not considered for humanization and is not used in the humanized antibody sequence, so it is not shown in the figure.

FIG. 11 shows the relevant amino acids for CDR grafting of the anti-FOLR1 FRIHC2-1 antibody and the kabat position corresponding to each residue.

FIG. 12 shows the alignment of murine and humanized FRIHC2-1 sequences for CDR grafting. The murine heavy and light chain sequences correspond to SEQ ID NO:27 and SEQ ID NO:28, respectively. The grafted humanized heavy chain sequence corresponds to SEQ ID NO: 65, and the grafted human light chain version 1.0 and version 1.1 sequences correspond to SEQ ID NO:66 and SEQ ID NO:67, respectively. The leader "S" in the light chain sequence (framework position −1) is not considered for humanization and is not used in the humanized antibody sequence, so it is not shown in the figure.

Figure 13:
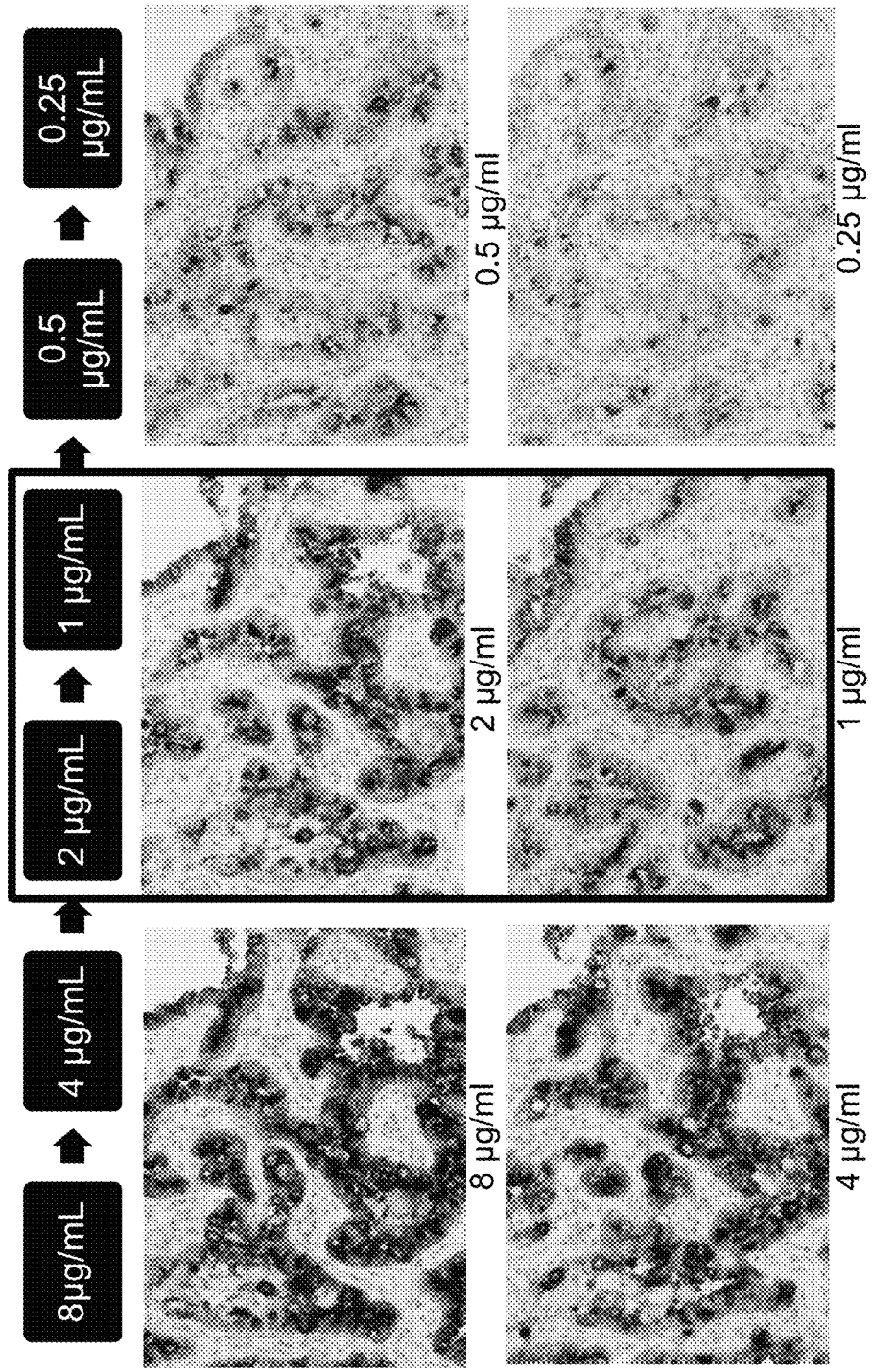

FIG. 13 provides images of IHC staining of lung adenocarcinoma tissues using the FOLR1-2.1 (353.2-1) antibody at varying dilutions.

FIGS. 14A, 14B, and 14C provide images of IHC staining of positive normal tissue (fallopian tube) (A) and cells (FOLR1 transfected cells (B)) and negative cells (untransfected cells (C)) using the FOLR1-2.1 (353-2.1) antibody.

FIGS. 15A and 15B provide images of IHC staining of ovarian cancer tissue (A) and lung adenocarcinoma tissue (B) samples using the FOLR1-2.1 (353-2.1) antibody.

Figure 16:
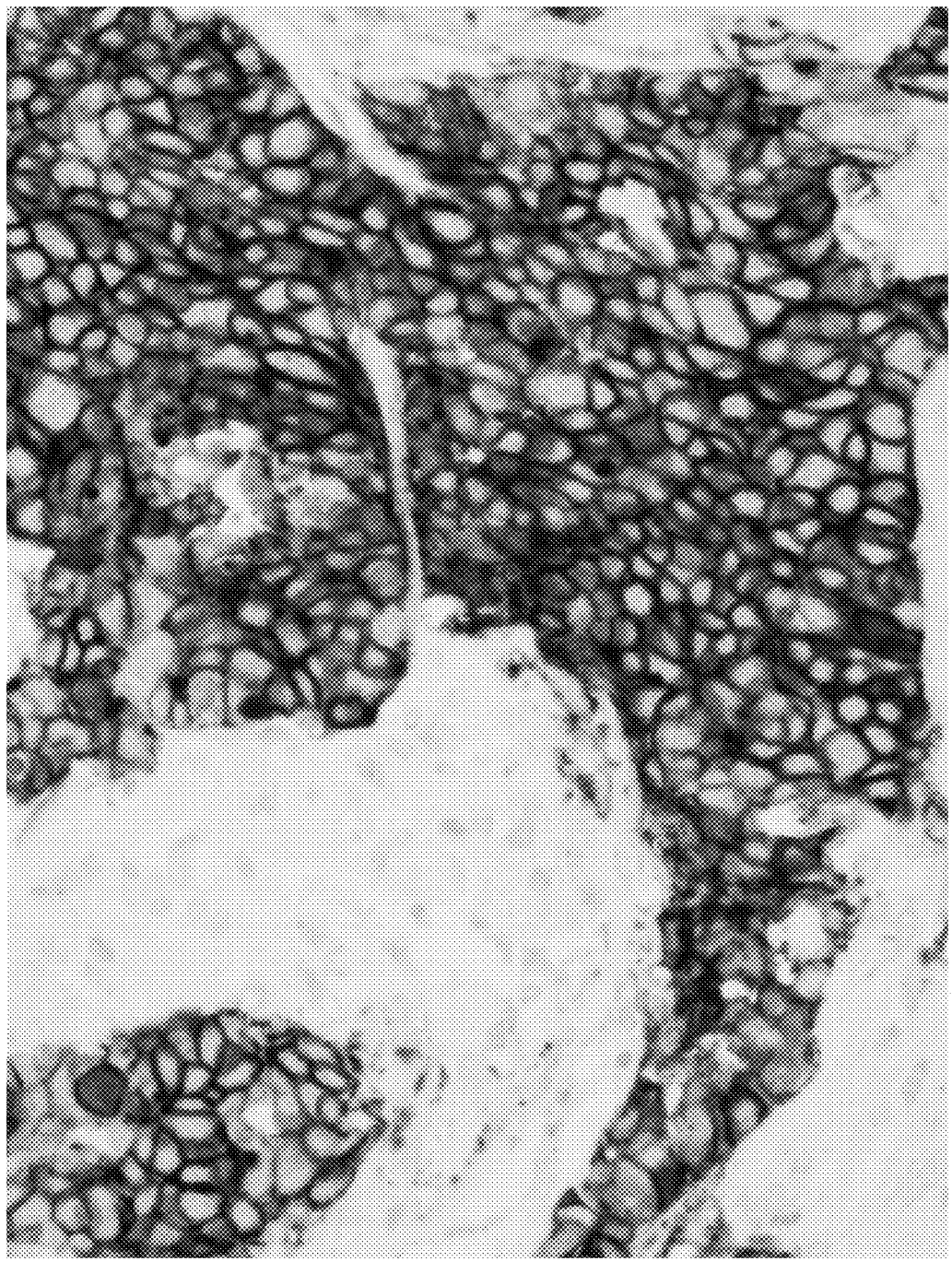

FIG. 16 shows membrane staining of tumor cells in an endometrial cancer sample with the FOLR1-2.1 assay. The stromal cells are not stained.

Figure 17:
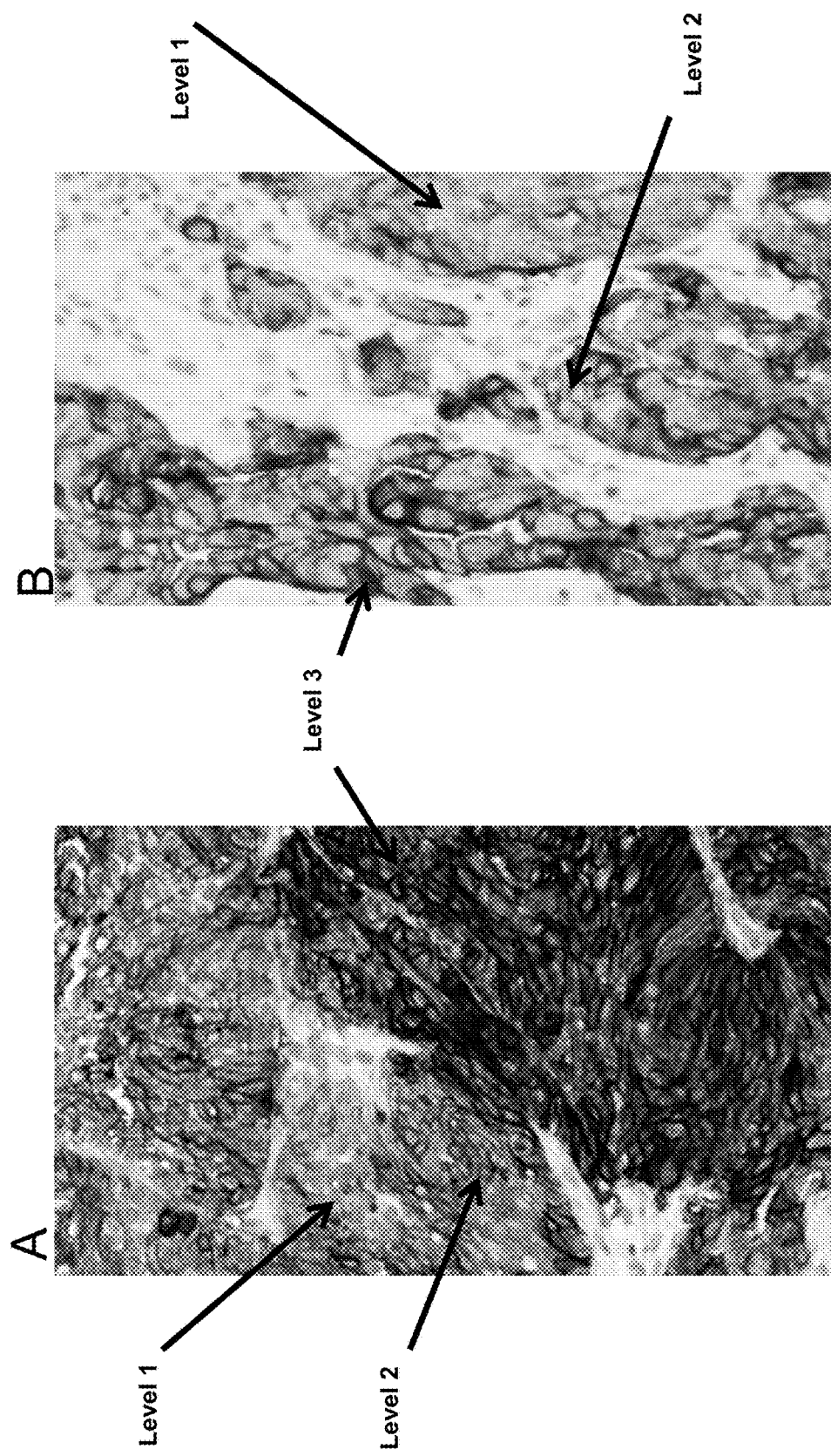

FIG. 17 shows a comparison of staining and scoring difference between (A) the FOLR1-2.1 assay and (B) the BN3.2 assay.

DETAILED DESCRIPTION OF THE INVENTION

The present disclosure provides methods of detecting human folate receptor 1 (FOLR1), including membrane FOLR1, shed FOLR1, and FOLR1 on circulating tumor cells, and improving the efficacy of or the likelihood of response to the treatment of cancers characterized by the overexpression of FOLR1. The detection methods can detect a clinically relevant dynamic range of FOLR1 and therefore can be used for patient stratification, to monitor or determine therapeutic efficacy, or the likelihood of response to the treatment of cancers characterized by the over expression of FOLR1. Novel FOLR1-binding polypeptides, such as antibodies, that are useful in the FOLR1 detection methods (e.g., IHC for membrane bound and cell associated FOLR1) are also disclosed. Related polypeptides and polynucleotides, compositions comprising the FOLR1-binding agents, and methods of making the FOLR1-binding agents are also provided.

I. Definitions

To facilitate an understanding of the present invention, a number of terms and phrases are defined below.

The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The term also encompasses naturally occurring variants of FOLR1 protein or nucleic acid, e.g., splice variants, allelic variants and isoforms. The FOLR1 polypeptides and polynucleotides described herein can be isolated from a variety of sources, such as from human tissue types or from another source, or prepared by recombinant or synthetic methods. Examples of FOLR1 sequences include, but are not limited to NCBI reference numbers P15328, NP_001092242.1, AAX29268.1, AAX37119.1, NP_057937.1, and NP_057936.1.

The terms "shed antigen" and "shed FOLR1" are used interchangeably herein. These terms refer to a FOLR1 protein that is soluble and that is not cell associated. In some embodiments it includes the extracellular domain (ECD) and the glycosylphatidyl inositol (GPI) linker. In one embodiment, the shed FOLR1 includes only the ECD. FOLR1 protein includes a signal peptide (amino acids 1-24), the FOLR1 protein chain (amino acids 25-233 or 234), and a propeptide which can be cleaved (amino acids 235 to 257). Mature FOLR1 protein lacks the signal peptide. Shed FOLR1 can include amino acids 1 to 257, 1 to 233, 1 to 234, 25 to 233, 25 to 234. or any other fragments thereof. In some embodiments the signal sequence is cleaved. In other embodiments the ECD and the GPI portion can be embedded in a membrane (e.g., a soluble lipid raft). In one embodiment, the shed FOLR1 can include amino acids 1-233 or a fragment thereof.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

In some embodiments, an antibody is a non-naturally occurring antibody. In some embodiments, an antibody is purified from natural components. In some embodiments, an antibody is recombinantly produced. In some embodiments, an antibody is produced by a hybridoma.

A "blocking" antibody or an "antagonist" antibody is one which inhibits or reduces biological activity of the antigen it binds, such as FOLR1. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-FOLR1 antibody" or "an antibody that binds to FOLR1" refers to an antibody that is capable of binding FOLR1 with sufficient affinity such that the antibody is useful as a diagnostic and/or therapeutic agent in targeting FOLR1. Unless otherwise specified, the extent of binding of an anti-FOLR1 antibody to an unrelated, non-FOLR1 protein is less than about 10% of the binding of the antibody to FOLR1 as measured, e.g., by a radioimmunoassay (RIA). In certain embodiments, an antibody that binds to FOLR1 has a dissociation constant (Kd) of ≤1 µM, ≤100 nM, ≤10 nM, ≤1 nM, or ≤0.1 nM. In one embodiment, the anti-FOLR1 antibody does not bind FOLR2, FOLR3, FOLR4, or folic acid. Examples of FOLR1 antibodies are known in the art and are disclosed in U.S. Published Application Nos. 2012/0009181 and 2012/0282175 and U.S. Provisional Application Nos. 61/695,791 and 61/756,254, and PCT publication WO2011/106528, each of which is herein incorporated by reference. The sequences of anti-FOLR1 antibodies and antigen-binding fragments thereof are provided in Tables 1-8.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR).

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641, Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody. In some embodiments, a "humanized antibody" is a CDR-grafted antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 ... 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd) or the half-maximal effective concentration (EC50). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described herein.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better," the antibody's affinity for the antigen is <0.6 nM, i.e., 0.59 nM, 0.58 nM, 0.57 nM etc. or any value less than 0.6 nM. In one embodiment, the antibody's affinity as determined by a Kd will be between about $10^{-3}$ to about $10^{-12}$ M, between about $10^{-6}$ to about $10^{-11}$ M, between about $10^{-6}$ to about $10^{-10}$ M, between about $10^{-6}$ to about $10^{-9}$ M, between about $10^{-6}$ to about $10^{-8}$ M, or between about $10^{-6}$ to about $10^{-7}$ M.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristics measured by said values (e.g., Kd values). The difference between said two values is less than about 50%, less than about 40%, less than about 30%, less than about 20%, or less than about 10% as a function of the value for the reference/comparator antibody.

The term "immunoconjugate" or "conjugate" as used herein refers to a compound or a derivative thereof that is linked to a cell binding agent (i.e., an anti-FOLR1 antibody or fragment thereof) and is defined by a generic formula: A-L-C, wherein C=cytotoxin, L=linker, and A=cell binding agent or anti-FOLR1 antibody or antibody fragment. Immunoconjugates can also be defined by the generic formula in reverse order: C-L-A.

A "linker" is any chemical moiety that is capable of linking a compound, usually a drug, such as a maytansinoid, to a cell-binding agent such as an anti-FOLR1 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "elevated" FOLR1, "increased expression" of FOLR1 and "overexpression" of FOLR1 refer to a sample which contains elevated levels of FOLR1 expression. The FOLR1 can be elevated, increased, or overexpressed as compared to a control value (e.g., expression level in a biological sample, tissue, or cell from a subject without cancer, a sample or cancer known to express no or low FOLR1, a normal sample, or a cancer that does not have elevated FOLR1 values). For example, a sample with increased expression can contain an increase of at least 2-fold, at least 3-fold, or at least 5-fold relative to a control values.

FOLR1 expression can be measured by immunohistochemistry and given a staining intensity score or a staining uniformity score by comparison to calibrated controls exhibiting defined scores (e.g., an intensity score of 3 is given to the test sample if the intensity is comparable to the level 3 calibrated control or an intensity of 2 is given to the test sample if the intensity is comparable to the level 2 calibrated control). For example, a score of 1, 2, or 3 (3+), preferably a score of 2, or 3 (3+), by immunohistochemistry indicates an increased expression of FOLR1. A staining uniformity that is heterogeneous or homogeneous is also indicative of FOLR1 expression. The staining intensity and staining uniformity scores can be used alone or in combination (e.g., 2 homo, 2 hetero, 3 homo, 3 hetero, etc.). See Table 11. In another example, an increase in FOLR1 expression can be determined by detection of an increase of at least 2-fold, at least 3-fold, or at least 5-fold relative to control values (e.g., expression level in a tissue or cell from a subject without cancer or with a cancer that does not have elevated FOLR1 values).

A "reference sample" can be used to correlate and compare the results obtained in the methods of the invention from a test sample. Reference samples can be cells (e.g., cell lines, cell pellets) or tissue. The FOLR1 levels in the "reference sample" can be an absolute or relative amount, a range of amount, a minimum and/or maximum amount, a mean amount, and/or a median amount of FOLR1. A "reference sample" can also serve as a baseline of FOLR1 expression to which the test sample is compared. The "reference sample" can include a prior sample or baseline sample from the same patient, a normal reference with a known level of FOLR1 expression, or a reference from a relevant patient population with a known level of FOLR1 expression. FOLR1 levels can also be expressed as values in a standard curve. A standard curve is a quantitative method of plotting assay data to determine the concentration of FOLR1 in a sample. In one embodiment, a reference sample is an antigen standard comprising purified FOLR1 or FOLR1-Fc. The diagnostic methods of the invention can involve a comparison between expression levels of FOLR1 in a test sample and a "reference value." In some embodiments, the reference value is the expression level of the FOLR1 in a reference sample. A reference value can be a predetermined value and can also be determined from reference samples (e.g., control biological samples or reference samples) tested in parallel with the test samples. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy. Examples of normal reference samples or values and positive reference samples or values are described herein and are also described in Examples 1 and Examples 8-10 of WO 2012/135675 herein incorporated by reference.

In some embodiments, the reference sample is a sample from a healthy tissue, in particular a corresponding tissue which is not affected by cancer or a corresponding tissue which is not affected by a cancer that overexpresses FOLR1 or a corresponding healthy tissue that is known not to express detectable levels of FOLR. These types of reference samples are referred to as negative control samples or "normal" reference samples. In other embodiments, the reference sample is a sample from a tumor or healthy tissue that expresses detectable FOLR1. These types of reference samples are referred to as positive control or positive reference samples. Positive control samples can also be used as a comparative indicator for the type (hetero versus homo) and/or degree (0, 1, 2, 3) of staining intensity, which correlates with the level of FOLR1 expression. Positive control comparative samples are also referred to as calibrated reference samples. Low or non-FOLR1 expressing references are described herein in the Examples and also include all structures of the esophagus, acinar cells/islets of the pancreas, interalveolar connective tissue of lung, and acinar cells of the salivary gland. For cell lines, exemplary non-expressors include BxPC3, Panc-1, and ASPC1. Positive FOLR1 references are described herein, for example, in the Examples and also include ducts of pancreas, respiratory epithelium of normal lung, and intercalated ducts of the salivary gland. In some embodiments, positive FOLR1 references include ducts of pancreas and intercalated ducts of the salivary gland. For cell lines, exemplary high FOLR1 expressors are described herein, for example, in the Examples and also include KB, HeLa, 300.19 cells transfected with FOLR1, Igrov-1, and Wish, and exemplary low FOLR1 expressors include Ovcar-3, Caov-3, SW620, T47D, and Skov-3. Another positive high FOLR1 reference is a cell line stably or transiently transfected with FOLR1. Additional positive and negative samples for FOLR1 are described in Table 13. Appropriate positive and negative reference levels of FOLR1 for a particular cancer can be determined by measuring levels of FOLR1 in one or more appropriate subjects, and such reference levels can be tailored to specific populations of subjects (e.g., a reference level can be age-matched so that comparisons can be made between FOLR1 levels in samples from subjects of a certain age and reference levels for a particular disease state, phenotype, or lack thereof in a certain age group). Such reference levels can also be tailored to specific techniques that are used to measure levels of FOLR1 in biological samples (e.g., immunoassays, etc.).

As used herein, "immunohistochemistry" refers to histochemical and immunologic methods used to analyze, for example, cells or tissues. Thus, the terms "immunohistochemistry," "immunocytochemistry," and "immunochemistry" are used interchangeably.

The term "primary antibody" herein refers to an antibody that binds specifically to the target protein antigen in a sample. A primary antibody is generally the first antibody used in an ELISA assay or IHC procedure. In one embodiment, the primary antibody is the only antibody used in an IHC procedure. The term "secondary antibody" herein refers to an antibody that binds specifically to a primary antibody, thereby forming a bridge or link between the primary antibody and a subsequent reagent, if any. The secondary antibody is generally the second antibody used in an immunohistochemical procedure.

A "sample" or "biological sample" of the present invention is of biological origin, in specific embodiments, such as from eukaryotic organisms. In some embodiments, the sample is a human sample, but animal samples may also be used. Non-limiting sources of a sample for use in the present invention include solid tissue, biopsy aspirates, ascites, fluidic extracts, blood, plasma, serum, spinal fluid, lymph fluid, the external sections of the skin, respiratory, intestinal, and genitourinary tracts, tears, saliva, milk, tumors, organs, cell cultures and/or cell culture constituents, for example. A "cancerous sample" is a sample that contains a cancerous cell. The method can be used to examine an aspect of expression of FOLR1 or a state of a sample, including, but not limited to, comparing different types of cells or tissues, comparing different developmental stages, and detecting or determining the presence and/or type of disease or abnormality.

For the purposes herein, a "section" of a tissue sample regards a single part or piece of a tissue sample, e.g. a thin slice of tissue or cells cut from a tissue sample. It is understood that multiple sections of tissue samples may be taken and subjected to analysis according to the present invention. In some cases, the selected portion or section of tissue comprises a homogeneous population of cells. In other cases, the selected portion comprises a region of tissue, e.g. the lumen as a non-limiting example. The selected portion can be as small as one cell or two cells, or could represent many thousands of cells, for example. In most cases, the collection of cells is important, and while the invention has been described for use in the detection of cellular components, the method may also be used for detecting non-cellular components of an organism (e.g. soluble components in the blood as a non-limiting example).

As used herein, the term "capture reagent" refers to a reagent capable of binding and capturing a target molecule in a sample such that under suitable condition, the capture reagent-target molecule complex can be separated from the rest of the sample. In one embodiment, the capture reagent is immobilized. In one embodiment, the capture reagent in a sandwich immunoassay is an antibody or a mixture of different antibodies against a target antigen.

As used herein, the term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. In one embodiment, the detectable antibody is a biotinylated antibody.

As used herein, the term "detection means" refers to a moiety or technique used to detect the presence of the detectable antibody and includes detection agents that amplify the immobilized label such as label captured onto a microtiter plate. In one embodiment, the detection means is a fluorimetric detection agent such as avidin or streptavidin.

Commonly a "sandwich ELISA" employs the following steps: (1) microtiter plate is coated with a capture antibody; (2) sample is added, and any antigen present binds to capture antibody; (3) detecting antibody is added and binds to antigen; (4) enzyme-linked secondary antibody is added and binds to detecting antibody; and (5) substrate is added and is converted by enzyme to detectable form.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. In one embodiment, increased expression of FOLR1 correlates with increased likelihood of effectiveness of a FOLR1-targeting anti-cancer therapy.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include cancers of endothelial, mesenchymal, or epithelial origin, such as lung cancer (e.g., squamous cell cancer, small-cell lung cancer, non-small cell lung cancer, adenocarcinoma of the lung, mesothelioma, and squamous carcinoma of the lung), cancer of the peritoneum (e.g., primary peritoneal), hepatocellular cancer, gastrointestinal cancer, pancreatic cancer, glioblastoma, cervical cancer, ovarian cancer (serous or endometrioid), liver cancer, bladder cancer, hepatoma, breast cancer, colon cancer, colorectal cancer, endometrioid (e.g., endometrial adenocarcinoma) or uterine carcinoma, salivary gland carcinoma, kidney cancer, liver cancer, prostate cancer, vulval cancer, thyroid cancer, hepatic carcinoma, brain cancer (e.g. glioblastoma, tumors of the choroid plexus) and various types of head and neck cancers, and also tumors of blood vessels and fallopian tubes. Cancers also encompass cancers which contain cells having elevated FOLR1 expression levels. Such FOLR1-elevated cancers include, but are not limited to, ovarian, non-small cell lung cancer (adenocarcinoma), uterine, endometrial, pancreatic, renal, lung, and breast cancer.

"Tumor" and "neoplasm" refer to any mass of tissue that result from excessive cell growth or proliferation, either benign (noncancerous) or malignant (cancerous) including pre-cancerous lesions.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical formulation" refers to a preparation which is in such form as to permit the biological activity of the active ingredient to be effective, and which contains no additional components which are unacceptably toxic to a subject to which the formulation would be administered. Such formulation can be sterile.

An "effective amount" of an antibody or immunoconjugate as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), a decrease in CA125 in the case of ovarian cancer, or any combination thereof. See the definition herein of "treating." To the extent the drug can prevent growth and/or kill existing cancer cells, it can be cytostatic and/or cytotoxic. In certain embodiments, identification of increased FOLR1 levels allows for administration of decreased amounts of the FOLR1-targeting therapeutic to achieve the same therapeutic effect as seen with higher dosages. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "respond favorably" generally refers to causing a beneficial state in a subject. With respect to cancer treatment, the term refers to providing a therapeutic effect on the subject. Positive therapeutic effects in cancer can be measured in a number of ways (See, W. A. Weber, J. Nucl. Med. 50:1S-10S (2009)). For example, tumor growth inhibition, molecular marker expression, serum marker expression, and molecular imaging techniques can all be used to assess therapeutic efficacy of an anti-cancer therapeutic. With respect to tumor growth inhibition, according to NCI standards, a T/C≤42% is the minimum level of anti-tumor activity. A T/C <10% is considered a high anti-tumor activity level, with T/C (%)=Median tumor volume of the treated/Median tumor volume of the control×100. A favorable response can be assessed, for example, by increased progression-free survival (PFS), disease-free survival (DFS), or overall survival (OS), complete response (CR), partial response (PR), or, in some cases, stable disease (SD), a decrease in progressive disease (PD), a reduced time to progression (TTP), a decrease in CA125 in the case of ovarian cancer or any combination thereof.

PFS, DFS, and OS can be measured by standards set by the National Cancer Institute and the U.S. Food and Drug Administration for the approval of new drugs. See Johnson et al, (2003) J. Clin. Oncol. 21(7):1404-1411.

"Progression free survival" (PFS) refers to the time from enrollment to disease progression or death. PFS is generally measured using the Kaplan-Meier method and Response Evaluation Criteria in Solid Tumors (RECIST) 1.1 standards. Generally, progression free survival refers to the situation wherein a patient remains alive, without the cancer getting worse.

"Time to Tumor Progression" (TTP) is defined as the time from enrollment to disease progression. TTP is generally measured using the RECIST 1.1 criteria.

A "complete response" or "complete remission" or "CR" indicates the disappearance of all signs of tumor or cancer in response to treatment. This does not always mean the cancer has been cured.

A "partial response" or "PR" refers to a decrease in the size or volume of one or more tumors or lesions, or in the extent of cancer in the body, in response to treatment.

"Stable disease" refers to disease without progression or relapse. In stable disease there is neither sufficient tumor shrinkage to qualify for partial response nor sufficient tumor increase to qualify as progressive disease.

"Progressive disease" refers to the appearance of one more new lesions or tumors and/or the unequivocal progression of existing non-target lesions. Progressive disease can also refer to a tumor growth of more than 20 percent since treatment began, either due to an increases in mass or in spread of the tumor.

"Disease free survival" (DFS) refers to the length of time during and after treatment that the patient remains free of disease.

"Overall Survival" (OS) refers to the time from patient enrollment to death or censored at the date last known alive. OS includes a prolongation in life expectancy as compared to naive or untreated individuals or patients. Overall survival refers to the situation wherein a patient remains alive for a defined period of time, such as one year, five years, etc., e.g., from the time of diagnosis or treatment.

A "decrease in CA125 levels" can be assessed according to the Gynecologic Cancer Intergroup (GCIG) guidelines. For example, CA125 levels can be measured prior to treatment to establish a baseline CA125 level. CA125 levels can be measured one or more times during or after treatment, and a reduction in the CA125 levels over time as compared to the baseline level is considered a decrease in CA125 levels.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), a decrease in CA125 in the case of ovarian cancer, or any combination thereof.

Prophylactic or preventative measures refer to therapeutic measures that prevent and/or slow the development of a targeted pathologic condition or disorder. Thus, those in need of prophylactic or preventative measures include those prone to have the disorder and those in whom the disorder is to be prevented.

As used herein, the term "healthcare provider" refers to individuals or institutions which directly interact with and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy to treat a cancer. "Administration" of a therapy, as used herein, includes prescribing a therapy to a subject as well as delivering, applying, or giving the therapy to a subject. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy or therapeutic agent (e.g., a FOLR1 binding agent), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent. These actions can be performed by a healthcare provider automatically using a computer-implemented method (e.g., via a web service or stand-alone computer system).

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains. In some embodiments, a polypeptide, peptide, or protein is non-naturally occurring. In some embodiments, a polypeptide, peptide, or protein is purified from other naturally occurring components. In some embodiments, the polypeptide, peptide, or protein is recombinantly produced.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.,*

87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value therebetween, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the FOLR1 to which the polypeptide or antibody binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. FOLR1-Binding Agents

The present invention provides agents that specifically bind human FOLR1. These agents are referred to herein as "FOLR1-binding agents." In certain embodiments, the FOLR1 binding agents are antibodies, immunoconjugates or polypeptides. The amino acid and nucleotide sequences for human FOLR1 are known in the art and are also provided herein as represented by SEQ ID NO:1 and SEQ ID NO:2.

Human Folate Receptor 1:
(SEQ ID NO: 1)
MAQRMTTQLLLLLVWVAVVGEAQTRIAWARTELLNVCMNAKHHKEKPG

PEDKLHEQCRPWRKNACCSTNTSQEAHKDVSYLYRFNWNHCGEMAPAC

-continued
KRHFIQDTCLYECSPNLGPWIQQVDQSWRKERVLNVPLCKEDCEQWWE

DCRTSYTCKSNWHKGWNWTSGFNKCAVGAACQPFHFYFPTPTVLCNEI

WTHSYKVSNYSRGSGRCIQMWFDPAQGNPNEEVARFYAAAMSGAGPWA

AWPFLLSLALMLLWLLS

Human Folate Receptor 1 Nucleic Acid Sequence:
(SEQ ID NO: 2)
atggctcagcggatgacaacacagctgctgctcctctagtgtgggtg gctgtagtaggggaggctcagacaaggattgcatgggccaggactgag cttctcaatgtctgcatgaacgccaagcaccacaaggaaaagccaggc cccgaggacaagttgcatgagcagtgtcgaccctggaggaagaatgcc tgctgttctaccaacaccagccaggaagcccataaggatgtttcctac ctatatagattcaactggaaccactgtggagagatggcacctgcctgc aaacggcatttcatccaggacacctgcctctacgagtgctcccccaac ttggggccctggatccagcaggtggatcagagctggcgcaaagagcgg gtactgaacgtgcccctgtgcaaagaggactgtgagcaatggtgggaa gattgtcgcacctcctacacctgcaagagcaactggcacaagggctgg aactggacttcagggtttaacaagtgcgcagtgggagctgcctgccaa cctttccatttctacttccccacacccactgttctgtgcaatgaaatc tggactcactcctacaaggtcagcaactacagccagggagtggccgc tgcatccagatgtggttcgacccagcccagggcaacccaatgaggag gtggcgaggttctatgctgcagccatgagtggggctgggcctgggca gcctggcctttcctgcttagcctggccctaatgctgctgtggctgctc agc Thus, in some embodiments, the FOLR1 binding agents can bind to an epitope of SEQ ID NO:1.

In some embodiments, an anti-FOLR1 antibody can specifically binds to an epitope of FOLR1 (SEQ ID NO:1), wherein epitope comprises an N-glycosylated amino acid. Such antibodies will therefore bind to FOLR1 when it is glycosylated and will not bind to FOLR1 when it is not glycosylated. In other words, the binding of these antibodies is glycol-dependent. These antibodies are advantageous in that they can be used to distinguish between glycosylated and non-glycosylated forms of FOLR1. Given that glycosylation can be required for membrane localization, the antibodies can advantageously be used for membrane specific staining.

In some embodiments, the anti-FOLR1 antibody can specifically bind to an epitope of FOLR1 comprising N-glycosylated amino acid 69 of FOLR1. In some embodiments, the anti-FOLR1 antibody can specifically bind to an epitope of FOLR1 comprising N-glycosylated amino acid 161 of FOLR1. In some embodiments, the anti-FOLR1 antibody can specifically bind to an epitope of FOLR1 comprising N-glycosylated amino acid 201 of FOLR1.

In certain embodiments, the anti-FOLR1 antibody is the antibody produced by the hybridoma deposited with the American Type Culture Collection (ATCC), located at 10801 University Boulevard, Manassas, Va. 20110 on Apr. 16, 2013 under the terms of the Budapest Treaty and having ATCC deposit no. PTA-120196 ("FOLR1-9.20," also referred to as "IMGN 353.9-20," "353.9-20," or "9.20"). In certain embodiments, the anti-FOLR1 antibody is the anti-body produced by the hybridoma deposited with the ATCC on Apr. 16, 2013 and having ATCC deposit no. PTA-120197 ("FOLR1-2.1," also referred to as "IMGN 353.2-1," "353.2-1," "2.1," or "muFRIHC2-1").

The FOLR1-binding agents include FOLR1-binding agents that comprise the heavy and light chain CDR sequences of (i) muFRIHC2-1, which is also known as "FOLR1-2.1," "IMGN 353.2-1," "353.2-1," or "2.1", (ii) muFRIHC5-7, which is also known as "IMGN 353.5-7," "353.5-7" or "5.7," (iii) "muFRIHC9-20," which is also known as "FOLR1-9.20," "IMGN 353.9-20," "353.9-20," or "9.20," (iv) resurfaced huFRIHC2-1 version 1.0 or 1.01, or (v) CDR grafted huFRIHC2-1 version 1.0 or 1.01, which are provided in Tables 1 and 2 below. The FOLR1-binding agents also include FOLR1-binding agents that comprise the heavy and light chain CDR sequences of the composite CDRs provided in Tables 1 and 2 below.

TABLE 1

Variable heavy chain CDR amino acid sequences

| Antibody | VH-CDR1 | VH-CDR2 | VH-CDR3 |
|---|---|---|---|
| muFRIHC2-1 ("2.1") | NSYIH (SEQ ID NO: 3) | WIYPESLNT QYNEKFKA (SEQ ID NO: 4) | RGIYYYS PYALDH (SEQ ID NO: 5) |
| muFRIHC5-7 ("5.7") | NYYIH (SEQ ID NO: 9) | WIYPGSFNV EYNEKFKA (SEQ ID NO: 10) | RGIYFYS PYALDY (SEQ ID NO: 11) |
| muFRIHC9-20 ("9.20") | NYYIH (SEQ ID NO: 15) | WIYPENVNV RYNDKFKA (SEQ ID NO: 16) | RGIYYYS PYAMDY (SEQ ID NO: 17) |
| Composite | N(Y/S)YIH (SEQ ID NO: 21) | WIYP(G/E) (S/N)(F/V/L) N(V/T) (E/R/Q)YN (E/D)KFKA (SEQ ID NO: 22) | RGIY(F/Y) YSPYA(L/M) D(Y/H) (SEQ ID NO: 23) |

TABLE 2

Variable light chain CDR amino acid sequences

| Antibody | VL-CDR1 | VL-CDR2 | VL-CDR3 |
|---|---|---|---|
| muFRIHC2-1 ("2.1") | KSSKSLLN SDGFTYLD (SEQ ID NO: 6) | LVSNHFS (SEQ ID NO: 7) | FQSNYLPLT (SEQ ID NO: 8) |
| muFRIHC5-7 ("5.7") | KSTESLLN SDGFTYLD (SEQ ID NO: 12) | LVSNHFS (SEQ ID NO: 13) | FQSNYLPLT (SEQ ID NO: 14) |
| muFRIHC9-20 ("9.20") | KSTKSLLN SDGFTYLD (SEQ ID NO: 18) | LVSNHFS (SEQ ID NO: 19) | FQSNYLPLT (SEQ ID NO: 20) |
| Composite | KS(T/S)(K/E) SLLNSDGFTYLD (SEQ ID NO: 24) | LVSNHFS (SEQ ID NO: 25) | FQSNYLPLT (SEQ ID NO: 26) |

The FOLR1 binding molecules can be antibodies or antigen binding fragments that specifically bind to FOLR1 that comprise the CDRs of antibody 2.1 (i.e., SEQ ID NOs: 3-8), 5.7 (i.e., SEQ ID NOs: 9-14), or 9.20 (i.e., SEQ ID NOs: 15-20), with up to four (i.e., 0, 1, 2, 3, or 4) conservative amino acid substitutions per CDR. The FOLR1 binding molecules can be antibodies or antigen-binding fragments that specifically bind to FOLR1 that comprise the CDRs of the composite sequence shown above (i.e., SEQ ID NOs: 21-26), with up to four (i.e., 0, 1, 2, 3, or 4) conservative amino acid substitutions per CDR.

The FOLR1 binding molecules can be antibodies or antigen-binding fragments that specifically bind to FOLR1 that comprise the CDRs of antibody produced by the hybridoma of ATCC deposit no. PTA-120196 or PTA-120197.

Polypeptides can comprise one of the individual variable light chains or variable heavy chains described herein. Antibodies and polypeptides can also comprise both a variable light chain and a variable heavy chain. The variable light chain and variable heavy chain sequences of murine antibodies 2.1, 5.7, and 9.20 and humanized 2.1 are provided in Tables 3 and 4 below.

TABLE 3

Variable heavy chain amino acid sequences

| Antibody | VH Amino Acid Sequence (SEQ ID NO) |
|---|---|
| muFRIHC2-1 ("2.1") | QVQLQQSGPELVKPGASVRISCKASGYTFT NSYIHWVKKRPGQGLEWIGWIYPESLNTQY NEKFKAKATLTADKSSSTSYMQLSSLTSED SAVYFCARRGIYYYSPYALDHWGQGASVTV SS (SEQ ID NO: 27) |
| muFRIHC5-7 ("5.7") | QVQLQQSGPEVVKPGASVRISCKASGYTFT NYYIHWVKQRPGQGLEWIGWIYPGSFNVEY NEKFKAKATLTADKSSSTVYMQLSSLTSED SAVYFCARRGIYFYSPYALDYWGQGASVTV SS (SEQ ID NO: 29) |
| muFRIHC9-20 ("9.20") | QVQLQQSGPDLVKPGASVRISCKASGFTFT NYYIHWVKQRPGQGLEWIGWIYPENVNVRY NDKFKAKATLTADKSSSTAYMQLSSLTSED SAVYFCARRGIYYYSPYAMDYWGQGASVTV SS (SEQ ID NO: 31) |
| huFRIHC2-1 (resurfaced) | QVQLVQSGAEVVKPGASVKISCKASGYTFT NSYIHWVKKRPGQGLEWIGWIYPESLNTQY NQKFQGKATLTADKSSSTSYMQLSSLTSED SAVYFCARRGIYYYSPYALDHWGQGASVTV SS (SEQ ID NO: 62) |
| huFRIHC2-1 (grafted) | QVQLVQSGAEVKKPGASVKVSCKASGYTFT NSYIHWVRQAPGQGLEWMGWIYPESLNTQY NEKFKARVTMTRDTSISTAYMELSRLRSDD TAVYYCARRGIYYYSPYALDHWGQGTLVTV SSAST (SEQ ID NO: 65) |

TABLE 4

Variable light chain amino acid sequences

| Antibody | VL Amino Acid Sequence (SEQ ID NO) |
|---|---|
| muFRIHC2-1 ("2.1") | SDVVLTQTPLSLPVNIGDQASISCKSSKSL LNSDGFTYLDWYLQKPGQSPQLLIYLVSNH FSGVPDRFSGSGSGTDFTLKISRVEAEDLG VYYCFQSNYLPLTFGGGTKLEIKR (SEQ ID NO: 28) |
| muFRIHC5-7 ("5.7") | SDVVLTQTPLSLPVNIGDQASISCKSTESL LNSDGFTYLDWYLQKPGQSPQLLIYLVSNH FSGVPDRFSGSGSGTDFTLKISRVEAEDLG VYYCFQSNYLPLTFGGGTKLEVKR (SEQ ID NO: 30) |

TABLE 4-continued

Variable light chain amino acid sequences

| Antibody | VL Amino Acid Sequence (SEQ ID NO) |
|---|---|
| muFRIHC9-20 ("9.20") | SDVVLTQTPLSLPVNLGDQASISCKSTKSL LNSDGFTYLDWYLQKPGQSPQLLIYLVSNH FSGVPDRFSGSGSGTDFTLKISRVEAEDLG VYYCFQSNYLPLTFGGGTKLEIKR (SEQ ID NO: 32) |
| huFRIHC2-1 v. 1.0 (resurfaced) | DVVLTQSPLSLPVNLGQPASISCRSSRSLL NSDGFTYLDWYLQKPGQSPRLLIYLVSNHF SGVPDRFSGSGSGTDFTLKISRVEAEDLGV YYCFQSNYLPLTFGQGTKLEIKR (SEQ ID NO: 63) |
| huFRIHC2-1 v. 1.01 (resurfaced) | DVVLTQSPLSLPVNLGQPASISCKSSKSLL NSDGFTYLDWYLQKPGQSPRLLIYLVSNHF SGVPDRFSGSGSGTDFTLKISRVEAEDLGV YYCFQSNYLPLTFGQGTKLEIKR (SEQ ID NO: 64) |
| huFRIHC2-1 v. 1.0 (grafted) | DIVMTQTPLSLSVTPGQPASISCRSSRSLL NSDGFTYLDWYLQKPGQSPQLLIYLVSNHF SGVPDRFSGSGSGTDFTLKISRVEAEDVGV YYCFQSNYLPLTFGQGTKLEIK (SEQ ID NO: 66) |
| huFRIHC2-1 v. 1.01 (grafted) | DIVMTQTPLSLSVTPGQPASISCKSSKSLL NSDGFTYLDWYLQKPGQSPQLLIYLVSNHF SGVPDRFSGSGSGTDFTLKISRVEAEDVGV YYCFQSNYLPLTFGQGTKLEIK (SEQ ID NO: 67) |

Also provided are polypeptides that comprise: (a) a polypeptide having at least about 90% sequence identity to SEQ ID NOs:27, 29, 31, 62, or 65; and/or (b) a polypeptide having at least about 90% sequence identity to SEQ ID NOs:28, 30, 32, 63, 64, 66, or 67. In certain embodiments, the polypeptide comprises a polypeptide having at least about 95%, at least about 96%, at least about 97%, at least about 98%, or at least about 99% sequence identity to SEQ ID NOs:27-32 or 62-67. Thus, in certain embodiments, the polypeptide comprises (a) a polypeptide having at least about 95% sequence identity to SEQ ID NOs:27, 29, 31, 62, or 65 and/or (b) a polypeptide having at least about 95% sequence identity to SEQ ID NOs:28, 30, 32, 63, 64, 66, or 67. In certain embodiments, the polypeptide comprises (a) a polypeptide having the amino acid sequence of SEQ ID NOs:27, 29, 31, 62, or 65; and/or (b) a polypeptide having the amino acid sequence of SEQ ID NOs:28, 30, 32, 63, 64, 66, or 67. In certain embodiments, the polypeptide is an antibody and/or the polypeptide specifically binds FOLR1. In certain embodiments, the polypeptide is a murine, chimeric, or humanized antibody that specifically binds FOLR1. In certain embodiments, the polypeptide having a certain percentage of sequence identity to SEQ ID NOs:27-32 or 62-67 differs from SEQ ID NOs:27-32 or 62-67 by conservative amino acid substitutions only.

Also provided are polypeptides comprising a variable light chain that is at least about 85%, at least about 90%, at least about 95%, or at least about 99%, or is identical to the variable light chain sequence of the antibody produced by the hybridoma having ATCC deposit no. PTA-120196 or PTA-120197.

Also provided are polypeptides comprising a variable heavy chain that is at least about 85%, at least about 90%, at least about 95%, or at least about 99%, or is identical to the variable heavy chain sequence of the antibody produced by the hybridoma having ATCC deposit no. PTA-120196 or PTA-120197.

Also provided are antibodies and antigen-binding fragments thereof comprising variable heavy and variable light chain sequences that are at least about 85%, at least about 90%, at least about 95%, or at least about 99%, or identical to the variable heavy and variable light chain sequences of the antibody produced by the hybridoma having ATCC deposit no. PTA-120196 or PTA-120197.

In certain embodiments, the antibody or antigen-binding fragment is the antibody produced by the hybridoma having ATCC deposit no. PTA-120196 or an antigen-binding fragment thereof.

In certain embodiments, the antibody or antigen-binding fragment is the antibody produced by the hybridoma having ATCC deposit no. PTA-120197 or an antigen-binding fragment thereof.

Polypeptides can comprise one of the individual light chains or heavy chains described herein. Antibodies and polypeptides can also comprise both a light chain and a heavy chain. The light chain and heavy chain sequences of antibodies 2.1, 5.7, and 9.20 are provided in Tables 5 and 6 below.

TABLE 5

Full-length heavy chain amino acid sequences

| Antibody | Full-Length Heavy Chain Amino Acid Sequence (SEQ ID NO) |
| --- | --- |
| muFRIHC2-1 ("2.1") | QVQLQQSGPELVKPGASVRISCKASGYTFT NSYIHWVKKRPGQGLEWIGWIYPESLNTQY NEKFKAKATLTADKSSSTSYMQLSSLTSED SAVYFCARRGIYYYSPYALDHWGQGASVTV SSAKTTPPSVYPLAPGSAAQTNSMVTLGCL VKGYFPEPVTVTWNSGSLSSGVHTFPAVLE SDLYTLSSSVTVPSSMRPSETVTCNVAHPA SSTKVDKKIVPRDCGCKPCICTVPEVSSVF IFPPKPKDVLTITLTPKVTCVVVDISKDDP EVQFSWFVDDVEVHTAQTQPREEQFNSTFR SVSELPIMHQDWLNGKEFKCRVNSAAFPAP IEKTISKTKGRPKAPQVYTIPPPKEQMAKD KVSLTCMITDFFPEDITVEWQWNGQPAENY KNTQPIMNTNGSYFVYSKLNVQKSNWEAGN TFTCSVLHEGLHNHHTEKSLSHSPGK (SEQ ID NO: 33) |
| muFRIHC5-7 ("5.7") | QVQLQQSGPEVVKPGASVRISCKASGYTFT NYYIHWVKQRPGQGLEWIGWIYPGSFNVEY NEKFKAKATLTADKSSSTVYMQLSSLTSED SAVYFCARRGIYFYSPYALDYWGQGASVTV SSAKTTPPSVYPLAPGSAAQTNSMVTLGCL VKGYFPEPVTVTWNSGSLSSGVHTFPAVLE SDLYTLSSSVTVPSSMRPSETVTCNVAHPA SSTKVDKKIVPRDCGCKPCICTVPEVSSVF IFPPKPKDVLTITLTPKVTCVVVDISKDDP EVQFSWFVDDVEVHTAQTQPREEQFNSTFR SVSELPIMHQDWLNGKEFKCRVNSAAFPAP IEKTISKTKGRPKAPQVYTIPPPKEQMAKD KVSLTCMITDFFPEDITVEWQWNGQPAENY KNTQPIMNTNGSYFVYSKLNVQKSNWEAGN TFTCSVLHEGLHNHHTEKSLSHSPGK (SEQ ID NO: 35) |
| muFRIHC9-20 ("9.20") | QVQLQQSGPDLVKPGASVRISCKASGFTFT NYYIHWVKQRPGQGLEWIGWIYPENVNVRY NDKFKAKATLTADKSSSTAYMQLSSLTSED SAVYFCARRGIYYYSPYAMDYWGQGASVTV SSAKTTPPSVYPLAPGSAAQTNSMVTLGCL VKGYFPEPVTVTWNSGSLSSGVHTFPAVLE SDLYTLSSSVTVPSSMRPSETVTCNVAHPA SSTKVDKKIVPRDCGCKPCICTVPEVSSVF IFPPKPKDVLTITLTPKVTCVVVDISKDDP EVQFSWFVDDVEVHTAQTQPREEQFNSTFR SVSELPIMHQDWLNGKEFKCRVNSAAFPAP IEKTISKTKGRPKAPQVYTIPPPKEQMAKD KVSLTCMITDFFPEDITVEWQWNGQPAENY KNTQPIMNTNGSYFVYSKLNVQKSNWEAGN TFTCSVLHEGLHNHHTEKSLSHSPGK (SEQ ID NO: 37) |

TABLE 5-continued

Full-length heavy chain amino acid sequences

| Antibody | Full-Length Heavy Chain Amino Acid Sequence (SEQ ID NO) |
| --- | --- |
| muhuMov19 | QVQLVQSGAEVVKPGASVKISCKASGYTFT GYFMNWVKQSPGQSLEWIGRIHPYDGDTFY NQKFQGKATLTVDKSSNTAHMELLSLTSED FAVYYCTRYDGSRAMDYWGQGTTVTVSSAS TKGPSVYPLAPGSAAQTNSMVTLGCLVKGY FPEPVTVTWNSGSLSSGVHTFPAVLESDLY TLSSSVTVPSSMRPSETVTCNVAHPASSTK VDKKIVPRDCGCKPCICTVPEVSSVFIFPP KPKDVLTITLTPKVTCVVVDISKDDPEVQF SWFVDDVEVHTAQTQPREEQFNSTFRSVSE LPIMHQDWLNGKEFKCRVNSAAFPAPIEKT ISKTKGRPKAPQVYTIPPPKEQMAKDKVSL TCMITDFFPEDITVEWQWNGQPAENYKNTQ PIMNTNGSYFVYSKLNVQKSNWEAGNTFTC SVLHEGLHNHHTEKSLSHSPGK (SEQ ID NO:68) |

TABLE 6

Full-length light chain amino acid sequences

| Antibody | Full-length Light Chain Amino Acid Sequence (SEQ ID NO) |
| --- | --- |
| muFRIHC2-1 ("2.1") | SDVVLTQTPLSLPVNIGDQASISCKSSKSL LNSDGFTYLDWYLQKPGQSPQLLIYLVSNH FSGVPDRFSGSGSGTDFTLKISRVEAEDLG VYYCFQSNYLPLTFGGGTKLEIKRADAAPT VSIFPPSSEQLTSGGASVVCFLNNFYPKDI NVKWKIDGSERQNGVLNSWTDQDSKDSTYS MSSTLTLTKDEYERHNSYTCEATHKTSTSP IVKSFNRNEC (SEQ ID NO: 34) |
| muFRIHC5-7 ("5.7") | SDVVLTQTPLSLPVNIGDQASISCKSTESL LNSDGFTYLDWYLQKPGQSPQLLIYLVSNH FSGVPDRFSGSGSGTDFTLKISRVEAEDLG VYYCFQSNYLPLTFGGGTKLEVKRADAAPT VSIFPPSSEQLTSGGASVVCFLNNFYPKDI NVKWKIDGSERQNGVLNSWTDQDSKDSTYS MSSTLTLTKDEYERHNSYTCEATHKTSTSP IVKSFNRNEC (SEQ ID NO: 36) |
| muFRIHC9-20 ("9.20") | SDVVLTQTPLSLPVNLGDQASISCKSTKSL LNSDGFTYLDWYLQKPGQSPQLLIYLVSNH FSGVPDRFSGSGSGTDFTLKISRVEAEDLG VYYCFQSNYLPLTFGGGTKLEIKRADAAPT VSIFPPSSEQLTSGGASVVCFLNNFYPKDI NVKWKIDGSERQNGVLNSWTDQDSKDSTYS MSSTLTLTKDEYERHNSYTCEATHKTSTSP IVKSFNRNEC (SEQ ID NO: 38) |
| muhuMov19 | DIVLTQSPLSLAVSLGQPAIISCKASQSVS FAGTSLMHWYHQKPGQQPRLLIYRASNLEA GVPDRFSGSGSKTDFTLTISPVEAEDAATY YCQQSREYPYTFGGGTKLEIKRTDAAPTVS IFPPSSEQLTSGGASVVCFLNNFYPKDINV KWKIDGSERQNGVLNSWTDQDSKDSTYSMS STLTLTKDEYERHNSYTCEATHKTSTSPIV KSFNRNEC (SEQ ID NO: 69) |

Also provided are polypeptides that comprise: (a) a polypeptide having at least about 90% sequence identity to SEQ ID NOs:33, 35, or 37; and/or (b) a polypeptide having at least about 90% sequence identity to SEQ ID NOs:34, 36, or 38. In certain embodiments, the polypeptide comprises a polypeptide having at least about 95%, at least about 96%, at least about 97%, at least about 98%, or at least about 99% sequence identity to SEQ ID NOs:33-38. Thus, in certain embodiments, the polypeptide comprises (a) a polypeptide having at least about 95% sequence identity to SEQ ID NOs:33, 35, or 37, and/or (b) a polypeptide having at least about 95% sequence identity to SEQ ID NOs:34, 36, or 38. In certain embodiments, the polypeptide comprises (a) a polypeptide having the amino acid sequence of SEQ ID NOs:33, 35, or 37; and/or (b) a polypeptide having the amino acid sequence of SEQ ID NOs:34, 36, or 38. In certain embodiments, the polypeptide is an antibody and/or the polypeptide specifically binds FOLR1. In certain embodiments, the polypeptide is a murine, chimeric, or humanized antibody that specifically binds FOLR1. In certain embodiments, the polypeptide having a certain percentage of sequence identity to SEQ ID NOs:33-38 differs from SEQ ID NOs:33-38 by conservative amino acid substitutions only.

Also provided are polypeptides comprising a light chain that is at least about 85%, at least about 90%, at least about 95%, or at least about 99%, or is identical to the light chain sequence of the antibody produced by the hybridoma having ATCC deposit no. PTA-120196 or PTA-120197.

Also provided are polypeptides comprising a heavy chain that is at least about 85%, at least about 90%, at least about 95%, or at least about 99%, or is identical to the heavy chain sequence of the antibody produced by the hybridoma having ATCC deposit no. PTA-120196 or PTA-120197.

Also provided are antibodies and antigen-binding fragments thereof comprising heavy and light chain sequences that are at least about 85%, at least about 90%, at least about 95%, or at least about 99%, or identical to the heavy and light chain sequences of the antibody produced by the hybridoma having ATCC deposit no. PTA-120196 or PTA-120197.

The affinity or avidity of an antibody for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, $K_{on}$, $K_{off}$) are made with standardized solutions of antibody and antigen, and a standardized buffer, as known in the art and such as the buffer described herein.

In one aspect, binding assays can be performed using flow cytometry on cells expressing the FOLR1 antigen on the surface. For example, FOLR1-positive cells such as SKOV3 can be incubated with varying concentrations of anti-FOLR1 antibodies using $1\times10^5$ cells per sample in 100 µL FACS buffer (RPMI-1640 medium supplemented with 2% normal goat serum). Then, the cells can be pelleted, washed, and incubated for 1 h with 100 µL of FITC-conjugated goat-anti-mouse or goat-anti-human IgG-antibody (such as is obtainable from, for example Jackson Laboratory, 6 µg/mL in FACS buffer). The cells are then pelleted again, washed with FACS buffer and resuspended in 200 µL of PBS containing 1% formaldehyde. Samples can be acquired, for example, using a FACSCalibur flow cytometer with the HTS multiwell sampler and analyzed using CellQuest Pro (all from BD Biosciences, San Diego, US). For each sample the mean fluorescence intensity for FL1 (MFI) can be exported and plotted against the antibody concentration in a semi-log plot to generate a binding curve. A sigmoidal dose-response curve is fitted for binding curves and EC50 values are calculated using programs such as GraphPad Prism v4 with default parameters (GraphPad software, San Diego, Calif.). EC50 values can be used as a measure for the apparent dissociation constant "Kd" or "KD" for each antibody.

Monoclonal antibodies can be prepared using hybridoma methods, such as those described by Kohler and Milstein (1975) Nature 256:495. Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human FOLR1 is a humanized antibody. In certain embodiments, such antibodies are used therapeutically to reduce antigenicity and HAMA (human anti-mouse antibody) responses when administered to a human subject.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing FOLR1 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen FOLR1 and other favorable biological properties. To achieve this goal, humanized (or human) or engineered anti-FOLR1 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as FOLR1. In this way, framework (FR) residues can be selected and combined from the consensus and import sequences so that the desired antibody characteristic, such as increased affinity for the target antigen(s), is achieved.

Humanization, resurfacing or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and U.S. Pat. No. 7,342,110, each of which is entirely incorporated herein by reference, including the references cited therein.

In certain alternative embodiments, the antibody to FOLR1 is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from E. coli or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

For the purposes of the present invention, it should be appreciated that modified antibodies can comprise any type of variable region that provides for the association of the antibody with the polypeptides of a human FOLR1. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g., cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human FOLR1. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human FOLR1. Recombinant expression vectors are replicable DNA constructs which have synthetic or cDNA-derived DNA fragments encoding a polypeptide chain of an anti-FOLR1 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a FOLR1-binding polypeptide or antibody (or a FOLR1 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultra-filtration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a FOLR1-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

III. Polynucleotides

In certain embodiments, the invention encompasses polynucleotides comprising polynucleotides that encode a polypeptide that specifically binds a human FOLR1 receptor or a fragment of such a polypeptide. For example, the invention provides a polynucleotide comprising a nucleic acid sequence that encodes an antibody to a human FOLR1 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is a cDNA or a DNA lacking one more endogenous introns.

In some embodiments, a polynucleotide is a non-naturally occurring polynucleotide. In some embodiments, a polynucleotide is recombinantly produced.

In certain embodiments, the polynucleotides are isolated. In certain embodiments, the polynucleotides are substantially pure. In some embodiments, a polynucleotide is purified from natural components.

The invention provides a polynucleotide comprising a polynucleotide encoding a polypeptide comprising a sequence selected from the group consisting of SEQ ID NOs:3-38 and 59-67. Also provided is a polynucleotide encoding a polypeptide having at least about 95%, at least about 96%, at least about 97%, at least about 98%, or at least about 99% sequence identity to SEQ ID NOs:3-38 and 59-67.

The invention further provides a polynucleotide comprising a sequence selected from those shown in Tables 7 and 8 below.

TABLE 7

Variable heavy chain polynucleotide sequences

| Antibody | Variable Heavy Chain Polynucleotide Sequence (SEQ ID NO) |
|---|---|
| muFRIHC2-1 ("2.1") | caggtccaactgcagcagtctggacctgagctggt gaagcctggggcttcagtgaggatatcctgcaagg cttctggctacaccttcacaaactcctatattcac tgggtgaaaaagaggcctggacagggacttgagtg gattggatggatttatcctgaaagtcttaatactc aatacaatgagaagttcaaggccaaggccacactg actgctgacaagtcctccagcacatcctacatgca gctcagcagtctgacctctgaggactctgcggtct atttctgtgcaagaaggggtatttattactactct ccctatgctctggaccactggggtcaaggagcctc agtcaccgtctcctca (SEQ ID NO: 39) |
| muFRIHC5-7 ("5.7") | caggtccaactgcagcagtctggacctgaggtggt gaagcctggggcttcagtgaggatatcctgcaagg cttctggctacaccttcacaaactactatatacac tgggtgaagcagaggcctggacagggacttgagtg gattggatggatttatcctggaagttttaatgttg agtacaatgagaagttcaaggccaaggccacactg actgcagacaaatcctccagcacagtctacatgca actcagcagcctgacctctgaggactctgcggtct atttctgtgcaagaaggggtatttatttctactct ccctatgctttggactactggggtcaaggagcctc agtcaccgtctcctca (SEQ ID NO: 41) |
| muFRIHC9-20 ("9.20") | caggtccaactgcagcagtctggacctgacctggt gaagcctggggcttcagtgaggatatcctgcaagg cttctggcttcaccttcacaaactactatatacac tgggtgaagcagaggcctggacagggacttgagtg gattggatggatttatcctgaaaatgttaatgtta ggtacaatgacaagttcaaggccaaggccacactg actgcagacaaatcctccagcacagcctacatgca gctcagcagcctgacctctgaggactctgcggtct atttctgtgcaagaaggggtatttattactactct ccctatgctatggactactggggtcaaggagcctc agtcaccgtctcctca (SEQ ID NO: 43) |
| huFRIHC2-1 (resurfaced) | aagcttgccaccATGGGTTGGAGCTGCATTATCCT TTTCCTTGTGGCTACAGCTACTGGCGTTCACTCTC AGGTACAATTGGTTCAGTCAGGAGCCGAGGTCGTA AAGCCCGGTGCCAGTGTGAAGATCTCATGCAAGGC AAGCGGTTATACTTTTACAAACTCTTACATTCATT GGGTGAAAAAGCGGCCCGGCCAGGGTCTCGAATGG ATCGGCTGGATCTACCCAGAAAGTCTGAACACTCA ATACAACCAGAAGTTTCAGGGTAAGGCAACTCTCA CTGCCGACAAGAGCTCTAGCACAAGCTATATGCAG TTGTCTAGTTTGACAAGCGAGGATAGCGCAGTTTA CTTTTGTGCTCGGCGTGGTATTTATTACTACTCAC CTTATGCTCTGGATCACTGGGGACAGGGTGCCTCT GTTACCGTTTCCAGTGCATCCACCaagggccc (SEQ ID NO: 70) |
| huFRIHC2-1 (grafted) | aagcttgccaccATGGGCTGGAGCTGCATAATCCT CTTCCTCGTAGCTACCGCCACTGGGGTGCATTCTC AAGTACAGTTGGTGCAGTCCGGAGCTGAAGTCAAG AAGCCAGGGGCTTCTGTTAAGGTGAGCTGTAAGGC TTCCGGATATACCTTCACAAACAGTTATATCCATT GGGTGAGGCAAGCTCCAGGCCAGGGTCTCGAATGG ATGGGATGGATCTACCCCGAGAGTCTGAACACCCA GTACAACGAGAAGTTCAAGGCACGTGTGACCATGA CAAGAGACACCTCCATCAGTACAGCCTATATGGAA TTGAGCCGTCTCAGAAGTGATGATACAGCAGTGTA CTACTGCGCCAGGCGGGGCATCTACTACTACAGCC CATACGCTCTCGACCACTGGGGACAAGGAACACTG GTAACCGTAAGCTCAGCTTCTACAaagggccc (SEQ ID NO: 71) |

TABLE 8

Variable light chain polynucleotide sequences

| Antibody | Variable Light Chain Polynucleotide Sequence (SEQ ID NO) |
|---|---|
| muFRIHC2-1 ("2.1") | agtgatgttgttctgacccaaactccactctctct gcctgtcaatattggagatcaagcctctatctctt gcaagtcttctaagagtcttctgaatagtgatgga ttcacttatttggactggtacctgcagaagccagg ccagtctccacagctcctaatatatttggtttcta atcatttttctggagttccagacaggttcagtggc agtgggtcaggaacagatttcacactcaagatcag cagagtggaggctgaggatttgggagtttattatt gcttccagagtaactatcttcctctcacgttcgga gggggaccaagctggaaataaaacgg (SEQ ID NO: 40) |
| muFRIHC5-7 ("5.7") | agtgatgttgttctgacccaaactccactctctct gcctgtcaatattggagatcaagcctctatctctt gcaagtctactgagagtcttctgaatagtgatgga ttcacttatttggactggtacctgcagaagccagg ccagtctccacagctcctaatatatttggtttcta atcatttttctggagttccagacaggttcagtggc agtgggtcaggaacagatttcacactcaagatcag cagagtggaggctgaggatttgggagtttattatt gcttccagagtaactatcttcctctcacgttcgga gggggaccaagctggaagtaaaacgg (SEQ ID NO: 42) |
| muFRIHC9-20 ("9.20") | agtgatgttgttctgacccaaactccactctctct gcctgtcaatcttggagatcaagcctctatctctt gcaagtctactaagagtcttctgaatagtgatgga ttcacttatttggactggtacctgcagaagccagg ccagtctccacagctcctaatatatttggtttcta atcatttttctggagttccagacaggttcagtggc agtgggtcaggaacagatttcaccctcaagatcag cagagtggaggctgaggatttgggagtttattatt gcttccagagtaactatcttcctctcacgttcgga gggggaccaagctggaaataaaacgg (SEQ ID NO: 44) |
| huFRIHC2-1 v. 1.0 (resurfaced) | gaattcgccaccATGGGTTGGTCATGTATAATACT TTTCCTGGTAGCTACTGCTACTGGTGTGCATTCAG ATGTGGTGCTGACTCAGTCACCCTTGTCTCTCCCA GTCAATCTTGGGCAGCCAGCATCTATCAGCTGCCG AAGCAGCAGGTCTCTCCTGAACTCCGATGGCTTTA CTTATCTTGACTGGTATCTCCAGAAGCCAGGACAG TCCCCCCGGCTGCTCATCTACCTGGTTTCTAATCA TTTTAGTGGCGTCCCTGACCGCTTCTCTGGGAGTG GAAGTGGGACCGATTTTACACTGAAGATCTCCAGG GTCGAAGCTGAGGACCTTGGGGTTTACTACTGTTT CCAGAGCAACTACCTTCCCTTGACATTCGGCCAGG GAACCAAGCTGGAAATCAAGcgtacg (SEQ ID NO: 72) |
| huFRIHC2-1 v. 1.01 (resurfaced) | gaattcgccaccATGGGTTGGTCTTGTATCATTCT GTTCCTGGTCGCCACTGCCACAGGAGTTCACTCAG ACGTGGTACTCACACAATCTCCCCTTTCCCTGCCT GTGAACCTGGGACAGCCAGCCTCAATCAGTTGCAA GAGCTCTAAATCTCTGCTCAATAGCGATGGCTTTA CCTACTTGGATTGGTACCTCCAGAAGCCCGGCCAG TCTCCTCGGCTCCTGATTTACCTTGTTTCAAATCA CTTTTCAGGCGTGCCTGACCGGTTCTCCGGATCTG GCTCAGGGACAGACTTCACCCTGAAGATCTCCCGC GTCGAGGCAGAGGATCTCGGCGTGTATTACTGTTT CCAAAGTAACTACCTGCCATTGACTTTTGGACAAG GAACTAAACTGGAAATCAAAcgtacg (SEQ ID NO: 73) |
| huFRIHC2-1 v. 1.0 (grafted) | gaattcgccaccATGGGATGGAGTTGTATTATTCT GTTCTTGGTCGCTACTGCAACAGGCGTTCATTCTG ACATCGTAATGACCCAGACACCTCTGAGTCTGAGT GTCACTCCCGGCCAGCCCGCCTCTATTTCATGTCG TAGCTCTCGCTCCCTGCTCAATTCCGACGGTTTTA CCTACTTGGACTGGTATCTTCAGAAACCTGGGCAG AGCCCTCAGCTTCTGATCTATCTGGTGTCCAATCA CTTCAGTGGCGTCCCAGACCGATTTTCCGGAAGCG GAAGCGGAACCGACTTTACCCTGAAGATATCCCGC GTCGAAGCAGAGGACGTGGGCGTGTATTATTGCTT |

TABLE 8-continued

Variable light chain polynucleotide sequences

| Antibody | Variable Light Chain Polynucleotide Sequence (SEQ ID NO) |
|---|---|
| | TCAAAGCAATTACTTGCCATTGACTTTCGGACAAG GCACAAAACTGGAGATTAAGcgtacg (SEQ ID NO: 74) |
| huFRIHC2-1 v. 1.01 (grafted) | gaattcgccaccATGGGCTGGTCATGCATCATACT GTTCCTGGTGGCTACAGCAACCGGGGTGCACAGCG ATATTGTTATGACACAGACACCACTGAGTTTGTCA GTGACCCCCGGCCAGCCAGCCTCTATATCCTGCAA GTCCTCAAAAAGTCTCCTGAATAGCGATGGCTTTA CCTACCTCGACTGGTATCTTCAGAAGCCCGGTCAA AGCCCTCAGCTGCTGATATATCTGGTGTCTAACCA TTTTAGCGGAGTCCCCGACCGCTTTTCAGGCTCCG GCAGTGGCACCGACTTCACCCTTAAGATTTCTCGC GTGGAGGCTGAAGATGTAGGGGTCTACTACTGTTT CCAGTCAAACTACCTGCCACTGACCTTTGGTCAAG GCACTAAGCTCGAAATTAAGcgtacg (SEQ ID NO: 75) |

Also provided is a polynucleotide having at least about 95%, at least about 96%, at least about 97%, at least about 98%, or at least about 99% sequence identity to any one of SEQ ID NOs:39-44.

Also provided are polynucleotides encoding a variable light chain that is at least about 85%, at least about 90%, at least about 95%, or at least about 99%, or is identical to the variable light chain sequence of the antibody produced by the hybridoma having ATCC deposit no. PTA-120196 or PTA-120197.

Also provided are polynucleotides comprising a variable light chain-encoding sequence that is at least about 85%, at least about 90%, at least about 95%, or at least about 99%, or is identical to the variable light chain-encoding sequence that encodes the variable light chain of the antibody produced by the hybridoma having ATCC deposit no. PTA-120196 or PTA-120197.

Also provided are polynucleotides encoding a variable heavy chain that is at least about 85%, at least about 90%, at least about 95%, or at least about 99%, or is identical to the variable heavy chain sequence of the antibody produced by the hybridoma having ATCC deposit no. PTA-120196 or PTA-120197.

Also provided are polynucleotides comprising a variable heavy chain-encoding sequence that is at least about 85%, at least about 90%, at least about 95%, or at least about 99%, or is identical to the variable heavy chain-encoding sequence that encodes the variable heavy chain of the antibody produced by the hybridoma having ATCC deposit no. PTA-120196 or PTA-120197.

In certain embodiments the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

Vectors and cells comprising the polynucleotides described herein are also provided.

IV. Biological Samples

Biological samples are often fixed with a fixative. Aldehyde fixatives such as formalin (formaldehyde) and glutaraldehyde are typically used. Tissue samples fixed using other fixation techniques such as alcohol immersion (Battifora and Kopinski, J. Histochem. Cytochem. (1986) 34:1095) are also suitable. The samples used may also be embedded in paraffin. In one embodiment, the samples are both formalin-fixed and paraffin-embedded (FFPE). In another embodiment, the FFPE block is hematoxylin and eosin stained prior to selecting one or more portions for analysis in order to select specific area(s) for the FFPE core sample. Methods of preparing tissue blocks from these particulate specimens have been used in previous IHC studies of various prognostic factors, and/or is well known to those of skill in the art (see, for example, Abbondanzo et al., Am J Clin Pathol. 1990 May; 93(5):698-702; Allred et al., Arch Surg. 1990 January; 125(1):107-13).

Briefly, any intact organ or tissue may be cut into fairly small pieces and incubated in various fixatives (e.g. formalin, alcohol, etc.) for varying periods of time until the tissue is "fixed". The samples may be virtually any intact tissue surgically removed from the body. The samples may be cut into reasonably small piece(s) that fit on the equipment routinely used in histopathology laboratories. The size of the cut pieces typically ranges from a few millimeters to a few centimeters. The biological sample can also be fluidic extracts, blood, plasma, serum, spinal fluid, lymph fluid, and or splenic preparations.

V. Correlation of FOLR1 Expression and Therapeutic Efficacy

The antibody maytansinoid conjugate (AMC) IMGN853 comprises the FOLR1-binding monoclonal antibody, huMov19 (M9346A), conjugated to the maytansinoid, DM4 (N(2)-deacetyl-N2'-(4-mercapto-4-methyl-1-oxopentyl)-maytansine), attached via the cleavable sulfo-SPDB (N-succinimidyl 4-(2-pyridyldithio)-2-sulfobutanoate) linker. The antibody sequences of IMGN853 (huMov19) are provided below as SEQ ID NOs: 45 and 47, and IMGN853 and huMov19 are described in US Appl. Pub. No. 2012/0009181 (now U.S. Pat. No. 8,557,966), which is herein incorporated by reference in its entirety.

```
huMov19 vHC
                                          SEQ ID NO: 45
QVQLVQSGAEVVKPGASVKISCKASGYTFTGYFMNWVKQSPGQSLE

WIGRIHPYDGDTFYNQKFQGKATLTVDKSSNTAHMELLSLTSEDFA

VYYCTRYDGSRAMDYWGQGTTVTVSS huMov19 vLCv1.00
                                          SEQ ID NO: 46
DIVLTQSPLSLAVSLGQPAIISCKASQSVSFAGTSLMHWYHQKPGQ

QPRLLIYRASNLEAGVPDRFSGSGSKTDFTLNISPVEAEDAATYYC

QQSREYPYTFGGGTKLEIKR huMov19 vLCv1.60
                                          SEQ ID NO: 47
DIVLTQSPLSLAVSLGQPAIISCKASQSVSFAGTSLMHWYHQKPGQ

QPRLLIYRASNLEAGVPDRFSGSGSKTDFTLTISPVEAEDAATYYC

QQSREYPYTFGGGTKLEIKR huMov19 vLC CDR1
                                          SEQ ID NO: 48
KASQSVSFAGTSLMH huMov19 vLC CDR2
                                          SEQ ID NO: 49
RASNLEA huMov19 vLC CDR3
                                          SEQ ID NO: 50
QQSREYPYT huMov19 vHC CDR1
                                          SEQ ID NO: 51
GYFMN huMov19 vHC CDR2-Kabat Defined
                                          SEQ ID NO: 52
RIHPYDGDTFYNQKFQG huMov19 vHC CDR2-Abm Defined
                                          SEQ ID NO: 53
RIHPYDGDTF huMov19 vHC CDR3
                                          SEQ ID NO: 54
YDGSRAMDY huMov19 HC amino acid sequence
                                          SEQ ID NO: 55
QVQLVQSGAEVVKPGASVKISCKASGYTFTGYFMNWVKQSPGQSLE

WIGRIHPYDGDTFYNQKFQGKATLTVDKSSNTAHMELLSLTSEDFA

VYYCTRYDGSRAMDYWGQGTTVTVSSASTKGPSVFPLAPSSKSTSG

GTAALGCLVKDYFPEPVTVSWNSGALTSGVHTFPAVLQSSGLYSLS

SVVTVPSSSLGTQTYICNVNHKPSNTKVDKKVEPKSCDKTHTCPPC

PAPELLGGPSVFLFPPKPKDTLMISRTPEVTCVVVDVSHEDPEVKF

NWYVDGVEVHNAKTKPREEQYNSTYRVVSVLTVLHQDWLNGKEYKC

KVSNKALPAPIEKTISKAKGQPREPQVYTLPPSRDELTKNQVSLTC

LVKGFYPSDIAVEWESNGQPENNYKTTPPVLDSDGSFFLYSKLTVD

KSRWQQGNVFSCSVMHEALHNHYTQKSLSLSPGK
```

-continued huMov19 LCv1.00

SEQ ID NO: 56

DIVLTQSPLSLAVSLGQPAIISCKASQSVSFAGTSLMHWYHQKPGQ

QPRLLIYRASNLEAGVPDRFSGSGSKTDFTLNISPVEAEDAATYYC

QQSREYPYTFGGGTKLEIKRTVAAPSVFIFPPSDEQLKSGTASVVC

LLNNFYPREAKVQWKVDNALQSGNSQESVTEQDSKDSTYSLSSTLT

LSKADYEKHKVYACEVTHQGLSSPVTKSFNRGEC huMov19 LCv1.60

SEQ ID NO: 57

DIVLTQSPLSLAVSLGQPAIISCKASQSVSFAGTSLMHWYHQKPGQ

QPRLLIYRASNLEAGVPDRFSGSGSKTDFTLTISPVEAEDAATYYC

QQSREYPYTFGGGTKLEIKRTVAAPSVFIFPPSDEQLKSGTASVVC

LLNNFYPREAKVQWKVDNALQSGNSQESVTEQDSKDSTYSLSSTLT

LSKADYEKHKVYACEVTHQGLSSPVTKSFNRGEC muMov19 vHC CDR2-Kabat Defined

SEQ ID NO: 58

RIHPYDGDTFYNQNFKD

IMGN853 is currently in clinical development for various therapeutic indications which include FOLR1 positive ovarian cancer, non-small cell lung cancer, endometrioid cancer, renal cancer, and other epithelial malignancies. Ovarian cancers exhibit the greatest FOLR1 penetrance and are considered the major indications for treatment with IMGN853 (Antony A C. Ann Rev Nutr 16:501-21 (1996); Yuan Y et al. Hum Pathol 40(10):1453-1460 (2009)). Measuring levels of FOLR1 in patient plasma samples can help identify patient populations more likely to respond to AMC treatment.

In certain embodiments, the invention provides a method for identifying subjects that are likely to respond favorably to FOLR1-targeting anti-cancer therapies due to elevated expression levels of FOLR1 being expressed in the subject, in particular using antibodies and antigen-binding fragments thereof provided herein that can detect a dynamic range of FOLR1 expression levels, e.g., in IHC.

Evaluation of patient samples and correlation to in vivo efficacy using xenograft models demonstrates the power of the expression analysis for selecting subjects more likely to respond to treatment. IHC provides a score for FOLR1 expression on tumor cells: 0 (no expression) to 3 (or 3+) (very high levels of expression). In vivo data using xenograft models demonstrates that samples scoring 2, or 3 (or 3+) for FOLR1 expression have an increased likelihood to respond to FOLR1-targeted anti-cancer therapies at clinically-relevant doses of FOLR1 immuno conjugates (see e.g., U.S. Provisional Application Nos. 61/823,317 and 61/828,586 and International Application No. PCT/US2014/037911, all of which are herein incorporated by reference in their entireties). Thus, identification of individuals having an elevated FOLR1 score would help identify those individuals who might respond to a clinically relevant dosage. Moreover, expression of more uniform levels of FOLR1 provides better correlation with therapeutic benefit. Thus, a homogenous staining uniformity or a combination of increased staining with heterogenous staining uniformity can indicate increased FOLR1 expression. For example, scores of greater than 2 hetero may be used as a patient selection criterion for treatment with a FOLR1 therapeutic agent (see e.g., U.S. Published Application No. 2012/0282175, which is herein incorporated by reference in its entirety).

FOLR1 expression analysis also identifies patients in whom decreased levels of a FOLR1-targeting anti-cancer therapy ("low dose therapy") can be effective to cause anti-tumor responses. As is appreciated in the art, compounds are generally administered at the smallest dosage that achieves the desired therapeutic response. This is specifically important for therapeutics that cause clinical side effects. The ability to recognize those subjects with elevated FOLR1 expression levels allows for minimization of the dosage of the FOLR1-targeting therapeutic, thus decreasing possible side effects, while maintaining therapeutic efficacy.

Accordingly, the antibodies and antigen-binding fragments provided herein are particularly advantageous for use in such methods because they are capable of detecting a dynamic range of FOLR1 expression levels, e.g., in IHC.

VI. Shed Antigen Assay

Measuring levels of circulating antigen in patient plasma samples (shed antigen) can help identify patient populations more likely to respond to treatment, e.g., antibody maytansinoid conjugate (AMC) treatment. High levels of shed antigen have been reported to markedly affect the pharmacokinetics of therapeutic antibodies (Tolcher A. et al. 20th Symposium on Molecular Targets and Cancer Therapeutics; Oct. 21-24, 2008; Geneva, Switzerland: EORTC-NCI-AACR, p163, #514; Baselga J, et al. J Clin Oncol 14:737-744 (1996)). It is likely that shed antigen levels from patient plasma samples will be variable depending on factors such as antigen target, disease indications, and disease course. Currently shed antigen levels in disease indications for the anti-FOLR1 immunoconjugate IMGN853 have been insufficiently examined while correlation with solid tumor expression is limited. While elevation of FOLR1 has been reported in ovarian adenocarcinomas, data suggests that it is not elevated in other FOLR1+ tumor indications, such as small cell lung carcinoma (Mantovani L T, et al. Eur J Cancer 30A(3):363-9 (1994); Basal E, et al. PLoS ONE 4(7): e6292 (2009)). The present method allows for detection of the FOLR1 receptor in the presence of high folic acid using the antibodies and antigen-binding fragments thereof that are provided herein and are capable of detecting dynamic ranges of shed FOLR1. Previous assays have used Mov19 in the design of the assay. Since IMGN853 contains Mov19 and in one embodiment is the targeted therapy of the invention, it is vital that the method detects FOLR1 in the presence or absence of Mov19. Previous assays that use Mov19 have competitive effects and will detect significantly less or no FOLR1 in patients receiving IMGN853 treatment.

In one embodiment, the present method for detecting FOLR1 in human sourced fluid samples uses a traditional sandwich ELISA format. In one embodiment, the method uses a capture agent (i.e., antibody) to FOLR1 attached to a solid support. In one embodiment, the solid support is a microtiter plate. To this, the sample (ascites fluids, plasma, etc.) is added without dilution, and is detected by a different detection agent (a different antibody), which does not interfere with the binding of the first capture agent. The detection agent is then detected through the use of a secondary detection agent (biotin/streptavidin, anti-human secondary mono or polyclonal antibody, etc.) which can bind more than one time to the first detection agent, thus amplifying the signal of detection. The secondary detection agent is then quantified by the use of some other means (e.g., TMB/peroxidase, scintillation counting, fluorescent probes, etc.).

Additionally, the assay detects FOLR1 and is not negatively impacted by the presence of Mov19, IMGN853, other FOLR1 family members, or folic acid.

The assays of the present invention include assays both to select patients eligible to receive FOLR1-based therapy and assays to monitor patient response. Assays for response prediction are run before therapy selection, and levels of FOLR1 may impact therapy decisions. For monitoring patient response, the assay is run at the initiation of therapy to establish baseline (or predetermined) levels of FOLR1 in the sample. The same sample is then assayed and the levels of FOLR1 compared to the baseline or predetermined levels. As used herein, the term "predetermined level" refers generally to an assay cutoff value that is used to assess diagnostic results by comparing the assay results against the predetermined level, and where the predetermined level already has been linked or associated with various clinical parameters (e.g., monitoring whether a subject being treated with a drug has achieved an efficacious blood level of the drug, monitoring the response of a subject receiving treatment for cancer with an anti-cancer drug, monitoring the response of a tumor in a subject receiving treatment for said tumor, etc.). The predetermined level may be either an absolute value or a value normalized by subtracting the value obtained from a patient prior to the initiation of therapy. An example of a predetermined level that can be used is a baseline level obtained from one or more subjects that may optionally be suffering from one or more diseases or conditions. The comparison (or informational analysis) of the level of the assayed biomarker with the baseline or predetermined level can be done by an automated system, such as a software program or intelligence system that is part of, or compatible with, the equipment (e.g., computer platform) on which the assay is carried out. Alternatively, this comparison or informational analysis can be done by a physician. In one embodiment, where the levels remain the same or decrease, the therapy may be effective and can be continued. Where significant increase over baseline level (or predetermined level) occurs, the patient may not be responding. In another embodiment, an increase in shed FOLR1 levels may be indicative of increased cell death and increased release of the shed FOLR1. In this embodiment, an increase in shed FOLR1 is indicative of therapeutic efficacy.

The assays of the present invention can be performed by any protein assay methods. Protein assay methods useful in the invention are well known in the art and include immunoassay methods involving binding of a specific unlabeled or labeled antibody or protein to the expressed protein or fragment of FOLR1. Useful immunoassay methods include both solution phase assays conducted using any format known in the art, such as, but not limited to, Biacore, time resolved fluorescence energy transfer (TR-FRET), an ELISA format, (sandwich, forward and reverse competitive inhibition) or a fluorescence polarization format, and solid phase assays such as immunohistochemistry. The FOLR1 antibodies and antigen-binding fragments thereof provided herein are particularly useful for these immunoassay methods because, for example, they are able to detect a dynamic range of FOLR1.

VII. Circulating Tumor Cell Assays

The anti-FOLR1 antibodies described herein can also be used for the detection of FOLR1 in a circulating tumor cell assay. Circulating tumor cells (CTCs) are cells that have shed into the vasculature from a tumor and circulate in the bloodstream. CTCs are present in circulation in extremely low numbers. In general, CTCs are enriched from patient blood or plasma by various techniques known in the art. CTCs can be stained for specific markers using methods known in the art including, but not limited to, flow cytometry-based methods and IHC-based methods. CTCs may be stained for protein markers unique to the tumor cells, which allows for the identification and distinction of CTCs from normal blood cells. CTCs can also be stained for FOLR1 using the antibodies provided herein including but not limited to 2.1, 5.7, and 9.20. CTC analysis can also include quantitative analysis of the number of CTCs and/or the number of FOLR1 positive CTCs. The FOLR1 antibodies described herein can be used to stain the CTCs isolated from a subject having a cancer to measure the FOLR1 present in the CTCs. An increase in FOLR1 expressing CTCs can help identify the subject as having a cancer that is likely to respond to FOLR1 based therapy or allow for optimization of a therapeutic regimen with a FOLR1 antibody or immunoconjugate. CTC FOLR1 quantitation can provide information on the stage of tumor, response to therapy and/or disease progression. It can be used as prognostic, predictive or pharmacodimamic biomarker. In addition, staining of CTCs for FOLR1 using the antibodies provided herein, can be used as a liquid biopsy either alone or in combination with additional tumor marker analysis of solid biopsy samples.

VIII. Detection

The present invention further provides antibodies against FOLR1, generally of the monoclonal type, that are linked to at least one agent to form a detection antibody conjugate. In order to increase the efficacy of antibody molecules as diagnostic it is conventional to link or covalently bind or complex at least one desired molecule or moiety. Such a molecule or moiety may be, but is not limited to, at least one reporter molecule. A reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles and/or ligands, such as biotin.

Certain examples of antibody conjugates are those conjugates in which the antibody or antigen-binding fragment thereof provided herein is linked to a detectable label. "Detectable labels" are compounds and/or elements that can be detected due to their specific functional properties, and/or chemical characteristics, the use of which allows the antibody or antigen-binding fragment to which they are attached to be detected, and/or further quantified if desired.

Many appropriate imaging agents are known in the art, as are methods for their attachment to antibodies (see, e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; and/or X-ray imaging, for example.

Exemplary fluorescent labels contemplated for use as binding agent (e.g., antibody) conjugates include Alexa 350, Alexa 430, Alexa 488, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Dylight 488, Fluorescein Isothiocyanate (FITC), Green fluorescent protein (GFP), HEX, 6-JOE, Oregon Green 488, Oregon Green 500, Oregon Green 514, Pacific Blue, Phycoerythrin, REG, Rhodamine Green, Rhodamine Red, tetramethyl rhodamin (TMR) Renographin, ROX, TAMRA, TET, Tetramethylrhodamine, Texas Red, and derivatives of these labels (i.e., halogenated analogues, modified with isothiocynate or other linker for conjugating, etc.), for example. An exemplary radiolabel is tritium.

Antibody or antigen-binding fragment detection conjugates contemplated in the present invention include those for use in vitro, where the antibody or fragment is linked to a secondary binding ligand and/or to an enzyme (an enzyme tag) that will generate a colored product upon contact with a chromogenic substrate. The FOLR1 antibodies and antigen-binding fragments thereof provided herein are particularly useful for conjugates methods because, for example, they are able to detect a dynamic range of FOLR1. Examples of suitable enzymes include urease, alkaline phosphatase, (horseradish) hydrogen peroxidase and/or glucose oxidase. In some embodiments, secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the binding agent (e.g., antibody) (U.S. Pat. Nos. 4,472,509 and 4,938,948, each incorporated herein by reference). Monoclonal antibodies may also be reacted with an enzyme in the presence of a coupling agent such as glutaraldehyde or periodate. Protein binding (e.g., antibody) conjugates with fluorescein markers are prepared in the presence of these coupling agents or by reaction with an isothiocyanate. In U.S. Pat. No. 4,938,948, imaging of breast tumors, for example, is achieved using monoclonal antibodies, and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region, have also been disclosed in the literature (O'Shannessy et al., 1987).

In other embodiments of the invention, immunoglobulins are radiolabeled with nuclides such as tritium. In additional embodiments, nanogold particles (such as sizes from about 0.5 nm-40 nm) and/or Quantum Dots (Hayward, Calif.) are employed.

When a sandwich assay format is used, the capture antibody will be unlabeled. The detection antibody will be either directly labeled, or detected indirectly by addition (after washing off excess detection antibody) of a molar excess of a second, labeled antibody directed against the first antibody.

The label used for the detection antibody is any detectable functionality that does not interfere with the binding of the FOLR1 antibodies. Examples of suitable labels are those numerous labels known for use in immunoassay, including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazindiones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-β-galactosidase with MUG, spin labels, bacteriophage labels, stable free radicals, and the like. As noted herein, the fluorimetric detection is one example.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the herein-described fluorescent, chemiluminescent, and enzyme labels. See, for example, U.S. Pat. No. 3,940,475 (fluorimetry) and U.S. Pat. No. 3,645,090 (enzymes); Hunter et al. Nature 144:945 (1962); David et al. Biochemistry 13:1014-1021 (1974); Pain et al. J. Immunol. Methods 40:219-230 (1981); and Nygren J. Histochem. and Cytochem. 30:407-412 (1982). In certain embodiments, labels herein are fluorescent to increase amplification and sensitivity to 8 pg/ml, more preferably biotin with streptavidin-β-galactosidase and MUG for amplifying the signal. In certain embodiments, a colorimetric label is used, e.g., where the detectable antibody is biotinylated and the detection means is avidin or streptavidin-peroxidase and 3,3',5,5'-tetramethyl benzidine.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring the amount of the attached label using a detection method appropriate to the label, and correlating the measured amount with the amount of shed FOLR1 in the biological sample. For example, in the case of enzymes, the amount of color developed and measured will be a direct measurement of the amount of shed FOLR1 present. Specifically, if HRP is the label, the color can be detected using the substrate 3,3',5,5'-tetramethyl benzidine at 450 nm absorbance.

IX. Substrates and Indicators

The use of substrates and indicators is contemplated for detection of FOLR1.

Horseradish peroxidase (HRP) is an enzyme that first forms a complex with hydrogen peroxide and then causes it to decompose, resulting in water and atomic oxygen. Like many other enzymes, HRP and some HRP-like activities can be inhibited by excess substrate. The complex formed between HRP and excess hydrogen peroxide is catalytically inactive and in the absence of an electron donor (e.g. chromogenic substance) is reversibly inhibited. It is the excess hydrogen peroxide and the absence of an electron donor that brings about quenching of endogenous HRP activities. When used in assay systems, HRP can also be used to convert a defined substrate into its activated chromagen, thus causing a color change. The HRP enzyme can be conjugated to an antibody, peptide, polymer, or other molecule by a number of methods that are known in the art. Adding glutaraldehyde to a solution containing an admixture of HRP and antibody will result in more antibody molecules being conjugated to each other than to the enzyme. In the two-step procedure, HRP reacts with the bifunctional reagents first. In the second stage, only activated HRP is admixed with the antibody, resulting in much more efficient labeling and no polymerization. HRP is also conjugated to (strept)avidin using the two-step glutaraldehyde procedure. This form is used in procedures where LAB and LSAB are substrates, for example. Conjugation with biotin also involves two steps, as biotin must first be derivatized to the biotinyl-N-hydroxysuccinimide ester or to biotin hydrazide before it can be reacted with the epsilonamino groups of the HRP enzyme.

3,3'-diaminobenzidine (DAB) is a substrate for enzymes such as HRP that produces a brown end product that is highly insoluble in alcohol and other organic solvents. Oxidation of DAB also causes polymerization, resulting in the ability to react with osmium tetroxide, and thus increasing its staining intensity and electron density. Of the several metals and methods used to intensify the optical density of polymerized DAB, gold chloride in combination with silver sulfide appears to be the most successful.

3-Amino-9-ethylcarbazole (AEC), is a substrate for enzymes such as HRP, and upon oxidation, forms a rose-red end product that is alcohol soluble. Therefore, specimens processed with AEC must not be immersed in alcohol or alcoholic solutions (e.g., Harris' hematoxylin). Instead, an aqueous counterstain and mounting medium should be used.

4-Chloro-1-naphthol (CN) is a substrate for enzymes such as HRP that precipitates as a blue end product. Because CN is soluble in alcohol and other organic solvents, the specimen must not be dehydrated, exposed to alcoholic counterstains, or coverslipped with mounting media containing organic solvents. Unlike DAB, CN tends to diffuse from the site of precipitation.

p-Phenylenediamine dihydrochloride/pyrocatechol (Hanker-Yates reagent) is a substrate for enzymes such as HRP that gives a blue-black reaction product that is insoluble in alcohol and other organic solvents. Like polymerized DAB, this reaction product can be osmicated. Varying results have been achieved with Hanker-Yates reagent in immunoperoxidase techniques.

Calf intestine alkaline phosphatase (AP) (molecular weight 100 kD) removes (by hydrolysis) and transfers phosphate groups from organic esters by breaking the P-O bond; an intermediate enzyme-substrate bond is briefly formed. The chief metal activators for AP are Mg++, Mn++ and Ca++.

AP had not been used extensively in immunohistochemistry until publication of the unlabeled alkaline phosphatase-anti-alkaline phosphatase (APAAP) procedure. The soluble immune complexes utilized in this procedure have molecular weights of approximately 560 kD. The major advantage of the APAAP procedure compared to the peroxidase anti-peroxidase (PAP) technique is the lack of interference posed by endogenous peroxidase activity. Endogenous peroxidase can be blocked using a dilute solution of hydrogen peroxide. Because of the potential distraction of endogenous peroxidase activity on PAP staining, the APAAP technique is recommended for use on blood and bone marrow smears. Endogenous alkaline phosphatase activity from bone, kidney, liver and some white cells can be inhibited by the addition of 1 mM levamisole to the substrate solution, although 5 mM has been found to be more effective. Intestinal alkaline phosphatases are not adequately inhibited by levamisole.

In the immunoalkaline phosphatase staining method, the enzyme hydrolyzes naphthol phosphate esters (substrate) to phenolic compounds and phosphates. The phenols couple to colorless diazonium salts (chromogen) to produce insoluble, colored azo dyes. Several different combinations of substrates and chromogens have been used successfully.

Naphthol AS-MX phosphate AP substrate can be used in its acid form or as the sodium salt. The chromogen substrate Fast Red TR and Fast Blue BB produce a bright red or blue end product, respectively. Both are soluble in alcoholic and other organic solvents, so aqueous mounting media must be used. Fast Red TR is preferred when staining cell smears.

Additional exemplary substrates include naphthol AS-BI phosphate, naphthol AS-TR phosphate and 5-bromo-4-chloro-3-indoxyl phosphate (BCIP). Other possible chromogens include Fast Red LB, Fast Garnet GBC, Nitro Blue Tetrazolium (NBT) and iodonitrotetrazolium Violet (INT), for example.

X. Immunodetection Methods

In still further embodiments, the present invention concerns immunodetection methods for binding, purifying, removing, quantifying and/or otherwise generally detecting biological components such as a ligand as contemplated by the present invention. The antibodies prepared in accordance with the present invention may be employed. Some immunodetection methods include immunohistochemistry, flow cytometry, enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, Methods Mol Biol. 1999; 109:215-37; Gulbis B and Galand P, Hum Pathol. 1993 December; 24(12):1271-85; and De Jager R et al., Semin Nucl Med. 1993 April; 23(2):165-79, each incorporated herein by reference.

In general, the immunobinding methods include obtaining a sample suspected of comprising ligand protein, polypeptide and/or peptide, and contacting the sample with a first ligand binding agent (e.g., an anti-ligand antibody) in accordance with the present invention, as the case may be, under conditions effective to allow the formation of immunocomplexes.

In terms of antigen detection, the biological sample analyzed may be any sample in which it is desirable to detect FOLR1 such as fluidic extract, blood, plasma, serum, spinal fluid, lymph fluid, tissue section or specimen, homogenized tissue extract, biopsy aspirates, a cell, separated and/or purified forms FOLR1-containing compositions, or any biological fluid. In some embodiments, blood, plasma, or lymph samples or extracts are used.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any ligand protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The anti-ligand antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding agent that has binding affinity for the antibody. In these cases, the second binding agent may be linked to a detectable label. The second binding agent is itself often an antibody, which may thus be termed a "secondary" antibody. The primary immune complexes are contacted with the labeled, secondary binding agent, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding agent, such as an antibody, that has binding affinity for the antibody is used to form secondary immune complexes, as described herein. After washing, the secondary immune complexes are contacted with a third binding agent or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

In another embodiment, a biotinylated monoclonal or polyclonal antibody is used to detect the target antigen(s), and a second step antibody is then used to detect the biotin attached to the complexed biotin. In that method the sample to be tested is first incubated in a solution comprising the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution comprising the second step antibody against biotin. This second step antibody is labeled, as for example with an enzyme that can be used to detect the presence of the antibody/antigen complex by histoenzymology using a chromogen substrate. With suitable amplification, a conjugate can be produced that is macroscopically visible.

In one embodiment, immunohistochemistry (IHC) is used for immunological detection. Using IHC, detection of FOLR1 in a sample can be achieved by targeting a sample with a probe e.g., an anti-FOLR1 antibody. The probe can be linked, either directly or indirectly to a detectable label or can be detected by another probe that is linked, either directly or indirectly to a detectable label.

In some embodiments, IHC can distinguish between different levels of protein expression, e.g., calibrated IHC. In some embodiments, the IHC can distinguish staining intensity for samples having low FOLR1, intermediate FOLR1, or high FOLR1 expression.

In one embodiment, immunological detection (by immunohistochemistry) of FOLR1 is scored for both intensity and uniformity (percent of stained cells—membrane only). Comparative scales for FOLR1 expression for intensity correlate as 0—Negative, 0-1—Very Weak, 1—Weak, 1-2—Weak to Moderate, 2—Moderate, 2-3—Moderate to Strong, 3—Strong, 3+—Very Strong. Quantitatively, Score 0 represents that no membrane staining is observed. Score 1 represents that a faint/barely perceptible membrane staining is detected. For Score 2, a weak to moderate complete membrane staining is observed. Lastly, Score 3 (or 3+) represents that moderate to complete membrane staining is observed. Those samples with 0 or 1 score for FOLR1 expression can be characterized as not having elevated FOLR1 expression, whereas those samples with 2 or 3 scores can be characterized as overexpressing or having elevated FOLR1. In another embodiment, using the antibodies, antigen-binding fragments thereof, or polypeptides provided herein, those samples with a 0 score for FOLR1 expression can be characterized as not having elevated FOLR1 expression, those samples with a 1 score can be characterized as having increased expression of FOLR1, and those samples with 2 or 3 scores can be characterized as overexpressing or having elevated FOLR1.

Samples overexpressing FOLR1 can also be rated by immunohistochemical scores corresponding to the number of copies of FOLR1 molecules expressed per cell, or antibodies bound per cell (ABC), and can been determined biochemically. Comparative scales for FOLR1 uniformity (percent cell membrane staining) are as follows: Negative=0%; Focal=<25%; heterogeneous (hetero)=25-75%, and homogeneous (homo)=>75%.

In one embodiment, immunological detection (by immunohistochemistry) of FOLR1 is scored using H-scores. H-scores combine staining intensity scores (e.g., a score of 0 to 3, wherein 0 represents no staining, and 3 represents strong staining) with the percentage of cells that are positive for membrane staining (i.e., uniformity). An H-score can be caclulated as follows: H score=[0*(percentage of cells staining at intensity 0)]+[1*(percentage of cells staining at intensity 1)]+[2*(percentage of cells staining at intensity 2)]+[3*(percentage of cells staining at intensity 3)]. Accordingly, an H-score can range from 0 (no cell membranes staining) to 300 (all cell membranes staining at intensity 3).

In one embodiment, a subject having cancer is identified as a candidate for treatment with an anti-FOLR1 treatment regimen (e.g., IMGN853) when the H-score for FOLR expression in a tumor sample from the subject is at least 50. In one embodiment, a subject having cancer is identified as a candidate for treatment with an anti-FOLR1 treatment regimen (e.g., IMGN853) when the H-score for FOLR expression in a tumor sample from the subject is at least 75. In one embodiment, a subject having cancer is identified as a candidate for treatment with an anti-FOLR1 treatment regimen (e.g., IMGN853) when the H-score for FOLR expression in a tumor sample from the subject is at least 100. In one embodiment, a subject having cancer is identified as a candidate for treatment with an anti-FOLR1 treatment regimen (e.g., IMGN853) when the H-score for FOLR expression in a tumor sample from the subject is at least 125. In one embodiment, a subject having cancer is identified as a candidate for treatment with an anti-FOLR1 treatment regimen (e.g., IMGN853) when the H-score for FOLR expression in a tumor sample from the subject is at least 150. In one embodiment, a subject having cancer is identified as a candidate for treatment with an anti-FOLR1 treatment regimen (e.g., IMGN853) when the H-score for FOLR expression in a tumor sample from the subject is at least 175. In one embodiment, a subject having cancer is identified as a candidate for treatment with an anti-FOLR1 treatment regimen (e.g., IMGN853) when the H-score for FOLR expression in a tumor sample from the subject is at least 200. In another embodiment, a subject having cancer is identified as a candidate for treatment with an anti-FOLR1 regimen (e.g., IMGN853) when the H-score for FOLR expression in a tumor sample from the subject is at least 225. In another embodiment, a subject having cancer is identified as a candidate for treatment with an anti-FOLR1 regimen (e.g., IMGN853) when the H-score for FOLR expression in a tumor sample from the subject is at least 250. In another embodiment, a subject having cancer is identified as a candidate for treatment with an anti-FOLR1 regimen (e.g., IMGN853) when the H-score for FOLR expression in a tumor sample from the subject is at least 275. In another embodiment, a subject having cancer is identified as a candidate for treatment with an anti-FOLR1 regimen (e.g., IMGN853) when the H-score for FOLR expression in a tumor sample from the subject is 300.

In another embodiment, a subject having ovarian cancer is identified as a candidate for treatment with an anti-FOLR1 regimen (e.g., IMGN853) when the H-score for FOLR expression in an ovarian tumor sample from the subject is 75 to 300. In another embodiment, a subject having ovarian cancer is identified as a candidate for treatment with an anti-FOLR1 regimen (e.g., IMGN853) when the H-score for FOLR expression in an ovarian tumor sample from the subject is at least 75. In another embodiment, a subject having ovarian cancer is identified as a candidate for treatment with an anti-FOLR1 regimen (e.g., IMGN853) when the H-score for FOLR expression in an ovarian tumor sample from the subject is at least 100. In another embodiment, a subject having ovarian cancer is identified as a candidate for treatment with an anti-FOLR1 regimen (e.g., IMGN853) when the H-score for FOLR expression in an ovarian tumor sample from the subject is at least 125. In another embodiment, a subject having ovarian cancer is identified as a candidate for treatment with an anti-FOLR1 regimen (e.g., IMGN853) when the H-score for FOLR expression in an ovarian tumor sample from the subject is at least 150. In another embodiment, a subject having ovarian cancer is identified as a candidate for treatment with an anti-FOLR1 regimen (e.g., IMGN853) when the H-score for FOLR expression in an ovarian tumor sample from the subject is at least 175. In another embodiment, a subject having ovarian cancer is identified as a candidate for treatment with an anti-FOLR1 regimen (e.g., IMGN853) when the H-score for FOLR expression in an ovarian tumor sample from the subject is at least 200. In another embodiment, a subject having ovarian cancer is identified as a candidate for treatment with an anti-FOLR1 regimen (e.g., IMGN853) when the H-score for FOLR expression in an ovarian tumor sample from the subject is at least 225. In another embodiment, a subject having ovarian cancer is identified as a candidate for treatment with an anti-FOLR1 regimen (e.g., IMGN853) when the H-score for FOLR expression in an ovarian tumor sample from the subject is at least 250. In another embodiment, a subject having ovarian cancer is identified as a candidate for treatment with an anti-FOLR1 regimen (e.g., IMGN853) when the H-score for FOLR expression in an ovarian tumor sample from the subject is at least 275. In another embodiment, a subject having ovarian cancer is identified as a candidate for treatment with an anti-FOLR1 regimen (e.g., IMGN853) when the H-score for FOLR expression in an ovarian tumor sample from the subject is 300.

In another embodiment, a subject having NSCLC is identified as a candidate for treatment with an anti-FOLR1 regimen (e.g., IMGN853) when the H-score for FOLR expression in an NSCLC tumor sample from the subject is 50 to 300. In another embodiment, a subject having NSCLC is identified as a candidate for treatment with an anti-FOLR1 regimen (e.g., IMGN853) when the H-score for FOLR expression in an NSCLC tumor sample from the subject is at least 50. In another embodiment, a subject having NSCLC is identified as a candidate for treatment with an anti-FOLR1 regimen (e.g., IMGN853) when the H-score for FOLR expression in an NSCLC tumor sample from the subject is at least 75. In another embodiment, a subject having NSCLC is identified as a candidate for treatment with an anti-FOLR1 regimen (e.g., IMGN853) when the H-score for FOLR expression in an NSCLC tumor sample from the subject is at least 100. In another embodiment, a subject having NSCLC is identified as a candidate for treatment with an anti-FOLR1 regimen (e.g., IMGN853) when the H-score for FOLR expression in an NSCLC tumor sample from the subject is at least 125. In another embodiment, a subject having NSCLC is identified as a candidate for treatment with an anti-FOLR1 regimen (e.g., IMGN853) when the H-score for FOLR expression in an NSCLC tumor sample from the subject is at least 150. In another embodiment, a subject having NSCLC is identified as a candidate for treatment with an anti-FOLR1 regimen (e.g., IMGN853) when the H-score for FOLR expression in an NSCLC tumor sample from the subject is at least 175. In another embodiment, a subject having NSCLC is identified as a candidate for treatment with an anti-FOLR1 regimen (e.g., IMGN853) when the H-score for FOLR expression in an NSCLC tumor sample from the subject is at least 200. In another embodiment, a subject having NSCLC is identified as a candidate for treatment with an anti-FOLR1 regimen (e.g., IMGN853) when the H-score for FOLR expression in an NSCLC tumor sample from the subject is at least 225. In another embodiment, a subject having NSCLC is identified as a candidate for treatment with an anti-FOLR1 regimen (e.g., IMGN853) when the H-score for FOLR expression in an NSCLC tumor sample from the subject is at least 250. In another embodiment, a subject having NSCLC is identified as a candidate for treatment with an anti-FOLR1 regimen (e.g., IMGN853) when the H-score for FOLR expression in an NSCLC tumor sample from the subject is at least 275. In another embodiment, a subject having NSCLC is identified as a candidate for treatment with an anti-FOLR1 regimen (e.g., IMGN853) when the H-score for FOLR expression in an NSCLC tumor sample from the subject is 300.

In another embodiment, a subject having endometrial cancer is identified as a candidate for treatment with an anti-FOLR1 regimen (e.g., IMGN853) when the H-score for FOLR expression in an endometrial tumor sample from the subject is 50 to 300. In another embodiment, a subject having endometrial cancer is identified as a candidate for treatment with an anti-FOLR1 regimen (e.g., IMGN853) when the H-score for FOLR expression in an endometrial tumor sample from the subject is at least 50. In another embodiment, a subject having endometrial cancer is identified as a candidate for treatment with an anti-FOLR1 regimen (e.g., IMGN853) when the H-score for FOLR expression in an endometrial tumor sample from the subject is at least 75. In another embodiment, a subject having endometrial cancer is identified as a candidate for treatment with an anti-FOLR1 regimen (e.g., IMGN853) when the H-score for FOLR expression in an endometrial tumor sample from the subject is at least 100. In another embodiment, a subject having endometrial cancer is identified as a candidate for treatment with an anti-FOLR1 regimen (e.g., IMGN853) when the H-score for FOLR expression in an endometrial tumor sample from the subject is at least 125. In another embodiment, a subject having endometrial cancer is identified as a candidate for treatment with an anti-FOLR1 regimen (e.g., IMGN853) when the H-score for FOLR expression in an endometrial tumor sample from the subject is at least 150. In another embodiment, a subject having endometrial cancer is identified as a candidate for treatment with an anti-FOLR1 regimen (e.g., IMGN853) when the H-score for FOLR expression in an endometrial tumor sample from the subject is at least 175. In another embodiment, a subject having endometrial cancer is identified as a candidate for treatment with an anti-FOLR1 regimen (e.g., IMGN853) when the H-score for FOLR expression in an endometrial tumor sample from the subject is at least 200. In another embodiment, a subject having endometrial cancer is identified as a candidate for treatment with an anti-FOLR1 regimen (e.g., IMGN853) when the H-score for FOLR expression in an endometrial tumor sample from the subject is at least 225. In another embodiment, a subject having endometrial cancer is identified as a candidate for treatment with an anti-FOLR1 regimen (e.g., IMGN853) when the H-score for FOLR expression in an endometrial tumor sample from the subject is at least 250. In another embodiment, a subject having endometrial cancer is identified as a candidate for treatment with an anti-FOLR1 regimen (e.g., IMGN853) when the H-score for FOLR expression in an endometrial tumor sample from the subject is at least 275. In another embodiment, a subject having endometrial cancer is identified as a candidate for treatment with an anti-FOLR1 regimen (e.g., IMGN853) when the H-score for FOLR expression in an endometrial tumor sample from the subject is 300.

By way of example, an H-score in a subject having ovarian cancer may be as follows:

$$H \text{ score} = (75\% \text{ at intensity } 0) + (0\% \text{ at intensity } 1) + (0\% \text{ at intensity } 2) + (25\% \text{ at intensity } 3) = 75; \text{ or}$$

$$H \text{ score} = (0\% \text{ at intensity } 0) + (75\% \text{ at intensity } 1) + (0\% \text{ at intensity } 2) + (25\% \text{ at intensity } 3) = 150.$$

In another example, an H-score in a subject having endometrial cancer may be as follows:

$$H \text{ score} = (75\% \text{ at intensity } 0) + (0\% \text{ at intensity } 1) + (25\% \text{ at intensity } 2) + (0\% \text{ at intensity } 3) = 50; \text{ or}$$

$$H \text{ score} = (0\% \text{ at intensity } 0) + (75\% \text{ at intensity } 1) + (25\% \text{ at intensity } 2) + (0\% \text{ at intensity } 3) = 125.$$

In all four examples above, the subject could be identified as a candidate for treatment with an anti-FOLR1 treatment regimen (e.g., IMGN853).

In one embodiment, immunological detection (by immunohistochemistry) of FOLR1 is scored using percent positivity and intensity across a sample. In this embodiment, selection for treatment with an anti-FOLR1 treatment regimen is based on the percentage of cells in a sample that are found to express membrane FOLR1 at a specified level that reflects both the staining intensity (e.g., 1, 2, or 3) and uniformity (e.g., heterogeneous or homogeneous (see Table 11)). For example, a sample having at least 25% (i.e., 25-75% or >75%) of the cells staining for FOLR1 positivity at 3 could be characterized as "3 hetero" and "3 homo" or, collectively, as "at least 25% positive at 3."

In one embodiment, a subject having ovarian cancer is identified as a candidate for treatment with an anti-FOLR1 treatment regimen (e.g., IMGN853) when at least 25% of the FOLR1 membrane expression in a tumor sample from the subject has an intensity score of 3 by IHC. In one embodiment, the IHC is performed using the FOLR1-2.1 antibody.

In another embodiment, a subject having endometrial cancer is identified as a candidate for treatment with an anti-FOLR1 treatment regimen (e.g., IMGN853) when at least 25% of the FOLR membrane expression in a tumor sample from the subject has an intensity score of at least 2 by IHC. In one embodiment, the IHC is performed using the FOLR1-2.1 antibody.

In another embodiment, a subject having NSCLC is identified as a candidate for treatment with an anti-FOLR1 treatment regimen (e.g., IMGN853) when at least 25% of the FOLR membrane expression in a tumor sample from the subject has an intensity score of at least 2 by IHC. In one example, the IHC is performed using the FOLR1-2.1 antibody for IHC.

IHC can be performed manually or using an automated system (e.g., using an automated stainer). IHC can be performed on cells, cell pellets, tissues, preparations from blood, plasma, serum, or lymph fluid, etc. In some embodiments, the samples are fixed samples. In some embodiments, the samples are paraffin embedded samples. In some embodiments, the samples are formalin fixed and paraffin embedded samples.

In one embodiment, flow cytometry is used for immunological detection. Thus, for example, the number of antibodies bound per cell (ABC) can be assessed using flow cytometry. A high number of anti-FOLR1 antibodies bound per cell can indicate high FOLR1 expression levels and a high likelihood to be susceptible to treatment with an anti-FOLR1 antibody or immunoconjugate thereof.

XI. Compositions and Kits

Also provided by the invention are compositions and kits for use in the practice of the present invention as disclosed herein. Such kits may comprise containers, each with one or more of the various reagents (typically in concentrated form) utilized in the methods, including, for example, one or more binding agents (antibodies), already attached to a marker or optionally with reagents for coupling a binding agent to an antibody (as well as the marker itself), buffers, and/or reagents and instrumentation for the isolation (optionally by microdissection) to support the practice of the invention. A label or indicator describing, or a set of instructions for use of, kit components in a ligand detection method of the present invention, will also be typically included, where the instructions may be associated with a package insert and/or the packaging of the kit or the components thereof.

In still further embodiments, the present invention concerns immunodetection kits for use with the immunodetection methods described herein. As the antibodies are generally used to detect FOLR1, the antibodies will generally be included in the kit. The immunodetection kits will thus comprise, in suitable container means, a first antibody that binds to FOLR1 and/or optionally, an immunodetection reagent and/or further optionally, a FOLR1 protein or cell sample containing FOLR1.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted herein, a number of exemplary labels are known in the art and/or all such labels may be suitably employed in connection with the present invention.

The kits may further comprise a therapeutic agent for the treatment of cancer, such as an anti-FOLR1 immunoconjugate.

The kit may further comprise an a FOLR1 detection reagent used to measure FOLR1 expression in a subject comprising a FOLR1 detection reagent, and instructions for use. In one embodiment, the FOLR1 detection reagent comprises a FOLR1 binding peptide or anti-FOLR1 antibody. In another embodiment, the kit further comprises a secondary antibody which binds the anti-FOLR1 antibody.

In one embodiment the FOLR1-specific antibody is included at a concentration of about 0.1 to about 20 µg/mL, about 0.1 to about 15 µg/mL, about 0.1 to about 10 µg/mL, about 0.5 to about 20 µg/mL, about 0.5 to about 15 µg/mL, about 0.5 to about 10 µg/mL, about 1 to about 20 µg/mL, about 1 to about 15 µg/mL, about 1 to about 10 µg/mL, about 2 to about 20 µg/mL, about 2 to about 15 µg/mL, or about 2 to about 10 µg/mL. In another embodiment, the FOLR1-specific antibody is included at a concentration of about 1.5 µg/mL, about 2 µg/mL, about 3 µg/mL, about 4 µg/mL, about 5 µg/mL, about 6 µg/mL, about 7 µg/mL, about 8 µg/mL, about 9 µg/mL, or about 10 µg/mL. In another embodiment, the FOLR1-specific antibody is included at a concentration of about 2 µg/mL. In another embodiment, the FOLR1-specific antibody is included at a concentration of about 10 µg/mL.

In another embodiment, the antibody is included in concentrated solution with instructions for dilutions to achieve a final concentration of about 1 to about 20 µg/mL, about 1 to about 15 µg/mL, about 1 to about 10 µg/mL, about 2 to about 20 µg/mL, about 2 to about 15 µg/mL, or about 2 to about 10 µg/mL. In another embodiment, the antibody is included in concentrated solution with instructions for dilutions to achieve a final concentration of about 1.5 µg/mL, about 2 µg/mL, about 3 µg/mL, about 4 µg/mL, about 5 µg/mL, about 6 µg/mL, about 7 µg/mL, about 8 µg/mL, about 9 µg/mL, or about 10 µg/mL. In another embodiment, the antibody is included in concentrated solution with instructions for dilutions to achieve a final concentration of about 2 µg/mL. In another embodiment, the antibody is included in concentrated solution with instructions for dilutions to achieve a final concentration of about 10 µg/ml.

In another embodiment, the kit further comprises a detection reagent selected from the group consisting of: an enzyme, a fluorophore, a radioactive label, and a luminophore. In another embodiment, the detection reagent is selected from the group consisting of: biotin, digoxigenin, fluorescein, tritium, and rhodamine.

The kit can also include instructions for detection and scoring of FOLR1 expression. The kit can also include control or reference samples. Non-limiting examples of control or reference samples include cell pellets or tissue culture cell lines derived from normal (normal control) or tumor (positive control) samples. Exemplary cell lines include cell lines stably or transiently transfected with an expression vector that expresses FOLR1. Additional examples include cell pellets and tissue samples described in the Examples.

In some embodiments, a kit is a packaged combination including the basic elements of: (a) capture reagents comprised of the monoclonal antibodies against human FOLR1; and (b) detection reagents which can also comprise FOLR1 monoclonal antibodies, but can also comprise detectable (labeled or unlabeled) antibodies that bind to FOLR1. These basic elements are defined herein.

In one embodiment, the kit further comprises a solid support for the capture reagents, which can be provided as a separate element or on which the capture reagents are already immobilized. Hence, the capture antibodies in the kit can be immobilized on a solid support, or they can be immobilized on such support that is included with the kit or provided separately from the kit.

In one embodiment, the capture reagent is coated on a microtiter plate. The detection reagent can be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, and where the label is a fluorophore, a dye precursor that provides the detectable chromophore. Where the detection reagent is unlabeled, the kit can further comprise a detection means for the detectable antibodies, such as the labeled antibodies directed to the unlabeled antibodies, e.g., in a fluorimetric-detected format. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or β-galactosidase with MUG.

In one embodiment, the capture reagent is the FOLR1 antibody 2.1, 5.7, or 9.20 or an antibody comprising the sequences of antibody 2.1, 5.7 or 9.20. In one embodiment, the detection reagent is the FOLR1 antibody 2.1, 5.7, or 9.20 or an antibody comprising the sequences of antibody 2.1, 5.7 or 9.20. In another embodiment, the detection reagent FOLR1 antibody 2.1, 5.7, or 9.20 or an antibody comprising the sequences of antibody 2.1, 5.7 or 9.20 is biotinylated.

The kit also typically contains instructions for carrying out the assay, and/or FOLR1 protein, or fragments thereof (e.g., FOLR1 extracellular domain or the FOLR1 extracellular domain and all or a part of the GPI linkage domain) as an antigen standard, as well as other additives such as stabilizers, washing and incubation buffers, and the like. In one embodiment, the FOLR1 antigen standard is a FOLR1-Fc immunoadhesin. The kit can also include instructions for detection and scoring of FOLR1 expression.

The components of the kit can be provided in predetermined ratios, with the relative amounts of the various reagents suitably varied to provide for concentrations in solution of the reagents that substantially maximize the sensitivity of the assay. Particularly, the reagents can be provided as dry powders, usually lyophilized, including excipients, which on dissolution will provide for a reagent solution having the appropriate concentration for combining with the sample to be tested.

Compositions comprising the antibodies or antigen-binding fragments described herein are also provided. In one embodiment, a composition comprises an anti-FOLR1 antibody or antigen-binding fragment described herein and a buffer, e.g., a buffer that can be used in a detection assay such as FACS, IHC, or ELISA. Such buffers are known to those of ordinary skill in the art and include diluents. By way of example, certain FACS buffers are provided herein, e.g., in the working examples. FACS buffers can also contain, for example, serum or albumin (such as calf serum, goat serum, or BSA) and/or sodium azide. FACS buffers can also contain PBS, EDTA, and/or DNAse or any combination thereof. IHC buffers are also provided herein and known to those of ordinary skill in the art. IHC buffers can contain, for example, casein serum or albumin (such as calf serum, goat serum, or BSA), Tween or Triton, PBS and/or sodium azide or any combination thereof. ELISA buffers are also provided herein and known to those of ordinary skill in the art. ELISA buffers can contain, for example, serum or albumin (such as calf serum, goat serum, or BSA), non-fat dry milk, casein, and/or gelatin or any combination thereof.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1

Generation of FOLR1 Hybridomas

Hybridomas producing anti-human FOLR1 monoclonal antibodies that are suitable for immunohistochemistry (IHC) staining (antibodies of the invention) were selected from more than 16,000 hybridomas. The hybridomas were produced by immunization of wild-type Balb/c mice with different antigens including: formalin fixed 300-19 cells that have been transfected with human FOLR1, human FOLR1-murine IgG2a Fc recombinant protein, and human FOLR1 recombinant protein. The immunization with fixed 300-19 cells was conducted by subcutaneous injection of transfected 300-19 cells in PBS (5E6 cells/mouse/injection) in the absence of any adjuvant. The immunization with FOLR1 recombinant proteins was done by subcutaneous injection of the protein emulsified in complete Freund's adjuvant (CFA) or incomplete Freund's adjuvant for boost (Sigma) or Magic mouse adjuvant (Creative Diagnostics). Generally, mice were immunized five times with two week intervals before receiving a final boost by intraperitoneal injection of the immunogen three days prior to fusion.

A total of 16 independent fusions (including fusions 352, 353, and 354) were carried out using spleen cells that originated from the immunized wild-type Balb/c mice and murine myeloma P3X63Ag8.653 cells (P3 cells). Cell fusion was conducted using an ECM200 electrofusion machine (BTX Harvard Apparatus) according to standard protocols. Each fusion yielded more than 1,000 hybridomas. Antibodies produced by these hybridomas were screened and confirmed by a FACS based method using denatured FOLR1-positive and FOLR1-negative cells. Of the greater than 16,000 hybridomas screened, 14 hybridomas that were positive by FACS screening were discovered. All of the positive hybridomas originated from mice immunized with human FOLR1-murine IgG2a Fc recombinant protein.

Of the 14 hybridomas which were initially positive by FACS screening, only ten showed a sufficient IgG concentration for further analysis.

Example 2

Immunohistochemical Evaluation of Hybridoma Supernatants

Ten of the initial 14 hybridomas were analyzed by IHC. The analysis was performed using the Leica Bond RX Automated Stainer and the reagents and conditions listed in Table 9.

TABLE 9

IHC Reagents and Assay Conditions

| Step | Action/Reagent (Vendor) | Time |
|---|---|---|
| Bake | Temperature: 60° C. | 30 Minutes |
| Dewax | Bond Dewax Solution (Leica) 100% Ethanol (Pharmco Aaper) | Fixed |
| Antigen Retrieval | Bond Epitope Retrieval 2 (ethylenediaminetetraacetic acid based pH 9.0 solution) | 20 Minutes |
| Endogenous Peroxidase Block | Peroxide (Leica) | 5 Minutes |
| Test Article | ImmunoGen, Inc. generated antibodies at varying concentrations prepared by diluting in Leica Antibody Diluent | 15 Minutes |

TABLE 9-continued

IHC Reagents and Assay Conditions

| Step | Action/Reagent (Vendor) | Time |
|---|---|---|
| Detection | Post Primary Regent (Leica) | 8 Minutes |
| | Polymer (Leica) | 8 Minutes |
| | Mixed DAB (Leica) | 10 Minutes |
| Counterstain | Hematoxylin (Leica) | 5 Minutes |

Slides containing formalin fixed paraffin embedded (FFPE) cells, normal tissues, patient lung tumor biopsies, and patient ovarian tumor biopsies were baked at 60° C. and dewaxed using Bond Dewax Solution and 100% Ethanol. Heat induced epitope retrieval using Bond Epitope Retrieval 2 (ethylenediaminetetraacetic acid based pH 9.0 solution) was performed for 20 minutes and endogenous peroxidase was blocked with peroxide for 5 minutes. Slides were incubated with ImmunoGen, Inc. generated antibodies or Leica/Novocastra muIgG1 control antibodies at varying concentrations for 15 minutes. Bound antibodies were detected by incubation with the Leica Bond Refine detection system. Following the application of the antibodies, slides were incubated with Post Primary Reagent (rabbit anti-mouse IgG) for 8 minutes, Polymer (goat anti-rabbit polymer) for 8 minutes, and DAB (3,3-diaminobenzidine tetrahydrochloride) for 10 minutes which resulted in a brown color signal. Slides were counterstained with hematoxylin for 5 minutes.

FFPE tissue samples were derived from human tissue blocks obtained from Proteogenex and the Cooperative Human Tissue Network (CHTN) as outlined below. FFPE cell samples were derived from the KB cell line supplied by American Tissue Culture Collection. Slides containing sections of samples were prepared from FFPE blocks using a microtome set at 5 μm and were mounted on positively charged slides. These slides were allowed to air dry overnight prior to staining

TABLE 10

FFPE Test Samples

| Human Tissue Type | Commercial Source |
|---|---|
| Normal Lung | CHTN |
| Normal Pancreas | CHTN |
| Normal Salivary Gland | CHTN |
| Ovarian Papillary Serous Adenocarcinoma | Proteogenex |
| Lung Adenocarcinoma | CHTN |

FOLR1 staining intensity and distribution patterns were scored relative to control IgG staining (non-specific). Intensity was scored on a scale of 0 to 3 where 0=no staining, 1=weak staining, 2=moderate staining, and 3=strong staining Uniformity of the staining was scored as negative (no cells exhibit positive staining), focal (<25% of cells stained), heterogeneous (25-75% of cells stained), and homogeneous (>75% of cells stained). The staining intensity and scoring scales are described below. All staining was evaluated by a Board certified pathologist.

TABLE 11

| Intensity and Uniformity of Staining | | | |
|---|---|---|---|
| Intensity (Amount of Membrane Staining) | | Uniformity (Percent of Positive Cells) | |
| 0 | Negative | 0 | Negative |
| 1 | Weak | Focal | <25% |
| 2 | Moderate | Heterogeneous (hetero) | 25-75% |
| 3 | Strong | Homogeneous (homo) | >75% |

IHC Selection Process to Identify Hybridoma(s) for FFPE FOLR1 IHC

Primary clones positive by FACS on FOLR1-positive denatured cells (ten clones total) were evaluated by IHC. Two clones were obtained from fusion 352 (clones 352.1 and 352.2). Six clones were obtained from fusion 353 (clones 353.1, 353.2, 353.3, 353.5, 353.9, 353.15), and two clones were obtained from fusion 354 (clones 354.1 and 354.2). Hybridoma supernatants were collected from the cultured hybridoma cells and used for the analysis. Antibody concentrations in hybridoma supernatants were determined by ELISA using anti-murine L-chain specific polyclonal antibody to capture murine monoclonal antibody from supernatant and anti-murine Fc-specific polyclonal antibody to detect the captured antibody; murine monoclonal IgG1 sample with know concentration was used as a standard to calculate IgG concentration. Cell culture media (undiluted) was shown not to interfere with IHC staining methods (no background/non-specific staining was noted when media was used in place of the primary antibody). Ten supernatants (IMGN 352.1, 352.2, 353.1, 353.2, 353.3, 353.5, 353.9, 353.15, 354.1, and 354.2) diluted at varying concentrations up to 10 μg/mL in Leica Antibody Diluent were stained using FOLR1 known positive control samples (human normal lung, patient derived ovarian serous papillary adenocarcinoma, and KB cells) and evaluated to identify positive candidate clones (clones depicting acceptable membrane staining and specificity in FOLR1 positive samples). Five of the ten clones exhibited acceptable membrane staining in FOLR1 positive samples and good specificity. A suitable staining concentration was experimentally determined for each of the five candidate clones as follows: 353.1 (0.7 μg/mL), 353.2 (2.3 μg/mL), 353.3 (2.3 μg/mL), 353.5 (2 μg/mL and 10 μg/mL), and 353.9 (2 μg/mL and 10 μg/mL). Of the remaining 5 clones, clone 353.15 (stained at 2 and 10 μg/mL) exhibited acceptable membrane staining in KB cells and normal lung tissue; however, cytoplasmic staining only was observed in the patient ovarian tumor tissue tested. Clones 352.1, 352.2, and 354.1 exhibited no visible staining in any samples and clone 354.2 exhibited only apparent non-specific cytoplasmic staining, all considered unacceptable.

The five candidate clones were further subcloned. Subclones for four clones (353.2, 353.3, 353.5 and 353.9) were successfully identifiedno subclones of clone 353.1 was generated. A total of eight subclones were purified. Two subclones were obtained from clone 353.5 (353.5-7 and 353.5-10). Two subclones were obtained from clone 353.9 (353.9-20 and 353.9-21). Two subclones were obtained from clone 353.3 (353.3-8 and 353.3-9), and two subclones were obtained from clone 353.2 (353.2-1 and 353.2-12). (Note that these subclones are also referred to as 5.7, 5.10, 9.20, 9.21, 3.8, 3.9, 2.1, and 2.12, respectively.) IHC characterization of the subclones was performed using methods described above (Table 9: IHC Reagents and Assay Conditions) at antibody concentrations of 2 and 10 μg/mL. The eight subclones were also sequenced as described in Example 3, below. The candidate subclones were further evaluated to identify and rank for optimal membrane staining and specificity as follows: [353.2-1, 353.2-12], [353.9-20, 353.9-21], [353.5-7,353.5-10], and [353.3-8, 353.3-9]

and were selected for further characterization (subclones are bracketed together according to sequence identity as described in Example 3).

Figure 1:
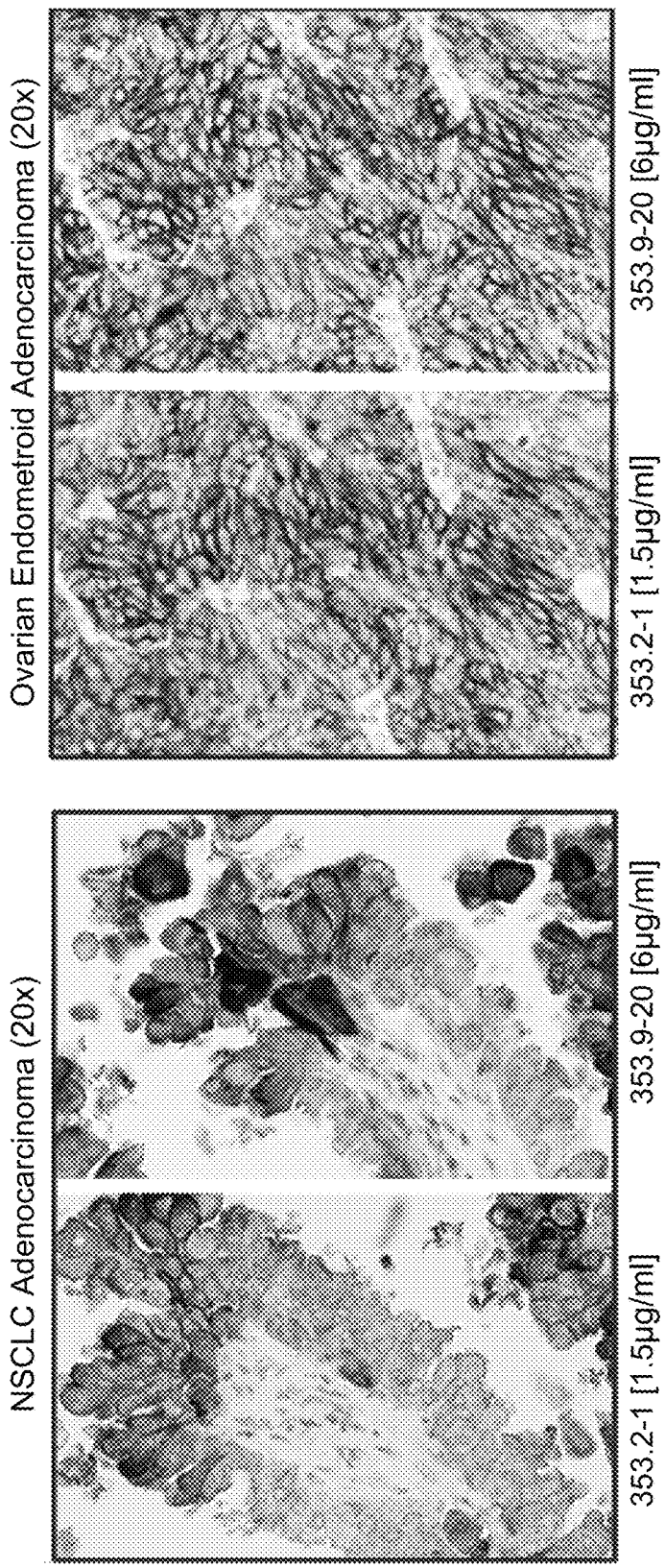
Figure 2:
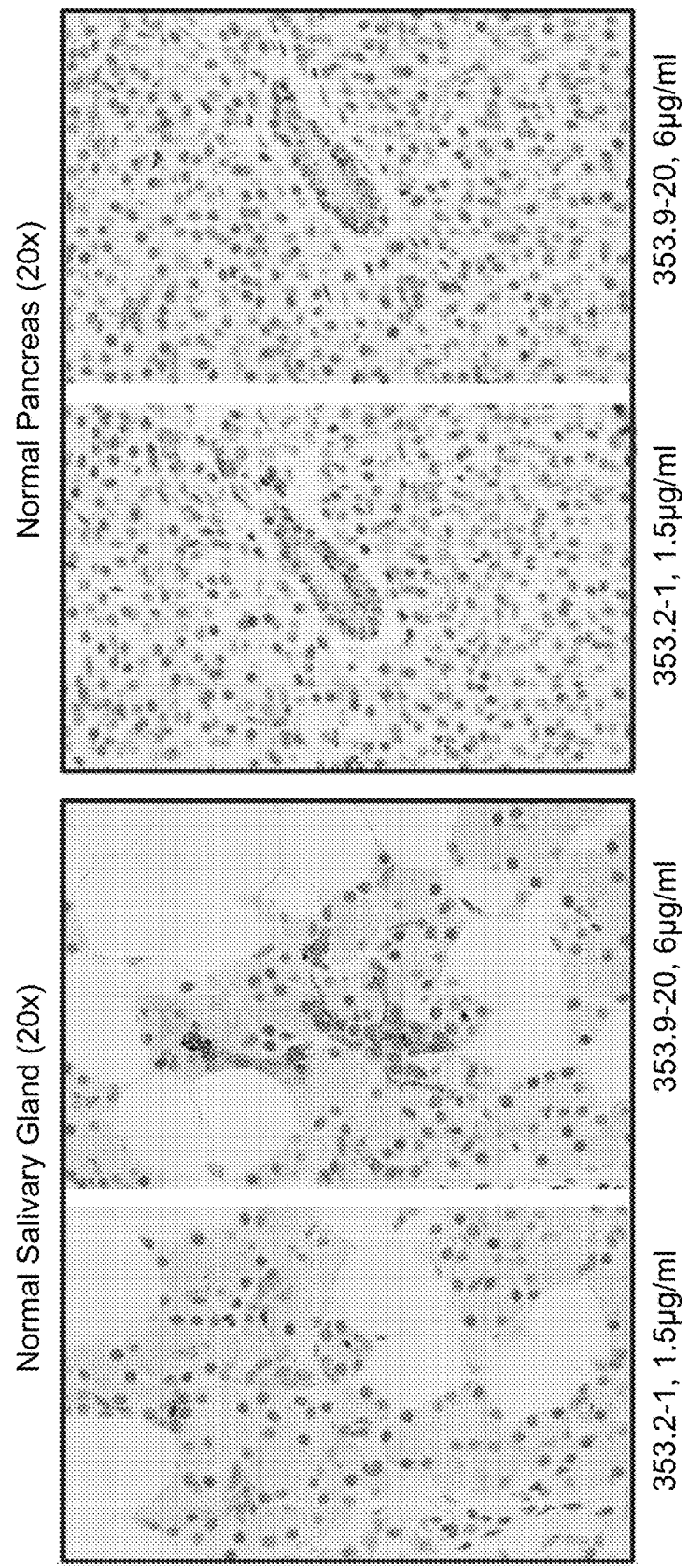

Two subclones were selected for further IHC assay optimization: 353.2-1 and 353.9-20. Both antibodies were used to stain human normal lung, human normal salivary gland, human normal pancreas, patient ovarian cancer biopsies, patient non-small cell lung cancer (NSCLC) biopsies, and patient clear cell renal cell carcinoma biopsies. At optimal conditions (see Table 12 below and FIG. 13), both subclones exhibited specific and appropriately sensitive staining in both human normal and patient tumor tissues. Ducts of pancreas, respiratory epithelium of normal lung, and intercalated ducts exhibited positive membrane associated staining Acinar cells/islets of pancreas, interalveolar connective tissue of lung, and acinar cells of salivary gland expected to be negative did not exhibit positive staining with either subclone. Tumor cells from ovarian cancer, NSCLC, and clear cell renal cell carcinoma samples expected to be positive exhibited positive membrane associated staining that was localized to the tumor cells. Tumor substructures expected to be negative (stroma, vessels, and lymphocytes) did not exhibit positive staining with 353.2-1 or 353.9-20. Additional staining of normal tissues with 353-2.1 (FOLR1-2.1) are summarized in Table 13, below and shown in FIG. 14. Taken together, the IHC characterization data suggests that 353.2-1 and 353.9-20 are specific to FOLR1 in FFPE tissues (see FIG. 1 and FIG. 2).

TABLE 12

Optimized Assay Conditions

| Step | Action/Reagent (Vendor) | Time |
|---|---|---|
| Bake | Temperature: 60° C. | 30 Minutes |
| Dewax | Bond Dewax Solution (Leica) 100% Ethanol (Pharmco Aaper) | Fixed |
| Antigen Retrieval | Bond Epitope Retrieval 2 (ethylenediaminetetraacetic acid based pH 9.0 solution) | 20 Minutes |
| Endogenous Peroxidase Block | Peroxide (Leica) | 5 Minutes |
| Test Article | IMGN353.2-1 at 1.5 µg/mL IMGN353.9-20 at 6.0 µg/mL | 15 Minutes |
| Detection | Post Primary Regent (Leica) | 8 Minutes |
|  | Polymer (Leica) | 8 Minutes |
|  | Mixed DAB (Leica) | 10 Minutes |
| Counterstain | Hematoxylin (Leica) | 5 Minutes |

TABLE 13

Optimized Assay Conditions

| Normal Tissue, Structure | 2.1 Staining |
|---|---|
| Adrenal Gland | + |
| Breast lobules | + |
| Fallopian tube, surface epithelium | + |
| Kidney, tubules | + |
| Pancreas, ducts | + |
| Pituitary, pituitary cells | + |
| Salivary gland, intercalated ducts | + |
| Breast, connective tissue | − |
| Esophagus submucosa & muscularis | − |
| Eye, cornea | − |
| Kidney, glomeruli | − |
| Lung, interalveolar connective tissue | − |
| Liver, hepatocytes | − |
| Pancreas, acinar cells | − |
| Lung, epithelium | −/+ |
| Stomach, surface epithelium, pits | − |

Example 3

Characterization of the Selected Anti-FOLR1 Antibodies

As described above in Example 2, of the fourteen hybridoma clones selected based on primary and confirmation FACS screening, ten primary clones were analyzed by immunohistochemistry (IHC) analysis. Of the ten primary clones (i.e., 352.1, 352.2, 353.1, 353.2, 353.3, 353.5, 353.9, 353.15, 354.1, and 354.2), five were positive by IHC (i.e., 353.1, 353.2, and 353.3, 353.5, and 353.9), and all five were derived from the same fusion (fusion 353). Four of the five were successfully subcloned. One subclone of primary clone 353.2 was chosen and named 353.2-1 ("2.1"). One subclone of primary clone 353.3 was chosen and named 353.3-8 ("3.8"). One subclone of primary clone 353.5 was chosen and named 353.5-7 ("5.7"), and two subclones of primary clone 353.9 were chosen and named 353.9-20 ("9.20") and 353.9-21 ("9.21"). Subclones 9.20 and 9.21 were sequenced, and as expected, both subclones had the same sequence. In addition, two of the clones, 2.1 and 9.20 were deposited with ATCC as PTA-120197 and PTA-120196, respectively, on Apr. 16, 2013.

Specificity of the Anti-FOLR1 Antibodies by Western Blot

Figure 3:
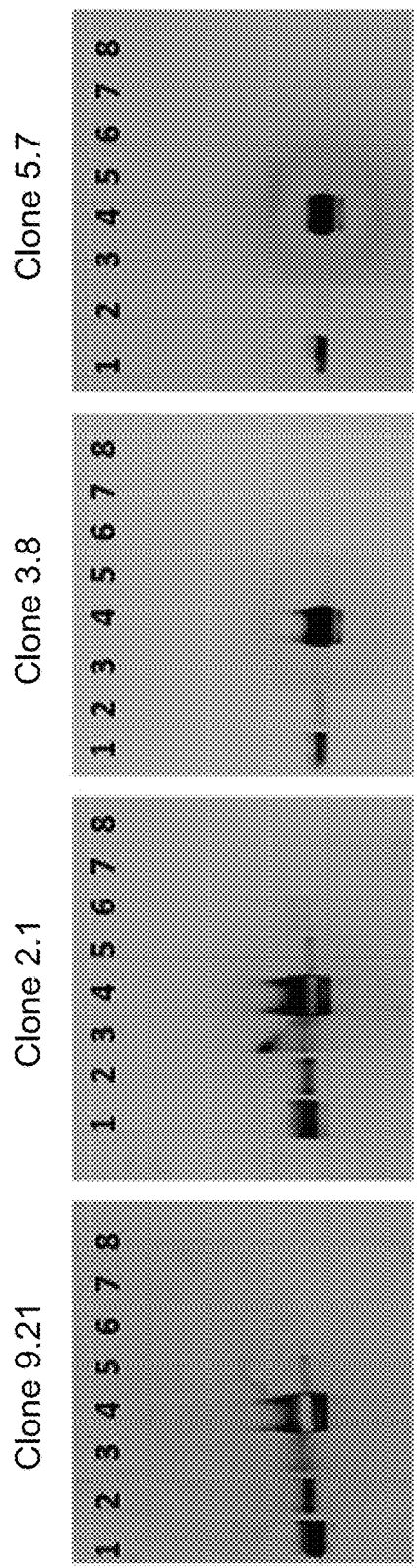

Specificity of the generated antibodies was analyzed by Western blot with a panel of cell lysates prepared from FOLR1-positive (Igrov-1, Ovcar-3, Caov-3, Wish, and Skov-3) and FOLR1-negative (BxPC3, Panc-1, and ASPC1) cell lines. For the assay, lysates were run in SDS polyacrylamide gel electrophoresis and transferred to a nitrocellulose membrane by the standard procedures. The membrane was incubated with the anti-FOLR1 antibodies of the invention, and the formed antigen-antibody complexes were detected with secondary anti-murine antibodies conjugated with horse-radish peroxidase (hrp) (FIG. 3). All tested anti-FOLR1 antibodies recognized FOLR1 in cell lines with high levels of FOLR1 expression (i.e., Igrov-1 and Wish). FOLR1 in low expressing cell lines Ovcar-3, Caov-3 and Skov-3 was detected only by anti-FOLR1 clones 2.1 and 9.21; clones 3.8 and 5.7 did not stain these cell lysates perhaps due to insufficient sensitivity of the antibodies. No additional non-specific bands were detected in FOLR1-positive cell lines by the clones; no staining of FOLR1-negative cell lines was observed.

Binding of the Anti-FOLR1 Antibodies to Denatured and not Denatured Cells

Figure 4A:
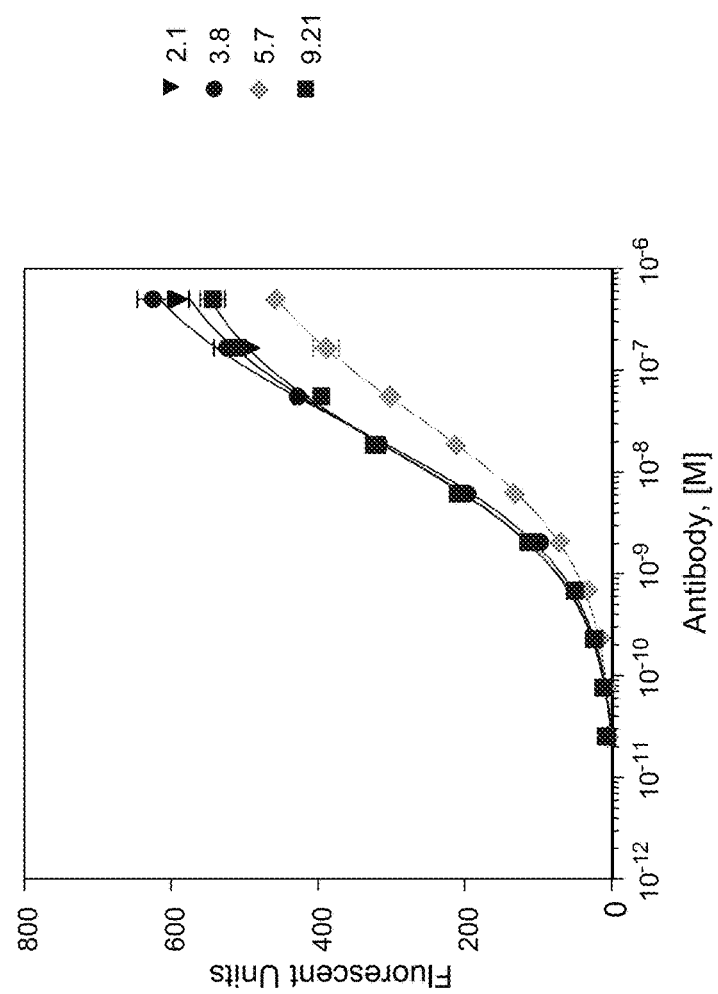
FIGS. 4A and 4B show the binding of 353.2-1, 353.3-1, 353.5-7, and 353.9-21 antibodies to denatured KB cells (A) and non-denatured T47D cells (B) using a fluorescence activated cell sorter (FACS).
Figure 4B:
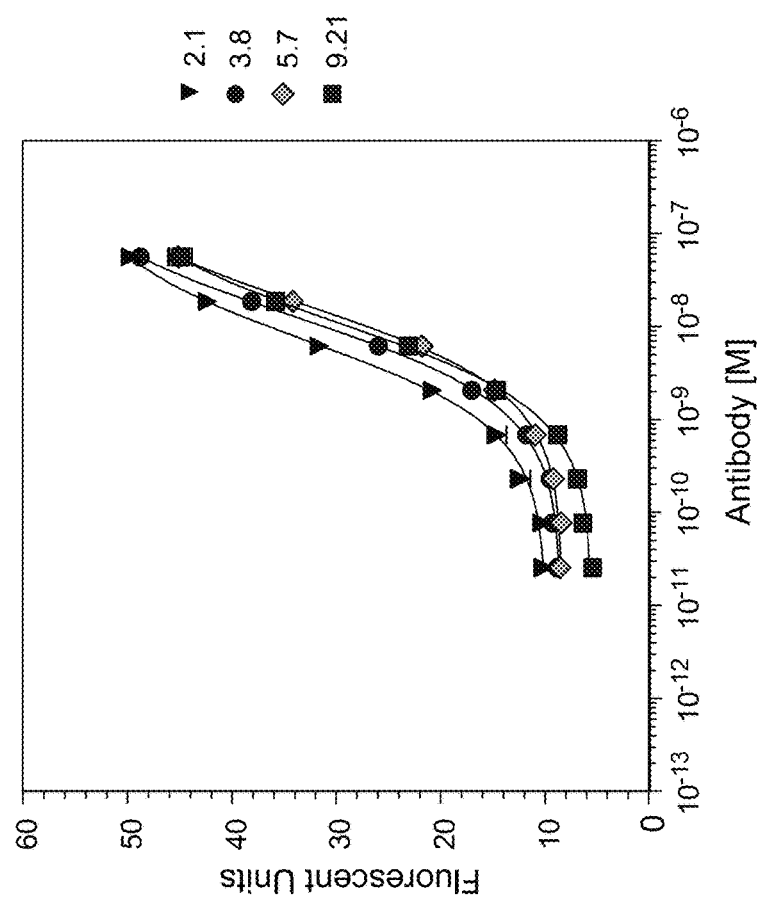

The ability of the anti-FOLR1 antibodies to bind to denatured and non-denatured (native confirmation) FOLR1 was assayed by indirect FACS with FOLR1-positive cells KB and T47D. Cells were harvested by Versine and washed with phosphate buffered saline (PBS). Denatured cells were prepared by incubation of the cells in PBS containing 10% formaldehyde at 4° C. overnight followed by washing with PBS and incubation at 95° C. for 30 min. Denatured and non-denatured cells were then incubated with anti-FOLR1 antibodies diluted in FACS buffer (RPMI-1640 medium supplemented with 2% normal goat serum) on ice for 2 hours. The cells were centrifuged, washed with PBS and incubated for 40 min with FITC-conjugated goat anti-mouse IgG-antibody. The cells were centrifuged again, washed with PBS and resuspended with 0.2 ml of PBS containing 1% formaldehyde. Cell-associated fluorescence was measured using a FACSCalibur flow cytometer with the HTS multiwell and analyzed using CellQuest Pro (BD Biosciences, San Diego, US). As shown on FIG. 4, all anti-FOLR1 antibodies bound to both denatured and not denatured cells.

Affinity of the Anti-FOLR1 Antibodies by ELISA

Figure 5:
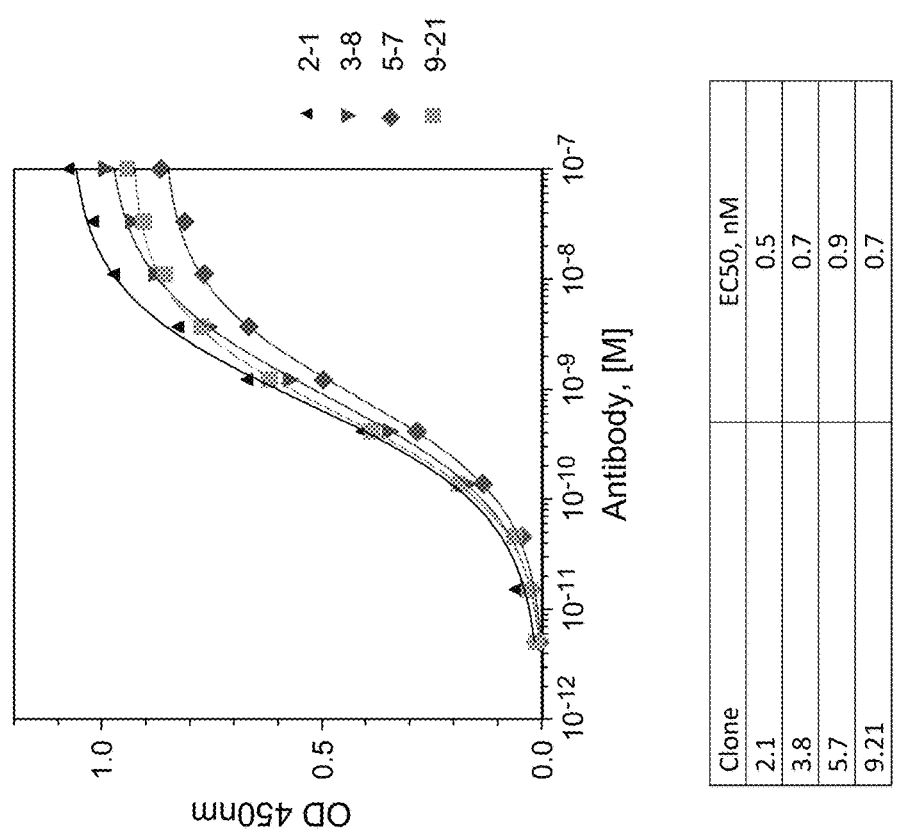
FIG. 5 shows the binding of 353.2-1, 353.3-1, 353.5-7, and 353.9-21 antibodies to recombinant human FOLR1 using ELISA.

The binding affinity of the anti-FOLR1 antibodies was examined by ELISA where recombinant humanFOLR1- murine Fc2a protein was used as the antigen. The recombinant protein was immobilized on microtiter plates, and the antibodies were added at a range of concentrations to the plates. The plates were incubated for two hours at room temperature, washed with PBS supplemented with 0.05% Tween-20, and incubated with hrp-labeled goat anti-murine secondary antibody for one hour at room temperature. The plates were washed with PBS/Tween-20 again, and bound hrp-conjugated antibody was detected by adding the hrp-substrate TMB (Bio-FX). Representative results are shown in FIG. 5. The anti-FOLR1 antibodies had similar affinity to human FOLR1 at half-maximal effective concentration (EC50) of 0.5 to 0.9 nM.

No Cross-Reactivity of the Anti-FOLR1 Antibodies with FOLR2 and FOLR3

FOLR1 is a member of Folate Receptor family. Cross-reactivity of the anti-FOLR1 antibodies with the other members of the family FOLR2 and FOLR3 was assayed by ELISA. Recombinant protein FOLR2-His or FOLR3-His (R&D Systems) was immobilized to Ni-NTA plates (QIAGEN) and the anti-FOLR1 antibodies were added to the plates and incubated for 2 hours at room temperature. As positive controls for FOLR2 and FOLR3 ELISA polyclonal anti-FOLR2 and FOLR3 antibodies (R&D systems), respectively, were used. The formed antibody-antigen complexes were detected with hip-labeled goat anti-murine secondary antibody. As shown in FIG. 6, the anti-FOLR1 antibodies of the invention did not bind to FOLR2 or FOLR3; only the control antibodies detected corresponding antigens.

Example 4

Antigen Epitope Characterization

Human FOLR1 has three potential sites for N-glycosylation at positions 69, 161 and 201 (UniProt), and, as reported in literature, all three sites are glycosylated. To characterize the nature of the epitopes recognized by the anti-FOLR1 antibodies described herein, binding experiments were performed with deglycosylated and non-treated receptor. Of the generated anti-FOLR1 clones, only clone 2.1 was used in the study because, based on the sequencing data, the clones are related and likely to bind to the same epitope. In addition to clone 2.1, two other anti-FOLR1 antibodies were included: huMov19 (WO 2011/106528) and clone BN3.2 (Leica). In order to deglycosylate FOLR1, recombinant human FOLR1 or lysates of FOLR1-positive KB or Igrov-1 cells were treated with a mixture of deglycosylation enzymes (Enzymatic DeGlycoMX Kit, QA-bio) according to the Manufacturer's protocol. Then, samples of treated and non-treated FOLR1 were used in ELISA and Western blot analysis. For the ELISA, deglycosylated and non-treated FOLR1 were immobilized to ELISA plates (Immulon), and the anti-FOLR1 antibodies FRIHC2-1 ("2.1") or huMov19 were added. After 2 h incubation, antibody-antigen complexes were detected with hip-labeled goat anti-human (for huMov19) or anti-murine (for 2.1) secondary antibody (FIG. 7). For the Western blot analysis, samples of deglycosylated and non-treated lysates or huFOLR1 recombinant protein were separated by SDS polyacrylamide gel electrophoresis and transferred to a nitrocellulose membrane by the standard procedures. The membrane was incubated with the anti-FOLR1 antibodies 2.1, huMov19, or BN3.2, and the antigen-antibody complexes were detected with the appropriate secondary anti-murine or anti human antibodies conjugated with horseradish peroxidase (FIG. 8). As shown in FIGS. 7 and 8, binding of antibody 2.1 to deglycosylated vs. non-treated FOLR1 was significantly reduced suggesting the antibody binds to a glycodependent epitope. In contrast, the other two anti-FOLR1 antibodies, huMov19 and BN3.2, bind similarly to deglycosylated and non-treated receptor indicating that (i) the FOLR1 protein was not damaged during the deglycosylation procedure and (ii) huMov19 and BN3.2 recognize protein epitopes of FOLR1.

Example 5

Cloning and Sequencing of the VL and VH Regions of the Anti-Human FOLR1 Antibodies Total cellular RNA was prepared from $5 \times 10^6$ cells of the FOLR1 hybridomas described in Example 1 using an RNeasy kit (QIAgen) according to the manufacturer's protocol. cDNA for the eight subclones clones (2.1, 2.12, 3.8, 3.9, 5.7, 5.10, 9.20, and 9.21) was subsequently synthesized from total RNA using the SuperScript II cDNA synthesis kit (Invitrogen).

The PCR procedures for amplifying the antibody variable region cDNAs derived from hybridoma cells were based on methods described in Wang et al. ((2000) J Immunol Methods. 233:167-77) and Co et al. ((1992) J Immunol. 148: 1149-54). The variable light chain (VL) and variable heavy chain (VH) sequences were amplified by degenerate primers on the 5' end and either murine kappa or IgG1 constant region specific primers respectively on the 3' end. The PCR reactions were then run on a 1% low melt agarose gel, followed by the excision of the 300 to 400 by amplicon bands that were subsequently purified using Zymo DNA mini columns. The purified amplicons were sent to Beckman Coulter Genomics for sequencing utilizing the same 5' and 3' primers of the PCR reactions in order to generate the variable region cDNA sequences from both directions.

Since the degenerate primers used to clone the VL and VH cDNA sequences alter the 5' end, additional sequencing efforts were needed to verify the complete cDNA sequences. The preliminary sequences were entered into a search query of the NCBI IgBlast site (www.ncbi.nlm.nih.gov/igblast/) to identify the murine germline sequences from which the antibody sequences had been derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

Mass Determination for Sequence Confirmation

The variable regions cDNA sequences obtained for each of the anti-FOLR1 antibodies were combined with germline constant region sequences to obtain full length antibody cDNA sequences. The molecular weights of the heavy and light chains were then calculated from translations of the cDNA sequences and compared with the molecular weights obtained by LC/MS analyses of the purified murine anti-FOLR1 antibodies. The LC/MS is done by deglycosylating and reducing the antibody to isolate full chain light and heavy chain peptides. The observed molecular weights for each of the heavy chains matched the expected, but each of the light chains was off by approximately 85 Da. Subsequent peptide fragmentation analysis by LC/MS of the light chain fragments indicated that the final serine of light chain leader peptide was in fact retained on the mature light chain, adding about 87 Da to the expected MW, thus confirming the cDNA sequences for each of the FOLR1 antibodies.

Composite CDR Sequences for the Anti-FOLR1 Antibodies

Alignments of the antibody sequences for the 8 subclones revealed that 3 of the 4 original hybridomas had produced closely related, but unique, antibodies. As expected, each of the 4 sister subclone pairs were identical. In addition two sets of subclones were also identical resulting in the 3 unique antibody sequences (SEQ ID NOs:27-32) (2.1, 5.7, and 9.20). The light and heavy chain variable framework sequences of these 3 unique antibodies are closely related, but each antibody contains unique CDRs, likely as a result of somatic amino acid substitutions (see Table 14 below). Because these CDR variants of the murine anti-FOLR1 antibodies were found to be functionally identical, they provide some structural insight into the sequence flexibility of the CDRs of the anti-FOLR1 antibodies of the invention. Light chain CDRs 2 and 3 were identical in each of the antibodies suggesting that these tightly conserved CDRs can provide a consistent structural basis for FOLR1 binding. On the other hand, the amino acid substitutions in the remaining CDRs, particularly those in heavy chain CDRs 2 and 3, suggest that these positions are critical for refinement of the affinity and specificity of these antibodies. The specific residue substitutions in these CDR positions also provide examples of residues that can be incorporated within engineered versions of these antibodies. Table 14 provides a composite CDR sequence listing compiled from the anti-FOLR1 antibodies of the invention. The composite CDRs identified herein can be used for the design of recombinant antibodies that would be expected to preserve the functional attributes of the anti-FOLR1 antibodies of the present invention.

TABLE 14

Composite CDRS

Anti-FOLR1 composite CDRs
Light Chain
CDR1:
(SEQ ID NO: 24)
KS[T/S][K/E]SLLNSDGFTYLD

CDR2:
(SEQ ID NO: 25)
LVSNHFS

CDR3:
(SEQ ID NO: 26)
FQSNYLPLT

Heavy Chain
CDR1:
(SEQ ID NO: 21)
N[Y/S]YIH

CDR2:
(SEQ ID NO: 22)
WIYP[G/E][S/N][F/V/L]N[V/T][E/R/Q]YN[E/D]KFKA

CDR3:
(SEQ ID NO: 23)
RGIY[F/Y]YSPYA[L/M]D[Y/H]

Antibody Humanization

The FRIHC2-1 antibody was humanized following resurfacing methods previously described, such as, for example in Roguska et al., Proc. Natl. Acad. Sci., USA, 91(3):969-973 (1994) and Roguska et al., Protein Eng. 9(10):895-904 (1996), which are incorporated in their entirety herein by reference. Resurfacing involves identification of the variable region framework surface residues in both the light and heavy chains and replacing them with human equivalents. The murine CDRs are preserved in the resurfaced antibody. Exemplary CDRs of FRIHC2-1 antibody are defined as indicated in Table 14. To minimize concerns about the impact of conjugating lysines that fall in CDRs, lysine 24 and lysine 27 in murine FRIHC2-1 antibody light chain CDR1 were replaced with arginine for humanized version 1.0 (shown in italic), so both versions of the LC CDR1 are given. In addition to the AbM heavy chain CDR2 definition employed for resurfacing, the table provides exemplary Kabat defined heavy chain CDR2s for both the murine and human versions of FRIHC2-1 antibody. The underlined sequence marks the portion of the Kabat heavy chain CDR2 that was not considered a CDR for resurfacing.

Surface residue positions were defined as any position with a relative accessibility of 30% or greater (Pedersen J. T. et. Al, J. Mol. Biol. 1994; 235: 959-973). The calculated surface residues were then aligned with human germline surface sequences to identify the most homologous human surface sequence. The human germline sequence used as the replacement surface for the VL domains of FRIHC2-1 antibody was IGKV2-30*01 while IHV1-69*10 was used as the replacement surface for FRIHC2-1 antibody VH. The specific framework surface residue changes for FRIHC2-1 antibody are given in FIG. 9. Since the resurfaced light chain included the CDR1 lysine substitutions in the preferred version, a resurfaced version (v1.01) was also generated with murine lysines retained in CDR-L1. FIG. 10 shows the alignment of the resurfaced sequences for FRIHC2-1 variable domain of both light and heavy chain with their murine counterparts.

In addition to humanization by variable domain resurfacing, FRIHC2-1 antibody was also humanized following complementary determining region (CDR) grafting technology (Jones et al., Nature 321: 604-608 (1986) and Verhoeyen et al., Science 239: 1534-1536 (1988)). The CDR grafting method consists of grafting the CDRs from a naturally evolved murine antibody onto the Fv framework regions (FRs) of a human antibody. The Kabat numbering scheme and Kabat CDR definitions were used for CDR grafting of the FRIHC2-1 antibody. Exemplary CDRs of FRIHC2-1 for CDR grafting are given in Table 14. The human immunoglobulin germline sequence with the highest homology to the murine FRIHC2-1 antibody was identified through the interactive tool, V-QUEST, of the International ImMunoGeneTics information System® (IMGT (http://imgt.cines.fr/) as described in Lefranc, Nucleic Acids Res. 29: 207-209 (2001). The human germline sequences used as the acceptor frameworks for the VL and VH domains of FRIHC2-1 antibody were IGKV2D-29*02 and IGHV1-2*02, respectively. To minimize concerns about the impact of conjugating lysines that fall in CDRs, lysine 24 and lysine 27 in murine FRIHC2-1 antibody light chain CDR1 were replaced with arginine in the CDR grafted constructs (Table 15). The specific framework residue changes as well as the substitution in CDR-L1 in CDR-grafting of FRIHC2-1 antibody are given in FIG. 11, and the alignments of the CDR-grafted sequences for the FRIHC2-1 antibody variable domains with its murine counterparts are illustrated in FIG. 12.

TABLE 15

| FRIHC2-1 CDR's (Resurfacing) | FRIHC2-1 CDR's (CDR grafting) |
|---|---|
| Light Chain | Light Chain |
| Murine and resurfaced v1.01 CDR1: KSSKSLLNSDGFTYLD (SEQ ID NO: 6) | Murine and CDR-grafted v1.01 CDR1: KSSKSLLNSDGFTYLD (SEQ ID NO: 6) |
| Resurfaced v1.0 CDR1: RSSRSLLNSDGFTYLD (SEQ ID NO: 59) | CDR-grafted v1.0 CDR1: RSSRSLLNSDGFTYLD (SEQ ID NO: 59) |
| CDR2: LVSNHFS (SEQ ID NO: 7) | CDR2: LVSNHFS (SEQ ID NO: 7) |
| CDR3: FQSNYLPLT (SEQ ID NO: 8) | CDR3: FQSNYLPLT (SEQ ID NO: 8) |
| Heavy Chain | Heavy Chain |
| CDR1: NSYIH (SEQ ID NO: 3) | CDR1: NSYIH (SEQ ID NO: 3) |
| CDR2: WIYPESLNTQ (SEQ ID NO: 60) | CDR2: WIYPESLNTQYNEKFKA (SEQ ID NO: 4) |
| CDR3: RGIYYYSPYALDH (SEQ ID NO: 5) | CDR3: RGIYYYSPYALDH (SEQ ID NO: 5) |
| Kabat FRIHC2-1 HC CDR2 Murine HC CDR2: WIYPESLNTQYNEKFKA (SEQ ID NO: 4) | |
| Resurfaced HC CDR2: WIYPESLNTQYNQKFQG (SEQ ID NO: 61) | |

Example 6

IHC Evaluation of 353-2.1 (FOLR1-2.1) Antibody Using Human Tumor Samples

Human tumor samples representative of ovarian cancer (n=63), lung adenocarcinoma (n=104), and endometrial adenocarcinoma (n=58) were evaluated for FOLR1 expression by IHC using the 353-2.1 antibody. The intensity of FOLR1 staining and the distribution of scores are summarized in Table 16, below. FIG. 15 shows an example of staining of ovarian cancer and lung adenocarcinoma tissue with the 353-2.1 antibody. These results demonstrate the utility of 353-2.1 as a specific and sensitive antibody for use in IHC assays to identify patients as potential candidates for therapy with FOLR1 targeting agents (e.g., IMGN853).

TABLE 16

Distribution of Scores (% Positivity)

| TUMOR TYPE: | OVARIAN CANCER n = 63 | LUNG ADENO- CARCINOMA n = 104 | ENDOMETRIAL ADENO- CARCINOMA n = 58 |
|---|---|---|---|
| Positive (any intensity): | 65% | 70% | 64% |
| ≥level 2 intensity with at least 25% tumor cells stained: | 59% | 47% | 33% |
| ≥level 3 intensity with at least 25% tumor cells stained: | 51% | 19% | 14% |

The unique antigen specificity and high binding affinity of the FOLR1-2.1 (FOLR1 353-2.1) antibody was further demonstrated using an additional IHC assay. This IHC assay utilizes the OptiView DAB Detection Kit on a Ventana BenchMark XT automated slide stainer for semi-quantitative determination of FOLR1 protein expression in formalin-fixed paraffin embedded tissue samples. The assay has been optimized and validated with respect to specificity, sensitivity, and precision using normal and tumor tissue controls. Under the optimized condition, sharp membranous staining was clearly observed in tumor cellss whereas normal stromal tissues were completely negative. (FIG. 16). In addition, this assay also achieved a broader dynamic range thereby allowing better discrimination of moderate staining intensity (level 2, medium brown staining, FIG. 17) from the strongest staining intensity (level 3, dark brown staining, FIG. 17). The enhanced dynamic range improves the ability to rank FOLR1 positive samples based on staining intensity and enable further identification a sub-popupation of patients with the highest level of FOLR1 expression.

A BN3.2 (Leica) antibody and the FOLR1-2.1 (FOLR1 353-2.1) antibody were compared using an ovarian cancer tissue micro array (TMA). Using the BN3.2 (Leica) antibody in an IHC assay (BN3.2 assay), close to 50% of samples (16 out of 35) were scored in the highest category (level 3 staining intensity on at least 25% tumor cells). In contrast, using the FOLR1-2.1 (FOLR1 353-2.1) antibody in the IHC assay described above utilizing the OptiView DAB Detection Kit on a Ventana BenchMark XT automated slide stainer (FOLR1-2.1 assay), allowed further separation of these 16 samples into 2 different categories: 6 in the highest category (level 3 staining intensity on at least 25% tumor cells, Table 17), and the other 10 in the second highest category (level 2 staining intensity on at least 25% tumor cells, Table 17). Thus, the more discreet staining obtained with the FOLR1-2.1 antibody in the FOLR1-2.1 assay allows for discrimination among samples all grouped together as samples with level 3 expression using the BN3.2 antibody in the BN3.2 assay.

TABLE 17

FOLR1 prevalence comparison in ovarian cancer TMA (n = 35)

| Score | FOLR1-2.1 assay | BN3.2 assay |
|---|---|---|
| Positive (any intensity) | 24 (69%) | 28 (80%) |
| ≥level 1 intensity with at least 25% tumor cells stained: | 21 (60%) | 27 (77%) |

TABLE 17-continued

FOLR1 prevalence comparison in ovarian cancer TMA (n = 35)

| Score | FOLR1-2.1 assay | BN3.2 assay |
|---|---|---|
| ≥level 2 intensity with at least 25% tumor cells stained: | 17 (49%) | 25 (71%) |
| ≥level 3 intensity with at least 25% tumor cells stained: | 6 (17%) | 16 (46%) |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. A monoclonal antibody or antigen-binding fragment thereof that specifically binds to the same folate receptor 1 (FOLR1) epitope as an antibody comprising a heavy chain variable region (VH) comprising the amino acid sequence of SEQ ID NO:27 and a light chain variable region (VL) comprising the amino acid sequence of SEQ ID NO:28, wherein the monoclonal antibody or antigen-binding fragment thereof binds to an epitope of FOLR1 comprising an N-glycosylated amino acid.

2. The monoclonal antibody or antigen-binding fragment thereof of claim 1, wherein the antibody or fragment thereof comprises the VH CDR1-3 and VL CDR1-3 polypeptide sequences selected from the group consisting of:
   (a) SEQ ID NOs:3-8, respectively;
   (b) SEQ ID NOs:9-14, respectively;
   (c) SEQ ID NOs:15-20, respectively;
   (d) SEQ ID NOs: 3-5 and SEQ ID NOs: 59, 7, and 8, respectively;
   (e) SEQ ID NOs: 3, 60, and 5 and SEQ ID NOs: 6-8, respectively;
   (e) SEQ ID NOs: 3, 61, and 5 and SEQ ID NOs: 6-8, respectively;
   (g) SEQ NOs: 3, 60, and 5 and SEQ ID NOs: 59, 7, and 8, respectively; and
   (h) SEQ ID NOs: 3, 61, and 5 and SEQ ID NOs: 59, 7, and 8, respectively.

3. A polypeptide that specifically binds FOLR1, wherein said polypeptide comprises VH CDR1-3 and VL CDR1-3 polypeptide sequences selected from the group consisting of:
   (a) SEQ ID NOs:3-8, respectively;
   (b) SEQ ID NOs:9-14, respectively;
   (c) SEQ ID NOs: 15-20, respectively;
   (d) SEQ ID NOs: 3-5 and SEQ ID NOs: 59, 7, and 8, respectively;
   (e) SEQ ID NOs: 3, 60, and 5 and SEQ ID NOs: 6-8, respectively;

(f) SEQ ID NOs: 3, 61, and 5 and SEQ NOs: 6-8, respectively;

(f) SEQ ID NOs: 3, 60, and 5 and SEQ ID NO 59, 7, and 8, respectively; and (h) SEQ ID NOs: 3, 61, and 5 and SEQ ID NOs: 59, 7, and 8, respectively.

4. A composition comprising the monoclonal antibody or antigen-binding fragment thereof of claim 1 and a buffer selected from the group consisting of: a FACS buffer, an IHC buffer, and an ELISA buffer.

5. A monoclonal antibody or antigen-binding fragment thereof that specifically binds to FOLR1, wherein said antibody or fragment thereof competitively inhibits binding to FOLR1 of an antibody comprising a heavy chain variable region (VH) comprising the amino acid sequence of SEQ ID NO:27 and a light chain variable region (VL) comprising the amino acid sequence of SEQ ID NO:28, wherein the monoclonal antibody or antigen-binding fragment thereof binds to an epitope of FOLR1 comprising an N-glycosylated amino acid.

6. The monoclonal antibody or antigen-binding fragment thereof that specifically binds to FOLR1 of claim 5, comprising a heavy chain variable region (VH) and a light chain variable region (VL) selected from the group consisting of:
 a heavy chain variable region (VH) comprising the amino acid sequence of SEQ ID NO:27 and a light chain variable region (VL) comprising the amino acid sequence of SEQ ID NO:28;
 a heavy chain variable region (VH) comprising the amino acid sequence of SEQ ID NO:29 and a light chain variable region (VL) comprising the amino acid sequence of SEQ ID NO:30;
 a heavy chain variable region comprising the amino acid sequence of SEQ ID NO:31 and a light chain variable region (VL) comprising the amino acid sequence of SEQ ID NO:32;
 a heavy chain variable region (VH) comprising the amino acid sequence of SEQ ID NO:62 and a light chain variable region (VL) comprising the amino acid sequence of SEQ ID NO:63 or SEQ ID NO:64; and
 a heavy chain variable region (VH) comprising the amino acid sequence of SEQ ID NO:65 and a light chain variable region (VL) comprising the amino acid sequence of SEQ NO:66 or SEQ ID NO:67.

7. The monoclonal antibody or antigen-binding fragment thereof of claim 5, wherein said antibody or antigen-binding fragment thereof is chimeric or humanized.

8. The monoclonal antibody or antigen-binding fragment thereof of claim 5, which is a full-length antibody.

9. The monoclonal antibody or antigen-binding fragment thereof of claim 5, which is an antigen-binding fragment.

10. The monoclonal antibody or antigen-binding fragment thereof of claim 5, which binds to a human folate receptor 1 with a Kd of about 0.5 to about 10 nM.

11. The monoclonal antibody or antigen-binding fragment thereof of claim 5, which binds to a human folate receptor 1 with a Kd of about 1.0 nM or less.

12. The monoclonal antibody or antigen-binding fragment thereof of claim 5, wherein the antibody or antigen-binding fragment thereof is detectably labeled.

13. The monoclonal antibody or antigen-binding fragment thereof of claim 12, wherein said detectable label is selected from the group consisting of immunofluorescent label, chemiluminescent label, phosphorescent label, enzyme label, radiolabel, avidin/biotin, colloidal gold particles, colored particles and magnetic particles.

14. An antibody or antigen-binding fragment thereof that specifically binds to FOLR1, wherein said antibody or fragment thereof comprises the VH CDR1-3 and VL CDR1-3 polypeptide sequences of SEQ ID NOs: 3-8, respectively.

15. The antibody or antigen-binding fragment thereof of claim 14, wherein the antibody or fragment thereof comprises a heavy chain variable region (VH) comprising the amino acid sequence of SEQ ID NO:27 and a light chain variable region (VL) comprising the amino acid sequence of SEQ ID NO:28.

16. An antibody or antigen-binding fragment thereof that specifically binds to FOLR1, wherein said antibody or fragment thereof comprises the VH CDR1-3 and VL CDR1-3 polypeptide sequences of SEQ ID NOs: 9-14, respectively.

17. The antibody or antigen-binding fragment thereof of claim 16, wherein the antibody or fragment thereof comprises a heavy chain variable region (VH) comprising the amino acid sequence of SEQ ID NO:29 and a light chain variable region (VL) comprising the amino acid sequence of SEQ ID NO:30.

18. An antibody or antigen-binding fragment thereof that specifically binds to FOLR1, wherein said antibody or fragment thereof comprises the VH CDR1-3 and VL CDR1-3 polypeptide sequences of SEQ ID NOs: 15-20, respectively.

19. The antibody or antigen-binding fragment thereof of claim 18, wherein the antibody or fragment thereof comprises a heavy chain variable region (VH) comprising the amino acid sequence of SEQ ID NO:31 and a light chain variable region (VL) comprising the amino acid sequence of SEQ ID NO:32.

20. The antibody or antigen-binding fragment thereof of claim 14, wherein the antibody or antigen-binding fragment thereof is detectably labeled.

21. The antibody or antigen-binding fragment thereof of claim 20, wherein said detectable label is selected from the group consisting of: immunofluorescent label, chemiluminescent label, phosphorescent label, enzyme label, radiolabel, avidin/biotin, colloidal gold particles, colored particles and magnetic particles.

22. A composition comprising the antibody or antigen-binding fragment thereof of claim 14 and a buffer selected from the group consisting of: a FACS buffer, an IHC buffer, and an ELISA buffer.

23. The antibody or antigen-binding fragment thereof of claim 16, wherein the antibody or antigen-binding fragment thereof is detectably labeled.

24. The antibody or antigen-binding fragment thereof of claim 23, wherein said detectable label is selected from the group consisting of: immunofluorescent label, chemiluminescent label, phosphorescent label, enzyme label, radiolabel, avidin/biotin, colloidal gold particles, colored particles and magnetic particles.

25. A composition comprising the antibody or antigen-binding fragment thereof of claim 16 and a buffer selected from the group consisting of: a FACS buffer, an IHC buffer, and an ELISA buffer.

26. The antibody or antigen-binding fragment thereof of claim 18, wherein the antibody or antigen-binding fragment thereof is detectably labeled.

27. The antibody or antigen-binding fragment thereof of claim 26, wherein said detectable label is selected from the group consisting of: immunofluorescent label, chemiluminescent label, phosphorescent label, enzyme label, radiolabel, avidin/biotin, colloidal gold particles, colored particles and magnetic particles.

28. A composition comprising the antibody or antigen-binding fragment thereof of claim 18 and a buffer selected from the group consisting of: a FACS buffer, an IHC buffer, and an ELISA buffer.

29. The antibody or antigen-binding fragment thereof of claim 15, wherein the antibody or antigen-binding fragment thereof is detectably labeled.

30. The antibody or antigen-binding fragment thereof of claim 29, wherein said detectable label is selected from the group consisting of: immunofluorescent label, chemiluminescent label, phosphorescent label, enzyme label, radiolabel, avidin/biotin, colloidal gold particles, colored particles and magnetic particles.

31. A composition comprising the antibody or antigen-binding fragment thereof of claim 15 and a buffer selected from the group consisting of: a FACS buffer, an IHC buffer, and an ELISA buffer.

32. The antibody or antigen-binding fragment thereof of claim 15, wherein the antibody or fragment thereof comprises a heavy chain comprising the amino acid sequence of SEQ ID NO:33 and a light chain comprising the amino acid sequence of SEQ ID NO:34.

33. The antibody or antigen-binding fragment thereof of claim 17, wherein the antibody or fragment thereof comprises a heavy chain comprising the amino acid sequence of SEQ ID NO:35 and a light chain comprising the amino acid sequence of SEQ ID NO:36.

34. The antibody or antigen-binding fragment thereof of claim 19, wherein the antibody or fragment thereof comprises a heavy chain comprising the amino acid sequence of SEQ ID NO:37 and a light chain comprising the amino acid sequence of SEQ ID NO:38.

35. A hybridoma producing the monoclonal antibody or antigen-binding fragment thereof of claim 1.

36. A method of making the monoclonal antibody or antigen-binding fragment thereof of claim 1, comprising (a) culturing the hybridoma of claim 35; and (b) isolating said antibody or antigen-binding fragment thereof from said cultured hybridoma.

* * * * *

UNITED STATES PATENT AND TRADEMARK OFFICE
CERTIFICATE OF CORRECTION

PATENT NO. : 9,637,547 B2
APPLICATION NO. : 14/473828
DATED : May 2, 2017
INVENTOR(S) : Ab et al.

Page 1 of 1

It is certified that error appears in the above-identified patent and that said Letters Patent is hereby corrected as shown below:

In the Claims

Column 140, Line 52, "(e)" is replaced with --(f)--;

Column 141, Line 3, "(f)" is replaced with --(g)--; and

Column 141, Line 34, "variable region comprising" is replaced with --variable region (VH) comprising--.

Signed and Sealed this
Thirtieth Day of April, 2019

Andrei Iancu
*Director of the United States Patent and Trademark Office*